US008679061B2

(12) United States Patent
Julian et al.

(10) Patent No.: US 8,679,061 B2
(45) Date of Patent: Mar. 25, 2014

(54) AUTOMATIC INJECTION DEVICE

(75) Inventors: Joseph F. Julian, Libertyville, IL (US);
Steven Rolfe, Hertforfshire (GB);
Stephen Bicknell, Warwickshire (GB);
Jeremy Marshall, Oxford (GB)

(73) Assignee: Abbvie Biotechnology Ltd, Hamilton (BM)

( * ) Notice: Subject to any disclaimer, the term of this patent is extended or adjusted under 35 U.S.C. 154(b) by 1335 days.

(21) Appl. No.: 12/074,704

(22) Filed: Mar. 5, 2008

(65) Prior Publication Data

US 2010/0160894 A1   Jun. 24, 2010

Related U.S. Application Data

(63) Continuation of application No. 11/824,516, filed on Jun. 29, 2007, now abandoned.

(60) Provisional application No. 60/817,849, filed on Jun. 30, 2006, provisional application No. 60/838,905, filed on Aug. 18, 2006, provisional application No. 60/818,231, filed on Jun. 30, 2006, provisional application No. 60/849,967, filed on Oct. 6, 2006, provisional application No. 60/904,626, filed on Mar. 1, 2007, provisional application No. 60/918,174, filed on Mar. 14, 2007, provisional application No. 60/899,262, filed on Feb. 2, 2007.

(51) Int. Cl.
*A61M 5/20*     (2006.01)
(52) U.S. Cl.
USPC ............................ 604/136; 604/135; 604/157
(58) Field of Classification Search
USPC ......... 604/131, 134–137, 157, 187, 192, 197, 604/198, 218, 221, 224, 225, 229
See application file for complete search history.

(56) References Cited

U.S. PATENT DOCUMENTS 2,398,544 A   4/1946   Lockhart
2,459,875 A   1/1949   Folkman
(Continued)

FOREIGN PATENT DOCUMENTS

DE      2019296    11/1971
DE     19821933    11/1999
(Continued)

OTHER PUBLICATIONS

Nov. 10, 1999 correspondence from Dept. of Health & Human Services, Food and Drug Administration to Robert Shaw/Owen Mumford regarding Section 501(k) notification intent to market device.

(Continued)

*Primary Examiner* — Kami A Bosworth
(74) *Attorney, Agent, or Firm* — McCarter & English, LLP; David R. Burns

(57)   ABSTRACT

An automatic injection device for providing a subcutaneous injection is disclosed. The device includes a syringe movably disposed in a housing and including a barrel portion, a needle and a bung for sealing the barrel portion. The device includes a plunger for moving the syringe towards a first open end of the housing such that the needle projects from the first end and subsequently applying pressure to the bung. The plunger includes a rod connected at a first end to the bung, a compressible expanded central portion, and a flange between a second end of the rod and the central portion. The device includes a biasing mechanism for biasing the plunger towards the first open end of the housing, the biasing mechanism disposed about the second end of the rod between the flange and the second end of the housing.

43 Claims, 20 Drawing Sheets

(56) References Cited

U.S. PATENT DOCUMENTS

| | | |
|---|---|---|
| 2,565,081 A | 8/1951 | Maynes |
| 2,591,457 A | 4/1952 | Maynes |
| 2,701,566 A | 2/1955 | Krug |
| 2,751,918 A | 7/1956 | Uytenbogaart |
| 2,832,339 A | 4/1958 | Sarnoff et al. |
| 2,888,924 A | 9/1959 | Dunmire |
| 2,960,087 A | 11/1960 | Uytenbogaart |
| 3,051,173 A | 8/1962 | Johnson et al. |
| 3,055,362 A | 9/1962 | Uytenbogaart |
| 3,066,670 A | 12/1962 | Stauffer |
| 3,136,313 A | 6/1964 | Enström et al. |
| 3,314,428 A | 4/1967 | Johnson et al. |
| 3,330,279 A | 7/1967 | Sarnoff et al. |
| 3,403,680 A | 10/1968 | Sinclair et al. |
| 3,496,937 A | 2/1970 | Fletcher |
| 3,541,663 A | 11/1970 | Szpur |
| 3,543,603 A | 12/1970 | Gley |
| 3,605,743 A | 9/1971 | Arce |
| 3,618,603 A | 11/1971 | Levenson |
| 3,702,609 A | 11/1972 | Steiner |
| 3,712,301 A | 1/1973 | Sarnoff |
| 3,742,948 A | 7/1973 | Post et al. |
| 3,797,488 A | 3/1974 | Hurschman et al. |
| 3,797,489 A | 3/1974 | Sarnoff |
| 3,882,863 A | 5/1975 | Sarnoff et al. |
| 3,892,237 A | 7/1975 | Steiner |
| 3,910,260 A | 10/1975 | Sarnoff et al. |
| 3,941,130 A | 3/1976 | Tibbs |
| 4,004,577 A | 1/1977 | Sarnoff |
| 4,031,893 A | 6/1977 | Kaplan et al. |
| 4,106,770 A | 8/1978 | Gray |
| 4,178,928 A | 12/1979 | Tischlinger |
| 4,202,314 A | 5/1980 | Smirnov et al. |
| 4,214,584 A | 7/1980 | Smirnov et al. |
| 4,226,235 A | 10/1980 | Sarnoff et al. |
| 4,258,713 A | 3/1981 | Wardlaw |
| 4,261,358 A | 4/1981 | Vargas et al. |
| 4,275,729 A | 6/1981 | Silver et al. |
| 4,394,863 A | 7/1983 | Bartner |
| 4,399,216 A | 8/1983 | Axel et al. |
| 4,425,120 A | 1/1984 | Sampson et al. |
| 4,437,859 A | 3/1984 | Whitehouse et al. |
| 4,447,231 A | 5/1984 | Bekkering |
| 4,510,245 A | 4/1985 | Cousens et al. |
| 4,530,695 A | 7/1985 | Phillips et al. |
| 4,565,543 A | 1/1986 | Bekkering et al. |
| 4,573,976 A | 3/1986 | Sampson et al. |
| 4,578,064 A | 3/1986 | Sarnoff et al. |
| 4,624,660 A | 11/1986 | Mijers et al. |
| 4,634,665 A | 1/1987 | Axel et al. |
| 4,637,403 A | 1/1987 | Garcia et al. |
| 4,640,686 A | 2/1987 | Dalling et al. |
| 4,664,653 A | 5/1987 | Sagstetter et al. |
| 4,678,461 A | 7/1987 | Mesa |
| 4,689,042 A | 8/1987 | Sarnoff et al. |
| 4,723,937 A | 2/1988 | Sarnoff et al. |
| 4,755,169 A | 7/1988 | Sarnoff et al. |
| 4,795,432 A | 1/1989 | Karczmer |
| 4,795,433 A | 1/1989 | Sarnoff |
| 4,816,567 A | 3/1989 | Cabilly et al. |
| 4,820,286 A | 4/1989 | van der Wal |
| 4,822,340 A | 4/1989 | Kamstra |
| 4,850,994 A | 7/1989 | Zerbs et al. |
| 4,852,768 A | 8/1989 | Bartsch |
| 4,902,279 A | 2/1990 | Schmidtz et al. |
| 4,923,447 A | 5/1990 | Morgan |
| 4,927,416 A | 5/1990 | Tomkiel |
| 4,929,237 A | 5/1990 | Medway |
| 4,955,868 A | 9/1990 | Klein |
| 4,966,592 A | 10/1990 | Burns et al. |
| 4,968,615 A | 11/1990 | Koszinowski |
| 4,994,034 A | 2/1991 | Botich et al. |
| 5,041,088 A | 8/1991 | Ritson et al. |
| 5,042,977 A | 8/1991 | Bechtold et al. |
| 5,049,133 A | 9/1991 | Villen Pascual |
| D322,479 S | 12/1991 | Miyaguchi |
| 5,085,641 A | 2/1992 | Sarnoff et al. |
| 5,085,642 A | 2/1992 | Sarnoff et al. |
| 5,092,842 A | 3/1992 | Bechtold et al. |
| 5,092,843 A | 3/1992 | Monroe et al. |
| 5,102,393 A | 4/1992 | Sarnoff et al. |
| 5,104,380 A | 4/1992 | Holman et al. |
| 5,114,406 A | 5/1992 | Gabriel et al. |
| 5,114,410 A | 5/1992 | Caralt Batlle |
| 5,137,516 A | 8/1992 | Rand et al. |
| 5,163,918 A | 11/1992 | Righi et al. |
| 5,168,062 A | 12/1992 | Stinski |
| 5,179,017 A | 1/1993 | Axel et al. |
| 5,201,708 A | 4/1993 | Martin |
| 5,223,409 A | 6/1993 | Ladner et al. |
| 5,224,936 A | 7/1993 | Gallagher |
| 5,225,539 A | 7/1993 | Winter |
| 5,231,024 A | 7/1993 | Moeller et al. |
| 5,242,240 A | 9/1993 | Gorham |
| 5,244,465 A | 9/1993 | Michel |
| 5,259,840 A | 11/1993 | Boris |
| 5,263,934 A | 11/1993 | Haak |
| 5,267,963 A | 12/1993 | Bachynsky |
| 5,267,972 A | 12/1993 | Anderson |
| 5,267,976 A | 12/1993 | Guerineau et al. |
| 5,273,544 A | 12/1993 | van der Wal |
| D343,897 S | 2/1994 | Rand et al. |
| 5,295,965 A | 3/1994 | Wilmot |
| 5,295,975 A | 3/1994 | Lockwood, Jr. |
| 5,298,024 A | 3/1994 | Richmond |
| D346,219 S | 4/1994 | Fardigh |
| 5,300,030 A * | 4/1994 | Crossman et al. ............ 604/136 |
| 5,318,538 A | 6/1994 | Martin |
| 5,320,609 A | 6/1994 | Haber et al. |
| 5,334,144 A | 8/1994 | Alchas et al. |
| 5,342,308 A | 8/1994 | Boschetti |
| 5,346,480 A | 9/1994 | Hess et al. |
| 5,358,489 A | 10/1994 | Wyrick |
| 5,376,080 A | 12/1994 | Petrussa |
| 5,378,233 A | 1/1995 | Haber et al. |
| 5,383,864 A | 1/1995 | van den Heuvel |
| 5,383,865 A | 1/1995 | Michel |
| 5,391,151 A | 2/1995 | Wilmot |
| 5,425,715 A | 6/1995 | Dalling et al. |
| 5,433,712 A | 7/1995 | Stiles et al. |
| 5,478,316 A | 12/1995 | Bitdinger et al. |
| 5,480,387 A | 1/1996 | Gabriel et al. |
| 5,530,101 A | 6/1996 | Queen et al. |
| 5,531,705 A | 7/1996 | Alter et al. |
| 5,567,160 A | 10/1996 | Massino |
| 5,569,192 A | 10/1996 | van der Wal |
| 5,585,089 A | 12/1996 | Queen et al. |
| 5,591,138 A | 1/1997 | Vaillancourt |
| 5,599,309 A | 2/1997 | Marshall et al. |
| 5,616,128 A | 4/1997 | Meyer |
| 5,620,421 A | 4/1997 | Schmitz |
| 5,634,906 A | 6/1997 | Haber et al. |
| 5,637,094 A | 6/1997 | Stewart, Jr. et al. |
| 5,645,534 A | 7/1997 | Chanoch |
| 5,656,272 A | 8/1997 | Le et al. |
| 5,658,259 A | 8/1997 | Pearson et al. |
| 5,681,291 A | 10/1997 | Galli |
| 5,693,761 A | 12/1997 | Queen et al. |
| 5,693,762 A | 12/1997 | Queen et al. |
| 5,744,360 A | 4/1998 | Hu et al. |
| 5,779,677 A | 7/1998 | Frezza |
| 5,807,335 A * | 9/1998 | Kriesel et al. ................. 604/131 |
| 5,807,346 A | 9/1998 | Frezza |
| 5,817,111 A | 10/1998 | Riza |
| 5,843,036 A | 12/1998 | Olive et al. |
| 5,860,957 A | 1/1999 | Jacobsen |
| 5,885,250 A | 3/1999 | Kriesel et al. |
| 5,931,817 A | 8/1999 | Nguyen et al. |
| 5,957,886 A | 9/1999 | Weston |
| 5,957,897 A | 9/1999 | Jeffrey |
| 5,984,900 A | 11/1999 | Mikkelsen |
| 5,993,421 A | 11/1999 | Kriesel |
| 6,048,336 A | 4/2000 | Gabriel |
| 6,056,728 A | 5/2000 | von Schuckmann |

(56) References Cited

U.S. PATENT DOCUMENTS

| | | | |
|---|---|---|---|
| 6,077,247 A | 6/2000 | Marshall et al. |
| 6,090,070 A | 7/2000 | Hager et al. |
| 6,090,080 A | 7/2000 | Jost et al. |
| 6,090,382 A | 7/2000 | Salfeld et al. |
| 6,099,503 A | 8/2000 | Stradella |
| 6,102,896 A | 8/2000 | Roser |
| 6,110,147 A | 8/2000 | Perouse |
| 6,149,626 A | 11/2000 | Bachynsky et al. |
| 6,159,181 A | 12/2000 | Crossman et al. |
| 6,171,285 B1 | 1/2001 | Johnson |
| 6,203,530 B1 | 3/2001 | Stewart, Sr. |
| 6,210,369 B1 | 4/2001 | Wilmot et al. |
| 6,213,987 B1 | 4/2001 | Hirsch |
| 6,221,044 B1 | 4/2001 | Greco |
| 6,241,709 B1 | 6/2001 | Bechtold et al. |
| 6,258,068 B1 | 7/2001 | Kirchhofer et al. |
| 6,258,562 B1 | 7/2001 | Salfeld et al. |
| 6,270,479 B1 | 8/2001 | Bergens et al. |
| 6,277,097 B1 | 8/2001 | Mikkelsen et al. |
| 6,277,098 B1 | 8/2001 | Klitmose et al. |
| 6,277,099 B1 | 8/2001 | Strowe et al. |
| 6,280,421 B1 | 8/2001 | Kirchhofer et al. |
| 6,312,412 B1 | 11/2001 | Saled et al. |
| 6,319,233 B1 | 11/2001 | Jansen et al. |
| 6,319,234 B1 | 11/2001 | Restelli et al. |
| 6,322,540 B1 | 11/2001 | Grabis et al. |
| 6,371,939 B2 | 4/2002 | Bergens et al. |
| 6,387,074 B1 | 5/2002 | Horppu et al. |
| 6,387,078 B1 | 5/2002 | Gillespie, III |
| 6,413,237 B1 | 7/2002 | Caizza et al. |
| 6,419,658 B1 | 7/2002 | Resfelli et al. |
| D461,555 S | 8/2002 | Binet et al. |
| 6,451,983 B2 | 9/2002 | Rathjen et al. |
| 6,454,746 B1 | 9/2002 | Bydlon et al. |
| 6,475,194 B2 | 11/2002 | Domici, Jr. et al. |
| 6,498,237 B2 | 12/2002 | Rathjen et al. |
| 6,502,699 B1 | 1/2003 | Watson |
| 6,509,015 B1 | 1/2003 | Salfeld et al. |
| 6,517,517 B1 | 2/2003 | Farrugia et al. |
| 6,544,234 B1 | 4/2003 | Gabriel |
| 6,575,939 B1 | 6/2003 | Brunel |
| 6,589,210 B1 | 7/2003 | Rolfe |
| 6,593,458 B1 | 7/2003 | Rathjen et al. |
| 6,656,163 B1 | 12/2003 | Marshall et al. |
| 6,656,164 B1 | 12/2003 | Smith |
| 6,673,035 B1 | 1/2004 | Rice et al. |
| 6,692,469 B1 | 2/2004 | Weekes et al. |
| 6,712,788 B2 | 3/2004 | Righi et al. |
| 6,743,203 B1 | 6/2004 | Pickhard |
| 6,752,798 B2 | 6/2004 | McWethy et al. |
| 6,767,336 B1 | 7/2004 | Kaplan |
| D494,270 S | 8/2004 | Reschke |
| 6,773,415 B2 | 8/2004 | Heiniger |
| 6,796,967 B2 | 9/2004 | Jensen |
| 6,802,827 B2 | 10/2004 | Andersson |
| 6,805,686 B1 | 10/2004 | Fathallah et al. |
| 6,808,507 B2 | 10/2004 | Roser |
| 6,817,989 B2 | 11/2004 | Svendsen et al. |
| 6,872,194 B2 | 3/2005 | Doyle et al. |
| 6,926,697 B2 | 8/2005 | Malenchek |
| 6,932,793 B1 | 8/2005 | Marshall et al. |
| 6,945,960 B2 | 9/2005 | Barker et al. |
| 6,976,976 B2 | 12/2005 | Doyle |
| 6,986,760 B2 | 1/2006 | Giambattista et al. |
| 7,004,929 B2 | 2/2006 | McWethy et al. |
| D518,175 S | 3/2006 | Hardin et al. |
| 7,056,306 B1 | 6/2006 | Halseth |
| 7,223,394 B2 | 5/2007 | Salfeld et al. |
| 7,320,682 B2 | 1/2008 | Cocker |
| 7,361,160 B2 | 4/2008 | Hommann et al. |
| 7,497,847 B2 | 3/2009 | Crawford et al. |
| 7,541,031 B2 | 6/2009 | Salfeld et al. |
| 7,588,761 B2 | 9/2009 | Salfeld et al. |
| 7,694,828 B2 * | 4/2010 | Swift et al. ................ 210/512.3 |
| 7,736,333 B2 | 6/2010 | Gillespie, III |
| D622,374 S | 8/2010 | Julian et al. |
| D629,509 S | 12/2010 | Julian et al. |
| 7,863,426 B2 | 1/2011 | Wan et al. |
| 7,919,264 B2 | 4/2011 | Maksymowych et al. |
| D638,935 S | 5/2011 | Gilmore et al. |
| 7,938,802 B2 | 5/2011 | Bicknell et al. |
| 8,162,887 B2 | 4/2012 | Bicknell et al. |
| 8,372,030 B2 | 2/2013 | Dixon et al. |
| D677,380 S | 3/2013 | Julian et al. |
| 2001/0005781 A1 | 6/2001 | Bergens |
| 2001/0025168 A1 | 9/2001 | Gross |
| 2001/0053894 A1 | 12/2001 | Steenfeldt-Jensen et al. |
| 2002/0002344 A1 | 1/2002 | Douglas et al. |
| 2002/0016563 A1 | 2/2002 | Hill et al. |
| 2002/0042592 A1 | 4/2002 | Wilmot et al. |
| 2002/0095120 A1 | 7/2002 | Larsen et al. |
| 2002/0111587 A1 | 8/2002 | Hommann et al. |
| 2002/0161337 A1 | 10/2002 | Shaw et al. |
| 2002/0169408 A1 | 11/2002 | Beretta et al. |
| 2002/0183690 A1 | 12/2002 | Arnisolle |
| 2003/0004466 A1 | 1/2003 | Bitdinger et al. |
| 2003/0004467 A1 | 1/2003 | Musick et al. |
| 2003/0012786 A1 | 1/2003 | Teoh et al. |
| 2003/0023205 A1 | 1/2003 | Botich et al. |
| 2003/0050606 A1 | 3/2003 | Brand et al. |
| 2003/0093036 A1 | 5/2003 | Crossman et al. |
| 2003/0105430 A1 | 6/2003 | Lavi et al. |
| 2003/0153868 A1 | 8/2003 | Azizi et al. |
| 2003/0161744 A1 | 8/2003 | Vilks et al. |
| 2003/0161828 A1 | 8/2003 | Abdelghany et al. |
| 2003/0187401 A1 | 10/2003 | Doyle |
| 2003/0206898 A1 | 11/2003 | Fischkoff et al. |
| 2003/0212362 A1 | 11/2003 | Roser |
| 2003/0219438 A1 | 11/2003 | Salfeld et al. |
| 2003/0229308 A1 | 12/2003 | Tsals et al. |
| 2003/0235585 A1 | 12/2003 | Fischkoff et al. |
| 2003/0236502 A1 | 12/2003 | De La Serna et al. |
| 2004/0009172 A1 | 1/2004 | Fischkoff et al. |
| 2004/0019326 A1 | 1/2004 | Gilbert et al. |
| 2004/0024367 A1 | 2/2004 | Gilbert |
| 2004/0033228 A1 * | 2/2004 | Krause et al. ............... 424/145.1 |
| 2004/0039336 A1 | 2/2004 | Amark et al. |
| 2004/0039337 A1 | 2/2004 | Letzing |
| 2004/0054327 A1 | 3/2004 | Gillespie |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0147875 A1 | 7/2004 | Wallace et al. |
| 2004/0151722 A1 | 8/2004 | Banerjee et al. |
| 2004/0166111 A1 | 8/2004 | Kaymakcalan et al. |
| 2004/0199117 A1 | 10/2004 | Giambattista et al. |
| 2004/0215151 A1 | 10/2004 | Marshall et al. |
| 2004/0219142 A1 | 11/2004 | Banerjee et al. |
| 2004/0225262 A1 | 11/2004 | Fathallah et al. |
| 2004/0229854 A1 | 11/2004 | Haan De |
| 2005/0020979 A1 | 1/2005 | Westbye |
| 2005/0020984 A1 | 1/2005 | Lesch, Jr. |
| 2005/0027255 A1 | 2/2005 | Lavi et al. |
| 2005/0049550 A1 | 3/2005 | Kirchhofer et al. |
| 2005/0049561 A1 | 3/2005 | Hommann et al. |
| 2005/0085776 A1 | 4/2005 | Hommann et al. |
| 2005/0090647 A1 | 4/2005 | Gatanaga et al. |
| 2005/0095208 A1 | 5/2005 | Battaglia et al. |
| 2005/0096597 A1 | 5/2005 | Crawford et al. |
| 2005/0101919 A1 | 5/2005 | Brunnberg |
| 2005/0124940 A1 | 6/2005 | Martin et al. |
| 2005/0137196 A1 | 6/2005 | Timmer et al. |
| 2005/0137534 A1 | 6/2005 | Hommann |
| 2005/0137571 A1 | 6/2005 | Hommann |
| 2005/0165360 A1 | 7/2005 | Stamp |
| 2005/0165361 A1 | 7/2005 | Marshall et al. |
| 2005/0165362 A1 | 7/2005 | Slawson |
| 2005/0165363 A1 | 7/2005 | Judson et al. |
| 2005/0171476 A1 | 8/2005 | Judson et al. |
| 2005/0171477 A1 | 8/2005 | Rubin et al. |
| 2005/0209569 A1 | 9/2005 | Ishikawa et al. |

(56) References Cited

U.S. PATENT DOCUMENTS

| | | |
|---|---|---|
| 2005/0222539 A1 | 10/2005 | Gonzales et al. |
| 2005/0222540 A1 | 10/2005 | Kirchhofer et al. |
| 2005/0261634 A1 | 11/2005 | Karlsson |
| 2005/0273054 A1 | 12/2005 | Asch |
| 2005/0273055 A1 | 12/2005 | Harrison et al. |
| 2005/0273061 A1 | 12/2005 | Hommann et al. |
| 2005/0277885 A1 | 12/2005 | Scherer |
| 2005/0277886 A1 | 12/2005 | Hommann et al. |
| 2005/0277893 A1 | 12/2005 | Liversidge |
| 2005/0288633 A1 | 12/2005 | Jeffrey |
| 2006/0009385 A1 | 1/2006 | Hoffman et al. |
| 2006/0030819 A1 | 2/2006 | Young et al. |
| 2006/0036216 A1 | 2/2006 | Rimlinger et al. |
| 2006/0047250 A1 | 3/2006 | Hickingbotham et al. |
| 2006/0069350 A1 | 3/2006 | Buenger et al. |
| 2006/0069354 A1 | 3/2006 | Buenger et al. |
| 2006/0074519 A1 | 4/2006 | Barker et al. |
| 2006/0083741 A1 | 4/2006 | Hoffman et al. |
| 2006/0100588 A1 | 5/2006 | Brunnberg et al. |
| 2006/0111666 A1 | 5/2006 | Hommann et al. |
| 2006/0111674 A1 | 5/2006 | Vedrine |
| 2006/0129122 A1 | 6/2006 | Wyrick |
| 2006/0140907 A1* | 6/2006 | Blumberg et al. ........... 424/85.6 |
| 2006/0153846 A1 | 7/2006 | Krause et al. |
| 2006/0167413 A1 | 7/2006 | Marshall et al. |
| 2006/0189933 A1 | 8/2006 | Alheidt et al. |
| 2006/0204939 A1 | 9/2006 | Bardsley et al. |
| 2006/0253083 A1 | 11/2006 | Liu |
| 2007/0041905 A1 | 2/2007 | Hoffman et al. |
| 2007/0049865 A1 | 3/2007 | Radmer et al. |
| 2007/0071747 A1 | 3/2007 | Hoffman et al. |
| 2007/0081996 A1 | 4/2007 | Hoffman et al. |
| 2007/0129674 A1 | 6/2007 | Liversidge |
| 2007/0142776 A9 | 6/2007 | Kovelman et al. |
| 2007/0161960 A1 | 7/2007 | Chen et al. |
| 2007/0197976 A1 | 8/2007 | Jacobs et al. |
| 2007/0202104 A1 | 8/2007 | Banerjee et al. |
| 2007/0239117 A1 | 10/2007 | Chelak |
| 2008/0019969 A1 | 1/2008 | Gorman |
| 2008/0097337 A1 | 4/2008 | Judd |
| 2008/0118496 A1 | 5/2008 | Medich et al. |
| 2008/0131374 A1 | 6/2008 | Medich |
| 2008/0166348 A1 | 7/2008 | Kupper et al. |
| 2008/0193466 A1 | 8/2008 | Banerjee et al. |
| 2008/0208125 A1 | 8/2008 | Bicknell et al. |
| 2008/0208140 A1 | 8/2008 | Barrelle |
| 2008/0227136 A1 | 9/2008 | Pla et al. |
| 2008/0269692 A1 | 10/2008 | James |
| 2008/0300549 A1 | 12/2008 | Verespej |
| 2008/0311043 A1 | 12/2008 | Hoffman et al. |
| 2009/0017472 A1 | 1/2009 | Stuhlmuller et al. |
| 2009/0024076 A1 | 1/2009 | Babaev |
| 2009/0024093 A1 | 1/2009 | Carrel |
| 2009/0028794 A1 | 1/2009 | Medich et al. |
| 2009/0036870 A1 | 2/2009 | Mounce et al. |
| 2009/0093792 A1 | 4/2009 | Gross et al. |
| 2009/0110679 A1 | 4/2009 | Li et al. |
| 2009/0123378 A1 | 5/2009 | Wong et al. |
| 2009/0148513 A1 | 6/2009 | Fraunhofer et al. |
| 2009/0155205 A1 | 6/2009 | Salfeld et al. |
| 2009/0157012 A1 | 6/2009 | Magne |
| 2009/0182284 A1 | 7/2009 | Morgan |
| 2009/0226530 A1 | 9/2009 | Lassner et al. |
| 2009/0239259 A1 | 9/2009 | Hsieh et al. |
| 2009/0240195 A1 | 9/2009 | Schrul et al. |
| 2009/0240210 A1 | 9/2009 | Walton |
| 2009/0258018 A1 | 10/2009 | Medich et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0299328 A1 | 12/2009 | Mudd et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0160869 A1 | 6/2010 | Liversidge |
| 2010/0160894 A1 | 6/2010 | Julian et al. |
| 2010/0278822 A1 | 11/2010 | Fraunhofer et al. |
| 2011/0002935 A1 | 1/2011 | Wan et al. |
| 2011/0054414 A1 | 3/2011 | Shang et al. |
| 2011/0171227 A1 | 7/2011 | Okun et al. |
| 2011/0178500 A1 | 7/2011 | Shang et al. |
| 2011/0300151 A1 | 12/2011 | Okun et al. |
| 2012/0107783 A1 | 5/2012 | Julian et al. |
| 2012/0233834 A1 | 9/2012 | Szechinski et al. |
| 2012/0238961 A1 | 9/2012 | Julian et al. |
| 2012/0289905 A1 | 11/2012 | Julian et al. |

FOREIGN PATENT DOCUMENTS

| | | |
|---|---|---|
| DE | 60207576 | 6/2006 |
| EP | 0068864 | 1/1983 |
| EP | 0173494 | 3/1986 |
| EP | 0184187 | 6/1986 |
| EP | 0260610 | 3/1988 |
| EP | 0154316 | 9/1989 |
| EP | 0171496 | 5/1993 |
| EP | 0401384 | 3/1996 |
| EP | 0125023 | 3/2002 |
| EP | 1334740 | 8/2003 |
| EP | 1364667 | 11/2003 |
| EP | 1523360 | 4/2005 |
| EP | 2067496 | 6/2009 |
| EP | 2085104 | 8/2009 |
| EP | 2361648 | 8/2011 |
| GB | 2243552 | 11/1991 |
| GB | 2388033 | 11/2003 |
| GB | 2465389 | 5/2010 |
| JP | 50-14835 | 5/1975 |
| JP | 5-161712 | 6/1993 |
| JP | 2001-508648 A | 3/2001 |
| JP | 2001-512038 | 8/2001 |
| JP | 2006-507060 A | 2/2006 |
| RU | 2004256 | 12/1993 |
| RU | 2069584 | 11/1996 |
| RU | 2131748 | 6/1999 |
| RU | 2169584 | 6/2001 |
| WO | WO 86/01533 | 3/1986 |
| WO | WO 87/02671 | 5/1987 |
| WO | WO 90/01047 | 2/1990 |
| WO | WO 90/07861 | 7/1990 |
| WO | WO 91/03553 | 3/1991 |
| WO | WO 91/17271 | 11/1991 |
| WO | WO 92/01047 | 1/1992 |
| WO | WO 92/09690 | 6/1992 |
| WO | WO 92/15679 | 9/1992 |
| WO | WO 92/18619 | 10/1992 |
| WO | WO 92/20791 | 11/1992 |
| WO | WO 93/01288 | 1/1993 |
| WO | WO 93/06213 | 4/1993 |
| WO | WO 93/13819 A1 | 7/1993 |
| WO | WO 93/19751 | 10/1993 |
| WO | WO 94/06476 | 3/1994 |
| WO | WO 94/08609 | 4/1994 |
| WO | WO 94/09839 A1 | 5/1994 |
| WO | WO 94/13342 A1 | 6/1994 |
| WO | WO 94/26333 A1 | 11/1994 |
| WO | WO 97/29131 | 8/1997 |
| WO | WO 99/22789 A1 | 5/1999 |
| WO | WO 99/22792 A1 | 5/1999 |
| WO | WO 01/37908 A1 | 5/2001 |
| WO | WO 01/62319 A2 | 8/2001 |
| WO | WO 02/12502 | 2/2002 |
| WO | WO 02/072636 | 9/2002 |
| WO | WO 03/039433 | 5/2003 |
| WO | WO 03/039633 A2 | 5/2003 |
| WO | WO 03/077968 A2 | 9/2003 |
| WO | WO 03/097133 A1 | 11/2003 |
| WO | WO 03/099358 | 12/2003 |
| WO | WO 04/000397 | 12/2003 |

(56) References Cited

FOREIGN PATENT DOCUMENTS

| WO | WO03099358 | 12/2003 |
|---|---|---|
| WO | WO 2004/016286 | 2/2004 |
| WO | WO 2004/024211 | 3/2004 |
| WO | WO 2004/060451 A1 | 7/2004 |
| WO | WO 2004/067068 A1 | 8/2004 |
| WO | WO 2005/002653 | 1/2005 |
| WO | WO 2005/046765 A2 | 5/2005 |
| WO | WO 2005/079889 A1 | 9/2005 |
| WO | WO 2005/090836 | 9/2005 |
| WO | WO 2005/113039 A1 | 12/2005 |
| WO | WO 2005/115508 A1 | 12/2005 |
| WO | WO 2005/115509 | 12/2005 |
| WO | WO 2005/115509 A1 | 12/2005 |
| WO | WO 2005/115510 A1 | 12/2005 |
| WO | WO 2005/115511 A1 | 12/2005 |
| WO | WO 2005/115512 A1 | 12/2005 |
| WO | WO 2005/115513 A1 | 12/2005 |
| WO | WO 2005/115516 A1 | 12/2005 |
| WO | WO2005115508 | 12/2005 |
| WO | WO 2006/000785 | 1/2006 |
| WO | WO 2006/050861 A1 | 6/2006 |
| WO | WO 2006/063015 | 6/2006 |
| WO | WO 2008/005315 | 1/2008 |
| WO | WO 2009/040603 | 4/2009 |
| WO | WO 2009/155277 | 12/2009 |
| WO | WO 2010/029054 | 3/2010 |
| WO | WO 2011/014514 | 2/2011 |
| WO | WO 2011/014704 | 2/2011 |

OTHER PUBLICATIONS

Mar. 6, 2000 correspondence from Dept. of Health & Human Services, Food and Drug Administration to Robert Shaw/Owen Mumford, Inc. regarding Section 501(k) notification of intent to market device.
Owen Mumford drawing/schematic of the Abbot-Plunger AUTOject Mini dated Mar. 25, 2002, Drawing No. P02 207.
Owen Mumford drawing/schematic of the Plunger—Miniject dated Mar. 30, 1993, Drawing No. P93.022.
Owen Mumford drawing/schematic of the Plunger—Miniject dated Mar. 30. 1993, Drawing No. AJ 358.
Owen Mumford drawing/schematic of the Plunger—Autoject Mini dated May 9, 1997, Drawing No. AJ 654.
Alexander et al., "Elevated levels of proinflammatory cytokines in the semen of patients with chronic prostatitis/chronic pelvic pain syndrome," Urology 52:744 (1998).
Gurevicius et al., "Contribution of nitric oxide to coronary vasodilation during hypercapnic acidosis," Amer. J. Physiol.—Heart and Circulatory Physiology, vol. 268, pp. 37-42 (1995).
Arend et al., "Inhibition of the production and effects of interleukin-1 and tumor necrosis factor α in rheumatoid arthritis," Arthritis & Rheumatism 38:151-160 (1995).
Sewell et al., "DAB IL-2 fusion toxin in refractory rheumatoid arthritis," Arthritis & Rheumatism, vol. 36, 1223 (1993).
Arthritis & Rheumatism, vol. 38, S185 (1995).
Arthritis & Rheumatism, vol. 39, No. 9 (supplement), S120 (1996).
Asakawa et al., "Effects of cernitin pollen-extract on inflammatory cytokines in sex-hormone-induced nonbacterial prostatitis rates," Hinyokika Kiyo 47:459 (2001).
Ausubel, F.M. et al. (eds), Current Protocols in Molecular Biology, Greene Publishing Associates (1989).
Barbas et al., "Assembly of combinatorial antibody libraries on phage surfaces: The gene III site," Proc. Natl. Acad. Sci. USA 88: 7978-7982 (1991).
Beidler et al., "Cloning and high level expression of a chimeric antibody with specificity for human carcinoembrynic antigen," J. Immunol. 141: 4056-4060 (1988).
Better et al., "*Escherichia coli* secretion of an active chimeric antibody fragment," Science 240: 1041-1043 (1988).
Bird et al., "Single-chain antigen-binding proteins," Science 242: 423-426 (1988).

Boss et al., "Genetically engineered antibodies," Immunology Today 6: 12-13 (1985).
Braun et al., "Low secretion of tumor necrosis factor α, but no other Th1 or Th2 cytokines, by peripheral blood mononuclear cells correlates with chronicity in reactive arthritis," Arthritis Rheum. 42(10): 2039 (1999).
Brisby et al., "Proinflammatory cytokines in cerebrospinal fluid and serum in patients with disc herniation and sciatica," Eur. Spine J. 11: 62 (2002).
Canfield et al., "The binding affinity of human IgG for its high affinity Fc receptor is determined by multiple amino acids in the Cg2 domain and is modulated by the hinge region," J. Exp. Med. 173: 1483-1491 (1991).
Clackson et al., "Making antibody fragments using phage display libraries," Nature 352: 624-628 (1991).
Cox et al., "A Directory of Human Germ-line V78 Segments Reveals a Strong Bias in their Usage," Eur. J. Immunol. 24: 827-836 (1994).
Davis et al., "Structure of human tumor necrosis factor α derived from recombinant DNA," Biochemistry 26: 1322-1326 (1987).
Duffy et al., "Effect of nimesulide on Cox-1 and Cox-2 expression and related prostanoid formation in patients with acute knee inflammation," ACR 66th Annual Scientific Meeting, abstract (2002).
Eisermann et al., "Tumor necrosis factor in peritoneal fluid of women undergoing laparoscopic surgery," Fertil. Steril. 50:573 (1988).
Elliot et al., "Randomised double-blind comparison of chimeric monoclonal antibody to tumor necrosis factor α versus placebo in rheumatoid arthritis," Lancet 344: 1105-1110 (1994).
Elliot et al., "Repeated therapy with monoclonal antibody to tumour necrosis factor α in patients with rheumatoid arthritis," Lancet 344: 1125-1127 (1994).
Fava et al., "Critical role of peripheral blood phagocytes and the involvement of complement in tumour necrosis factor enhancement of passive collagen-arthritis," Clin. Exp. Immunol. 94:261-266 (1993).
Francis, "Protein modification and fusion proteins," Focus on Growth Factors 3: 4-10 (1992).
Fredriksson et al., "Severe psoriasis—oral therapy with a new retinoid," Dermatologica 157: 238 (1978).
Fuchs et al., "Targeting recombinant antibodies to the surface of *Escherichia coli*," Bio/Technology 9: 1370-1372 (1991).
Garrard et al., "FAB assembly and enrichment in a monovalent phage display system," Bio/Technology 9: 1373-1377 (1991).
Goeddel, Gene Expression Technology: Methods in Enzymology 185, Academic Press, San Diego, CA (1990).
Gram et al., "In vitro selection and affinity maturation of antibodies from a naïve combinatorial immunoglobulin library," Proc. Natl. Acad. Sci. US 89: 3576-3580 (1992).
Greaves et al., "Treatment of psoriasis," N. Eng. J. Med. 332: 581 (1995).
Griffiths et al., "Human anti-self antibodies with high specificity from phage display libraries," EMBO J 12: 725-734 (1993).
Grom et al., "Patterns of expression of tumor necrosis factor α, tumor necrosis factor β, and their receptors in synovia of patients with juvenile rheumatoid arthritis and juvenile spondylarthropathy," Arthritis Rheum. 39: 1703 (1996).
Halme, "Release of tumor necrosis factor-α by human peritoneal macrophages in vivo and in vitro," Am. J. Obstet. Gynecol. 161:1718 (1989).
Harris et al., "Expression of proinflammatory genes during estrogen-induced inflammation of the rat prostrate," Prostate 44:25 (2000).
Hawkins et al., "Selection of phage antibodies by binding affinity," J. Mol. Biol. 226: 889-896 (1992).
Hay et al., "Bactriophage cloning and *Escherichia coli* expression of a human IgM Fab," Hum. Antibod. Hybridomas 3: 81-85 (1992).
Hollinger et al., "Diabodies: small bivalent and bispecific antibody fragments," Proc. Natl. Acad. Sci. USA 90: 6444-6448 (1993).
Hoogenboom et al., "Multi-subunit proteins on the surface of filamentous phage," Nuc. Acid. Res. 19: 4133-4137 (1991).
Huset et al., "Generation of a large combinatorial library of the immunoglobulin repertoire in phage lambda," Science 246: 1275-1281 (1989).
Huskisson, "Measurement of pain," Lancet 304: 1127-1131 (1974).

(56) References Cited

OTHER PUBLICATIONS

Huston et al., "Protein engineering of antibody binding sites," Proc. Natl. Acad. Sci. USA 85: 5879-5883 (1988).
Jones et al., "Replacing the complementarity-determining regions in a human antibody with those from a mouse," Nature 321: 552-525 (1986).
Jones et al., "Structure of tumour necrosis factor," Nature 338: 225-228 (1989).
Johnsson et al., "Immobilization of proteins to a carboxymethyldextran-modified bold surface for biospecific interaction analysis in surface plasmon resonance sensors," Anal. Biochem. 198: 268 (1991).
Johnsson et al., "Comparison of methods for immobilization to carboxymethyl dextran sensor surfaces by analysis of the specific activity of monoclonal antibodies," J. Mol. Recognit. 8: 125 (1995).
Jonsson et al., "Real-time biospecific interaction analysis using surface plasmon resonance and a sensor chip technology," Biotechniques 11: 620-627 (1991).
Jonsson et al., "Introducing a biosensor based technology for real-time biospecific interaction analysis," Ann. Biol. Clin. 51: 19 (1992).
Jorgensen et al., "Pain assessment of subcutaneous injections," Annals of Pharmacotherapy 30: 729-732 (1996).
Kabat et al., Sequences of Proteins of Immunological Interest, Fifth Edition, U.S. Department of Health and Human Services, NIH Publication No. 91-3242 (1991).
Kaijtzel et al., "Polymorphism within the tumor necrosis factor α promoter region in patients with ankylosing spodylitis," Hum. Immunol. 60: 140 (1999).
Kaufman et al., "Amplification and expression of sequences contransfected with a modular dihydrofolate reductase complementary DNA gene," Mol. Biol. 159: 601-621 (1982).
Koski et al., "Tumor necrosis factor-alpha and receptors for it in labial salivary glands in Sjogren's syndrome," Clin. Exp. Rheumatol. 19: 131 (2001).
Liu et al., "Production of a mouse-human chimeric monoclonal antibody to CD20 with potent Fc-dependent biologic activity," J. Immunol. 139: 3521-3526 (1987).
Liu et al., "Chimeric mouse-human IgG1 antibody that can mediate lysis of cancer cells," J. Immunol. 84: 3439-3443 (1987).
Lund et al., "Human FcRI and FcRII interact with distinct but overlapping sites on human IgG," J. of Immunol. 147: 2657-2662 (1991).
MacDonald et al., "Tumour necrosis factor-alpha and interferon-gamma production measured at the single cell level in normal and inflamed human intestine," Clin. Exp. Immunol. 81:301 (1990).
Mackiewicz et al., "Dual effects of caspase-1, interleukin-1β, tumour necrosis factor-α and nerve growth factor receptor in inflammatory myopathies," Clin. Exp. Rheumatol. 21:41 (2003).
Mangge et al., "Serum cytokines in juvenile rheumatoid arthritis," Arthritis Rheum. 8: 211 (1995).
Marks et al., "Assessment of disease progress in psoriasis," Arch. Dermatol. 125: 235 (1989).
McCafferty et al., "Phase antibodies," Nature 348: 552-554 (1990).
Moeller et al., "Monoclonal antibodies to human tumor necrosis factor α," Cytokine 2: 162169 (1990).
Mori et al., "Peritoneal fluid interleukin-1β and tumor necrosis in patients with benign gynecologic disease," Am. J. Reprod. Immunol. 26:62 (1991).
Morrison, "Transfectomas provide novel chimeric antibodies," Science 229: 1202-1207 (1985).
Murota et al., "Disruption of tumor necrosis factor receptor p55 impairs collagen turnover in experimentally induced sclerodermic skin fibroblasts," Arthritis Rheum. 48: 1117 (2003).
Nadler et al., "IL-1β and TNF-α in prostatic secretions are indicators in the evaluation of men with chronic prostatitis," J. Urol. 164:214 (2000).
Nishimura et al., "Recombinant human-mouse chimeric monoclonal antibody specific for common acute lymphocyte leukemia antigen," Cancer Res. 47: 999-1005 (1987).

Oh H. et al., "The potential angiogenic role of macrophages in the formation of choroidal neovascular membranes," Invest. Ophthalmol. Vis. Sci 40:1891 (1999).
Oi et al., "Chimeric antibodies," BioTechniques 4:214 (1986).
Orhan et al., "Seminal plasma cytokine levels in the diagnosis of chronic pelvic pain syndrome," Int. J. Urol. 8:495 (2001).
Overton et al., "Peritoneal fluid cytokines and the relationship with endometriosis and pain," Hum. Reprod. 11:380 (1996).
Ozaktay et al., "Dorsal root sensitivity to interleukin-1 beta, interleukin-6 and tumor necrosis factor in rats," Eur. Spine J. 11: 467 (2002).
Partsch et al., "T cell derived cytokines in psoriatic arthritis synovial fluids," Ann. Rheum. Dis. 57: 691 (1998).
Pennica et al., "Human tumour necrosis factor," Nature 312: 724-729 (1984).
Poljak et al., "Production and structure of diabodies," Structure 2: 1121-1123 (1994).
Queen et al., "A humanized antibody that binds to the interleukin 2 receptor," Proc. Natl. Acad. Sci. USA 86: 10029-10033 (1989).
Rankin et al., "The therapeutic effects of an engineered human anti-tumour necrosis factor alpha antibody in rheumatoid arthritis," Br. J. Rheumatol. 34: 334-342 (1995).
Reuss-Borst et al., "Sweet's syndrome associated with myelodysplasia," Br. J. Haematol. 84: 356 (1993).
Ritchlin et al., "Patterns of cytokine production in psoriatic synovium," J. Rheumatol. 25: 1544 (1998).
Sambrook, Fritsch and Maniatis (eds), Molecular Cloning: A Laboratory Manual, Second Edition, Cold Spring Harbor, N.Y. (1989).
Schwartzman et al., "Does route of administration affect the outcome of TNF antagonist theraphy?" Arthritis Research & Therapy 6(Suppl 2): S19-S23 (2004).
Shaw et al., "Mouse/human chimeric antibodies to a tumor-associated antigen," J. Natl. Cancer Inst. 80: 1553-1559 (1988).
Shvidel et al., "Cytokine release by activated T-cells in large granular lymphocytic leukemia associated with autoimmune disorders," Hematol. J. 3:32 (2002).
Sklavounou et al., "TNF-α and apoptosis-regulating proteins in oral lichen planus," J. Oral. Pathol. Med. 29: 370 (2000).
Studnicka-Benke et al., "Tumour necrosis factor alpha and its soluble receptors parallel clinical disease and autoimmune activity in systemic lupus erythematosus," Br. J. Rheumatol. 35:1067 (1996).
Sun et al., "Bowel necrosis induced by tumor necrosis factor in rats is mediated by platelet-activating factor," J. Clin. Invest. 81:1328 (1988).
Sun et al., "Chimeric antibody with human constant regions and mouse variable regions directed against carcinoma-associated antigen 17-1A," Proc. Natl. Acad. Sci. USA 84: 214-218 (1987).
Takematsu et al., "Absence of tumor necrosis factor-α in suction blister fluids and stratum corneum from patients with psoriasis," Arch. Dermatol. Res. 281: 398 (1989).
Taketani et al., "Comparison of cytokine levels and embryo toxicity in peritoneal fluid in infertile women with untreated or treated endometriosis," Am. J. Obstet. Gynecol. 167:265 (1992).
Taurog et al., The Spondylarthritides, Oxford: Oxford University Press (1998).
Taylor et al., "A transgenic mouse that expresses a diversity of human sequence heavy and light chain immunoglobulins," Nucl. Acids Res. 20: 6287 (1992).
Tomlinson et al., "The Repertoire of Human Germline VH Sequences Reveals About Fifty Groups of VH Segments with Different Hypervariable Loops," J. Mol. Biol. 227: 776-798 (1992).
Tracy et al., "Shock and tissue injury induced by recombinant human cachectin," Science 234:470 (1986).
Tsutsumimoto et al., "TNF-α and IL-1β suppress N-Cadherin expression in MC3T3-E1 cells," J. Bone Miner. Res. 14: 1751 (1999).
Tutuncu et al., "Anti-TNF therapy for other inflammatory conditions," Clin. Exp. Rheumatol. 20(6 Suppl 28): S146 (2002).
Urlaub et al., "Isolation of Chinese hamster cell mutants deficient in dihydrofolate reductase activity," Proc. Natl. Acad. Sci. USA 77: 4216-4220 (1980).
van Dulleman et al., "Treatment of Crohn's disease with anti-tumor necrosis factor chimeric monoclonal antibody," Gastroenterology 109:129 (1995).

(56) References Cited

OTHER PUBLICATIONS

Venn et al., "Elevated synovial fluid levels of interleukin-6 and tumor necrosis factor associated with early experimental canine osteoarthritis," Arthritis and Rheum. 36: 819 (1993).
Verhoeyan et al., "Reshaping human antibodies," Science 239: 1534 (1988).
Verjans et al., "Restriction fragment length polymorphism of the tumor necrosis factor region in patients with ankylosing spodylitis," Arthritis Rheum. 34: 486 (1991).
Verjans et al., "Polymorphism of tumour necrosis factor-alpha at position—308 in relation to ankylosing spondylitis," Clin. Exp. Immunol. 97: 45 (1994).
Victor et al., "TNF-alpha and apoptosis," J. Drugs Dermatol. 1: 264 (2002).
Wakefield et al., "The role of cytokines in the pathogenesis of inflammatory eye disease," Cytokine 4:1 (1992).
Ward et al., "Binding activities of a repertoire of single immunoglobulin variable domains secreted from *Escherichia coli*," Nature 341: 544-546 (1989).
Wood et al., "The synthesis and in vivo assembly of functional antibodies in yeast," Nature 314: 446-449 (1985).
Woon et al., "Kinetics of cytokine production in experimental autoimmune anterior uveitis," Curr. Eye Res. 17: 955 (1998).
Zeidler et al., "Undifferentiated spodyloarthropathies," Rheum. Dis. Clin. North Am. 18: 187 (1992).
Arthritis & Rheumatism, vol. 39, No. 9, S282 (1996).
Arthritis & Rheumatism, vol. 39, No. 9, S284 (1996).
Arthritis & Rheumatism, vol. 39, No. 9, S296 (1996).
Arthritis & Rheumatism, vol. 39, No. 9, S308 (1996).
Arthritis & Rheumatism, vol. 39, No. 9, S81 (1996).
Arthritis & Rheumatism, vol. 39, No. 9, S82 (1996).
Communication pursuant to Article 94(3) EPC issued by the European Patent Office in European Application No. 05758156.3-2320, dated Jan. 18, 2011.
Communication of a Notice of Opposition issued in European Application No. 04822031.3-1526, dated Jan. 6, 2010.
Communication pursuant to Article 96(2) EPC issued in European Application No. 04822031.3-1526, dated May 31, 2007.
Communication under Rule 112 EPC issued in European Application No. 04822031.3, dated Mar. 13, 2007.
International Search Report issued in International Application No. PCT/GB2005/002487, dated Aug. 19, 2005.
Written Opinion issued in International Application No. PCT/GB2005/002487, dated Dec. 23, 2006.
International Preliminary Report on Patentability issued in International Application No. PCT/GB2005/002487, dated Sep. 7, 2006.
International Search Report issued in International Application No. PCT/US2011/033504, dated Jul. 8, 2011.
Written Opinion issued in International Application No. PCT/US2011/033504, dated Jul. 8, 2011.
International Search Report issued in International Application No. PCT/US2007/015095, dated Sep. 11, 2008.
Written Opinion issued in International Application No. PCT/US2007/015095, dated Sep. 11, 2008.
International Preliminary Report on Patentability issued in International Application No. PCT/US2007/015095, dated Jun. 19, 2009.
International Search Report issued in International Application No. PCT/US2010/033012, dated Jul. 2, 2010.
Written Opinion issued in International Application No. PCT/US2010/033012, dated Jul. 2, 2010.
International Search Report issued in International Application No. PCT/US2010/060496, dated Feb. 16, 2011.
Written Opinion issued in International Application No. PCT/US2010/060496, dated Feb. 16, 2011.
International Search Report issued in International Application No. PCT/US2004/013278, dated May 30, 2005.
Written Opinion issued in International Application No. PCT/US2004/013278, dated Oct. 29, 2006.
International Preliminary Report on Patentability issued in International Application No. PCT/US2004/013278, dated Nov. 1, 2006.
Office Action issued in Russian Application No. 2006145501/14(049694), dated May 21, 2009.
Decision on Grant issued in Russian Application No. 2006145501/14(049694), dated Nov. 2, 2009.
Decision on Grant issued in Russian Application No. 2009102986/14(003862), dated Jun. 30, 2011.
Notice of Reasons for Rejection issued in Japanese Application No. 2007-517459, dated Aug. 24, 2010.
Notice of Reasons for Rejection issued in Japanese Application No. 2007-517459, dated Mar. 8, 2011.
Office Action issued in Mexican Application No. PA/a/2006/015056, dated Jul. 28, 2010.
Office Action issued in Mexican Application No. PA/a/2006/015056, dated Apr. 1, 2011.
Reexamination Decision issued in Chinese Application No. 200580020958.6, dated Jun. 13, 2011.
Notification of Reexamination issued in Chinese Application No. 200580020958.6, dated Aug. 17, 2010.
Rejection Decision issued in Chinese Application No. 200580020958.6, dated Jun. 5, 2009.
Office Action issued in Chinese Application No. 200580020958.6, dated Sep. 5, 2008.
Office Action issued in Australian Application No. 2005256832, dated Apr. 18, 2011.
Office Action issued in Australian Application No. 2005256832, dated Feb. 22, 2010.
Examination Report issued in New Zealand Application No. 552340, dated Apr. 27, 2009.
Examination Report issued in New Zealand Application No. 552340, dated Aug. 12, 2010.
BD Preventis, Shielding System for Prefilled Syringes, http://www.bd.com/pharmaceuticals/products/safety-engineered.asp, last accessed Aug. 26, 2010.
"Abbott Receives FDA Approval for New Humira Delivery Device," Press Release, dated Jun. 26, 2006 (color).
Notification of Provisional Rejection issued in Korean Application No. 10-2006-7026814, dated Jul. 19, 2011.
Office Action issued in Canadian Application No. 2,571,571, dated Oct. 24, 2011.
Office Action issued in Chinese Application No. 201010576413.6, dated Nov. 2, 2011.
International Preliminary Report on Patentability issued in International Application No. PCT/US2010/033012, dated Nov. 1, 2011.
Decision of Final Rejection issued in Japanese Application No. 2007-517459, dated Jan. 10, 2012.
Notice of Rejection issued in Japanese Application No. 2009-518284, dated May 29, 2012.
Examination Report issued in Australian Application No. 2007269791, dated Jul. 30, 2012.
Notice of Rejection issued in Japanese Application No. 2011-196424, dated Jan. 29, 2013.
Invitation to Pay Additional Fees issued in International Application No. PCT/US2012/034683, dated Nov. 7, 2012.
Examination Report issued in New Zealand Application No. 595605, dated Apr. 12, 2013.
Office Action issued in Chinese Application No. 2010105764136, dated Jul. 31, 2012.
International Search Report and Written Opinion issued in International Application No. PCT/US2012/029682, dated Jul. 27, 2012.
International Search Report and Written Opinion issued in International Application No. PCT/US2012/022432, dated Apr. 18, 2012.
International Search Report issued in International Application No. PCT/US2012/022433, dated Jul. 5, 2012.
Written Opinion issued in International Application No. PCT/US2012/022433, dated Jul. 5, 2012.

* cited by examiner

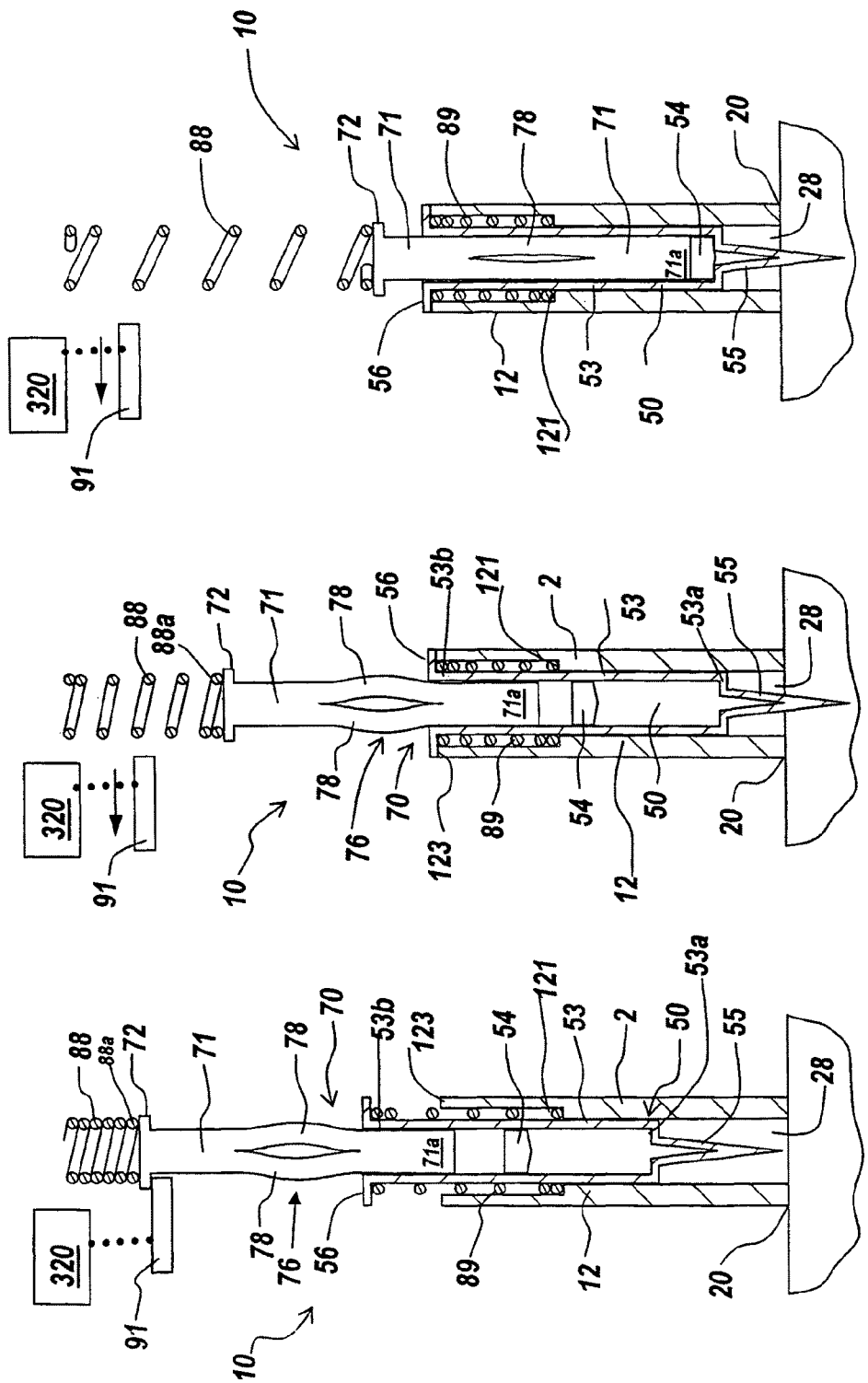

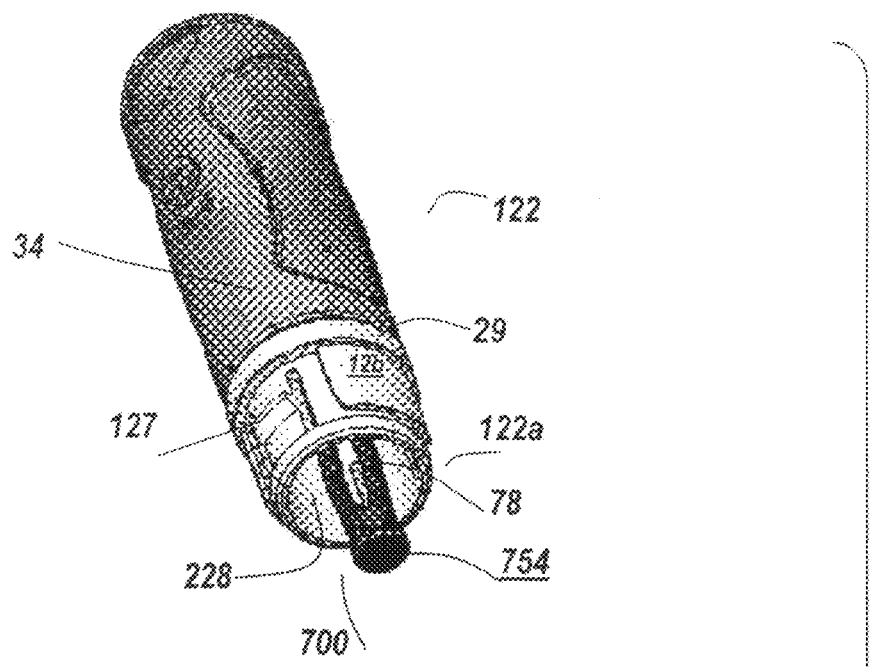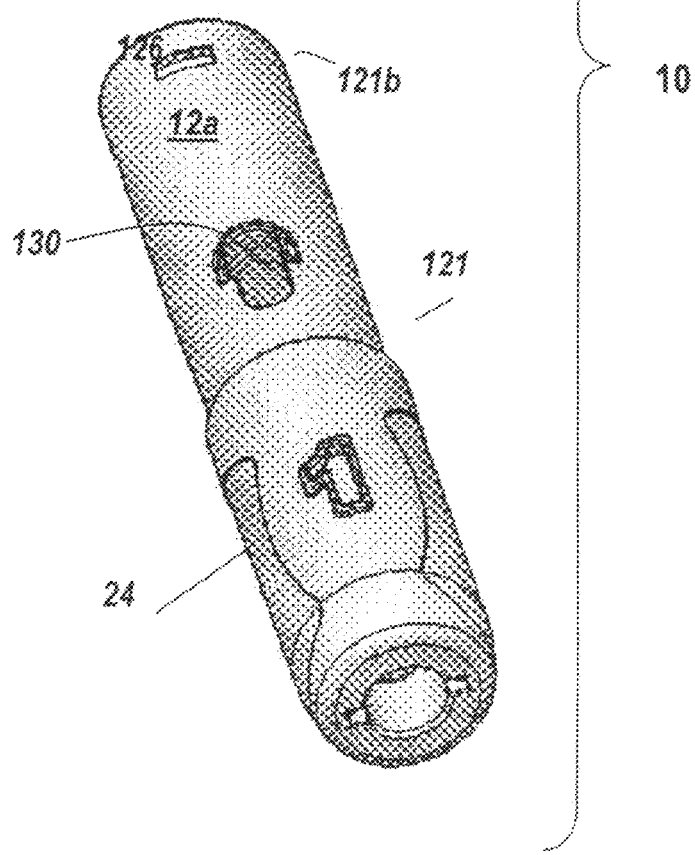
Fig. 6

SEQUENCE LISTING

```
<160> NUMBER OF SEQ ID NOS: 37

<210> SEQ ID NO 1
<211> LENGTH: 107
<212> TYPE: PRT
<213> ORGANISM: Artificial Sequence
<220> FEATURE:
<223> OTHER INFORMATION: adalimumab light chain variable region

<400> SEQUENCE: 1

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: adalimumab heavy chain variable region

<400> SEQUENCE: 2

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45
```

```
Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
            115                 120

<210> SEQ ID NO 3
<211> LENGTH: 9
<212> TYPE: PRT
<213> ORGANISM: Artificial Sequence
<220> FEATURE:
<223> OTHER INFORMATION: adalimumab light chain variable region CDR3
<221> NAME/KEY: VARIANT
<222> LOCATION: 9
<223> OTHER INFORMATION: Xaa = Thr or Ala

<400> SEQUENCE: 3

Gln Arg Tyr Asn Arg Ala Pro Tyr Xaa
 1               5

<210> SEQ ID NO 4
<211> LENGTH: 12
<212> TYPE: PRT
<213> ORGANISM: Artificial Sequence
<220> FEATURE:
<223> OTHER INFORMATION: adalimumab heavy chain variable region CDR3
<221> NAME/KEY: VARIANT
<222> LOCATION: 12
<223> OTHER INFORMATION: Xaa = Tyr or Asn

<400> SEQUENCE: 4

Val Ser Tyr Leu Ser Thr Ala Ser Ser Leu Asp Xaa
 1               5                  10

<210> SEQ ID NO 5
<211> LENGTH: 7
<212> TYPE: PRT
<213> ORGANISM: Artificial Sequence
<220> FEATURE:
<223> OTHER INFORMATION: adalimumab light chain variable region CDR2

<400> SEQUENCE: 5

Ala Ala Ser Thr Leu Gln Ser
 1               5

<210> SEQ ID NO 6
<211> LENGTH: 17
<212> TYPE: PRT
<213> ORGANISM: Artificial Sequence
<220> FEATURE:
<223> OTHER INFORMATION: adalimumab heavy chain variable region CDR2

<400> SEQUENCE: 6

Ala Ile Thr Trp Asn Ser Gly His Ile Asp Tyr Ala Asp Ser Val Glu
 1               5                  10                  15

Gly

<210> SEQ ID NO 7
<211> LENGTH: 11
<212> TYPE: PRT
<213> ORGANISM: Artificial Sequence
```

```
<220> FEATURE:
<223> OTHER INFORMATION: adalimumab light chain variable region CDR1

<400> SEQUENCE: 7

Arg Ala Ser Gln Gly Ile Arg Asn Tyr Leu Ala
1               5                   10

<210> SEQ ID NO 8
<211> LENGTH: 5
<212> TYPE: PRT
<213> ORGANISM: Artificial Sequence
<220> FEATURE:
<223> OTHER INFORMATION: adalimumab heavy chain variable region CDR1

<400> SEQUENCE: 8

Asp Tyr Ala Met His
1               5

<210> SEQ ID NO 9
<211> LENGTH: 107
<212> TYPE: PRT
<213> ORGANISM: Artificial Sequence
<220> FEATURE:
<223> OTHER INFORMATION: 2SD4 light chain variable region

<400> SEQUENCE: 9

Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Ala Phe Gly Gln Gly Thr Lys Val Glu Ile Lys
            100                 105

<210> SEQ ID NO 10
<211> LENGTH: 121
<212> TYPE: PRT
<213> ORGANISM: Artificial Sequence
<220> FEATURE:
<223> OTHER INFORMATION: 2SD4 heavy chain variable region

<400> SEQUENCE: 10

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Asp Trp Val
        35                  40                  45

Ser Ala Ile Thr Trp Asn Ser Gly His Ile Asp Tyr Ala Asp Ser Val
    50                  55                  60

Glu Gly Arg Phe Ala Val Ser Arg Asp Asn Ala Lys Asn Ala Leu Tyr
65                  70                  75                  80

Leu Gln Met Asn Ser Leu Arg Pro Glu Asp Thr Ala Val Tyr Tyr Cys
                85                  90                  95
```

```
Thr Lys Ala Ser Tyr Leu Ser Thr Ser Ser Leu Asp Asn Trp Gly
            100                 105                 110

Gln Gly Thr Leu Val Thr Val Ser Ser
        115                 120

<210> SEQ ID NO 11
<211> LENGTH: 9
<212> TYPE: PRT
<213> ORGANISM: Artificial Sequence
<220> FEATURE:
<223> OTHER INFORMATION: 2SD4 light chain variable region CDR3

<400> SEQUENCE: 11

Gln Lys Tyr Asn Ser Ala Pro Tyr Ala
1               5

<210> SEQ ID NO 12
<211> LENGTH: 9
<212> TYPE: PRT
<213> ORGANISM: Artificial Sequence
<220> FEATURE:
<223> OTHER INFORMATION: EP B12  light chain variable region CDR3

<400> SEQUENCE: 12

Gln Lys Tyr Asn Arg Ala Pro Tyr Ala
1               5

<210> SEQ ID NO 13
<211> LENGTH: 9
<212> TYPE: PRT
<213> ORGANISM: Artificial Sequence
<220> FEATURE:
<223> OTHER INFORMATION: VL10E4 light chain variable region CDR3

<400> SEQUENCE: 13

Gln Lys Tyr Gln Arg Ala Pro Tyr Thr
1               5

<210> SEQ ID NO 14
<211> LENGTH: 9
<212> TYPE: PRT
<213> ORGANISM: Artificial Sequence
<220> FEATURE:
<223> OTHER INFORMATION: VL100A9 light chain variable region CDR3

<400> SEQUENCE: 14

Gln Lys Tyr Ser Ser Ala Pro Tyr Thr
1               5

<210> SEQ ID NO 15
<211> LENGTH: 9
<212> TYPE: PRT
<213> ORGANISM: Artificial Sequence
<220> FEATURE:
<223> OTHER INFORMATION: VLL100D2 light chain variable region CDR3

<400> SEQUENCE: 15

Gln Lys Tyr Asn Ser Ala Pro Tyr Thr
1               5

<210> SEQ ID NO 16
<211> LENGTH: 9
<212> TYPE: PRT
<213> ORGANISM: Artificial Sequence
<220> FEATURE:
<223> OTHER INFORMATION: VLL0F4 light chain variable region CDR3

<400> SEQUENCE: 16
```

Gln Lys Tyr Asn Arg Ala Pro Tyr Thr
1               5

<210> SEQ ID NO 17
<211> LENGTH: 9
<212> TYPE: PRT
<213> ORGANISM: Artificial Sequence
<220> FEATURE:
<223> OTHER INFORMATION: LOE5 light chain variable region CDR3

<400> SEQUENCE: 17

Gln Lys Tyr Asn Ser Ala Pro Tyr Tyr
1               5

<210> SEQ ID NO 18
<211> LENGTH: 9
<212> TYPE: PRT
<213> ORGANISM: Artificial Sequence
<220> FEATURE:
<223> OTHER INFORMATION: VLLOG7 light chain variable region CDR3

<400> SEQUENCE: 18

Gln Lys Tyr Asn Ser Ala Pro Tyr Asn
1               5

<210> SEQ ID NO 19
<211> LENGTH: 9
<212> TYPE: PRT
<213> ORGANISM: Artificial Sequence
<220> FEATURE:
<223> OTHER INFORMATION: VLLOG9 light chain variable region CDR3

<400> SEQUENCE: 19

Gln Lys Tyr Thr Ser Ala Pro Tyr Thr
1               5

<210> SEQ ID NO 20
<211> LENGTH: 9
<212> TYPE: PRT
<213> ORGANISM: Artificial Sequence
<220> FEATURE:
<223> OTHER INFORMATION: VLLOH1 light chain variable region CDR3

<400> SEQUENCE: 20

Gln Lys Tyr Asn Arg Ala Pro Tyr Asn
1               5

<210> SEQ ID NO 21
<211> LENGTH: 9
<212> TYPE: PRT
<213> ORGANISM: Artificial Sequence
<220> FEATURE:
<223> OTHER INFORMATION: VLLOH10 light chain variable region CDR3

<400> SEQUENCE: 21

Gln Lys Tyr Asn Ser Ala Ala Tyr Ser
1               5

<210> SEQ ID NO 22
<211> LENGTH: 9
<212> TYPE: PRT
<213> ORGANISM: Artificial Sequence
<220> FEATURE:
<223> OTHER INFORMATION: VL1B7 light chain variable region CDR3

<400> SEQUENCE: 22

Gln Gln Tyr Asn Ser Ala Pro Asp Thr

<210> SEQ ID NO 23
<211> LENGTH: 9
<212> TYPE: PRT
<213> ORGANISM: Artificial Sequence
<220> FEATURE:
<223> OTHER INFORMATION: VL1C1 light chain variable region CDR3

<400> SEQUENCE: 23

Gln Lys Tyr Asn Ser Asp Pro Tyr Thr
1               5

<210> SEQ ID NO 24
<211> LENGTH: 9
<212> TYPE: PRT
<213> ORGANISM: Artificial Sequence
<220> FEATURE:
<223> OTHER INFORMATION: VL0.1F4 light chain variable region CDR3

<400> SEQUENCE: 24

Gln Lys Tyr Ile Ser Ala Pro Tyr Thr
1               5

<210> SEQ ID NO 25
<211> LENGTH: 9
<212> TYPE: PRT
<213> ORGANISM: Artificial Sequence
<220> FEATURE:
<223> OTHER INFORMATION: VL0.1H8 light chain variable region CDR3

<400> SEQUENCE: 25

Gln Lys Tyr Asn Arg Pro Pro Tyr Thr
1               5

<210> SEQ ID NO 26
<211> LENGTH: 9
<212> TYPE: PRT
<213> ORGANISM: Artificial Sequence
<220> FEATURE:
<223> OTHER INFORMATION: LOE7.A light chain variable region CDR3

<400> SEQUENCE: 26

Gln Arg Tyr Asn Arg Ala Pro Tyr Ala
1               5

<210> SEQ ID NO 27
<211> LENGTH: 12
<212> TYPE: PRT
<213> ORGANISM: Artificial Sequence
<220> FEATURE:
<223> OTHER INFORMATION: 2SD4 heavy chain variable region CDR3

<400> SEQUENCE: 27

Ala Ser Tyr Leu Ser Thr Ser Ser Ser Leu Asp Asn
1               5                   10

<210> SEQ ID NO 28
<211> LENGTH: 12
<212> TYPE: PRT
<213> ORGANISM: Artificial Sequence
<220> FEATURE:
<223> OTHER INFORMATION: VH1B11 heavy chain variable region CDR3

<400> SEQUENCE: 28

Ala Ser Tyr Leu Ser Thr Ser Ser Ser Leu Asp Lys
1               5                   10

```
<210> SEQ ID NO 29
<211> LENGTH: 12
<212> TYPE: PRT
<213> ORGANISM: Artificial Sequence
<220> FEATURE:
<223> OTHER INFORMATION: VH1D8 heavy chain variable region CDR3

<400> SEQUENCE: 29

Ala Ser Tyr Leu Ser Thr Ser Ser Ser Leu Asp Tyr
 1               5                  10

<210> SEQ ID NO 30
<211> LENGTH: 12
<212> TYPE: PRT
<213> ORGANISM: Artificial Sequence
<220> FEATURE:
<223> OTHER INFORMATION: VH1A11 heavy chain variable region CDR3

<400> SEQUENCE: 30

Ala Ser Tyr Leu Ser Thr Ser Ser Ser Leu Asp Asp
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: VH1B12 heavy chain variable region CDR3

<400> SEQUENCE: 31

Ala Ser Tyr Leu Ser Thr Ser Phe Ser Leu Asp Tyr
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: VH1E4 heavy chain variable region CDR3

<400> SEQUENCE: 32

Ala Ser Tyr Leu Ser Thr Ser Ser Ser Leu His Tyr
 1               5                  10

<210> SEQ ID NO 33
<211> LENGTH: 12
<212> TYPE: PRT
<213> ORGANISM: Artificial Sequence
<220> FEATURE:
<223> OTHER INFORMATION: VH1F6 heavy chain variable region CDR3

<400> SEQUENCE: 33

Ala Ser Phe Leu Ser Thr Ser Ser Ser Leu Glu Tyr
 1               5                  10

<210> SEQ ID NO 34
<211> LENGTH: 12
<212> TYPE: PRT
<213> ORGANISM: Artificial Sequence
<220> FEATURE:
<223> OTHER INFORMATION: 3C-H2 heavy chain variable region CDR3

<400> SEQUENCE: 34

Ala Ser Tyr Leu Ser Thr Ala Ser Ser Leu Glu Tyr
 1               5                  10

<210> SEQ ID NO 35
```

```
<211> LENGTH: 12
<212> TYPE: PRT
<213> ORGANISM: Artificial Sequence
<220> FEATURE:
<223> OTHER INFORMATION: VH1-D2.N heavy chain variable region CDR3

<400> SEQUENCE: 35

Val Ser Tyr Leu Ser Thr Ala Ser Ser Leu Asp Asn
 1               5                  10

<210> SEQ ID NO 36
<211> LENGTH: 321
<212> TYPE: DNA
<213> ORGANISM: Artificial Sequence
<220> FEATURE:
<223> OTHER INFORMATION: adalimumab light chain variable region

<400> SEQUENCE: 36
gacatccaga tgacccagtc tccatcctcc ctgtctgcat ctgtagggga cagagtcacc      60
atcacttgtc gggcaagtca gggcatcaga aattacttag cctggtatca gcaaaaacca    120
gggaaagccc ctaagctcct gatctatgct gcatccactt tgcaatcagg ggtcccatct    180
cggttcagtg gcagtggatc tgggacagat ttcactctca ccatcagcag cctacagcct    240
gaagatgttg caacttatta ctgtcaaagg tataaccgtg caccgtatac ttttggccag    300
gggaccaagg tggaaatcaa a                                              321

<210> SEQ ID NO 37
<211> LENGTH: 363
<212> TYPE: DNA
<213> ORGANISM: Artificial Sequence
<220> FEATURE:
<223> OTHER INFORMATION: adalimumab heavy chain variable region

<400> SEQUENCE: 37
gaggtgcagc tggtggagtc tgggggaggc ttggtacagc ccggcaggtc cctgagactc      60
tcctgtgcgg cctctggatt cacctttgat gattatgcca tgcactgggt ccggcaagct    120
ccagggaagg gcctggaatg ggtctcagct atcacttgga atagtggtca catagactat    180
gcggactctg tggagggccg attcaccatc tccagagaca acgccaagaa ctccctgtat    240
ctgcaaatga acagtctgag agctgaggat acggccgtat attactgtgc gaaagtctcg    300
taccttagca ccgcgtcctc ccttgactat tggggccaag gtaccctggt caccgtctcg    360
agt                                                                  363
```

AUTOMATIC INJECTION DEVICE

CROSS REFERENCE TO RELATED APPLICATIONS

This application is a continuation of U.S. application Ser. No. 11/824,516, filed Jun. 29, 2007. U.S. application Ser. No. 11/824516 claims the benefit of priority to U.S. Provisional Patent Application Ser. No. 60/817,849, entitled AUTOMATIC INJECTION DEVICE, filed Jun. 30, 2006; U.S. Provisional Patent Application Ser. No. 60/838,905, entitled AUTOMATIC INJECTION DEVICE, filed Aug. 18, 2006; U.S. Provisional Patent Application Ser. No. 60/899,262, entitled METHODS FOR MONITORING AND TREATING TNFα RELATED DISORDERS, filed Feb. 2, 2007; U.S. Provisional Patent Application Ser. No. 60/849,967, entitled METHODS AND COMPOSITIONS FOR TREATING CROHN'S DISEASE, filed Oct. 6, 2006; U.S. Provisional Patent Application Ser. No. 60/904,626, entitled METHODS AND COMPOSITIONS FOR TREATING CROHN'S DISEASE, filed Mar. 1, 2007; U.S. Provisional Patent Application Ser. No. 60/918,174, entitled METHODS AND COMPOSITIONS FOR TREATING CROHN'S DISEASE, filed Mar. 14, 2007; and U.S. Provisional Patent Application Ser. No. 60/818,231, filed on Jun. 30, 2006. The contents of each of the above priority documents is hereby incorporated by reference herein.

FIELD OF THE INVENTION

The present invention relates to an injection device for injecting a substance, such as a drug, into a patient.

BACKGROUND OF THE INVENTION

One of the most common routes of administration for medications is by injection, such as intravenous, subcutaneous or intramuscular injection. A syringe containing the medication is used for the injection, which typically is carried out by trained medical personnel. In certain instances, a patient is trained in the use of the syringe to allow for self-injection. Moreover, certain medications are formulated in pre-filled syringes for patient use, to avoid the need for the patient to fill the syringe. Some patients, however, may be averse to carrying out self-injection, particularly if the patient has a fear of needles.

Automatic injection devices offer an alternative to a syringe for delivering a medication. Automatic injection devices have been used, for example, to deliver medications under emergency conditions, such as to administer epinephrine to counteract the effects of a severe allergic reaction, for example, as caused by a food allergy. Automatic injection devices also have been described for use in administering antiarrhythmic medications and selective thrombolytic agents during a heart attack (see e.g., U.S. Pat. Nos. 3,910,260; 4,004,577; 4,689,042; 4,755,169 and 4,795,433). Various types of automatic injection devices also are described in, for example, U.S. Pat. Nos. 3,941,130; 4,261,358; 5,085,642; 5,092,843; 5,102,393; 5,267,963; 6,149,626; 6,270,479; and 6,371,939.

In general, prior automatic injection devices, when operated, cause the needle of a syringe to move forward and project from a protective housing prior to actuation of the syringe to eject a dose of liquid through the needle. Movement of the syringe toward the patient's skin such that the needle is exposed before pressurizing a liquid charge inside the syringe helps prevent the liquid from dripping out of the needle before the actual injection takes place.

Such prior automatic injection devices have several disadvantages. For example, prior devices include an exposed needle that a patient is required to inject into him or herself, causing apprehension and anxiety for most patients, particularly those patients that are "needle phobic". Prior devices are also difficult for patients to use, to maintain free of contamination, and/or to provide an accurate dosage of medicine. In addition, patients suffering from chronic autoimmune diseases such as rheumatoid arthritis, as well as the elderly and physically disabled, may lack the dexterity needed to self-administer biologic therapies using existing injection devices. A need therefore exists for such self-medication delivery devices that patients are able to use safely and that foster patient adherence to their biologic therapy regimens.

TNFα inhibitors are effective in the treatment of autoimmune disorders such as rheumatoid arthritis, psoriatic arthritis and Crohn's Disease. Such inhibitors, which include biological agents such as antibodies and antibody fusion proteins, typically are delivered by injection. The TNFα inhibitor adalimumab (HUMIRA®; Abbott Laboratories, Lake County, Ill.), for example, has been marketed as a pre-filled syringe for self-administration by patients and therefore presents as an important candidate for use with an improved automatic injection devices and methods.

SUMMARY OF THE INVENTION

The present invention provides improved devices, components thereof, and methods of administering an injectable therapy to a patient. In an embodiment, the invention provides an automatic injection device for ejecting a dose of fluid medication from a needle of a syringe movably disposed within a housing of the device. Prior to use, the syringe of the invention is in a retracted position within the housing. During a first operational stage, initiated by actuating an activation button, an actuator propels the syringe towards a proximal end of the housing to project a needle of the syringe from the proximal end. In this first operational stage, the actuator causes the needle to be inserted into a subcutaneous region of the skin of the user when the proximal end of the device is held against an injection site. In a second operational stage, an actuator, which may be the same or a different component as the actuator that causes the needle to be inserted, causes the fluid disposed within the syringe to be ejected into the subcutaneous region.

The automatic injection device of the invention may be used to inject a dose of a tumor necrosis factor-α (TNFα) inhibitor to treat any number of diseases, including rheumatoid arthritis, psoriasis, Crohn's disease, psoriatic arthritis, and juvenile rheumatoid arthritis. In one embodiment, the user has a disorder in which TNFα is detrimental selected from the group consisting of rheumatoid arthritis, psoriasis, Crohn's disease, ankylosing spondylitis, psoriatic arthritis, and juvenile rheumatoid arthritis.

The automatic injection device may include a window to allow a user to view the contents and/or level of the contents of the syringe. In addition, the automatic injection device may include an indicator to indicate when an injection is complete. A "dummy" or demonstration training automatic injection device may also be provided for training a user to use the automatic injection device to inject a substance without actually injecting a substance into the user.

The invention provides an automatic injection device for providing a subcutaneous injection of a substance into a user or patient, comprising a housing having an open first end and a second end, a syringe movably disposed in the housing, the syringe including a barrel portion for holding the substance, a hollow needle in fluid communication with the barrel portion for ejecting the substance from the syringe, and a bung for sealing the barrel portion and selectively applying pressure to the substance to force the substance through the hollow needle, a syringe actuation component for first moving the syringe towards the first end of the housing such that the needle projects from the first end and for subsequently applying pressure to the bung, the syringe actuation component including a pressurizer for selectively applying pressure to the bung, a compressible expanded central portion and a flange between a second end of the syringe actuation component and the compressible expanded central portion and a first biasing mechanism for biasing the syringe actuation component towards the first open end of the housing, the first biasing mechanism disposed between the flange of the syringe actuation component and the second end of the housing.

In one embodiment, the automatic injection device further comprises an activation button disposed on the housing for actuating the syringe actuation component. In another embodiment, the automatic injection device includes an activation button coupled to the housing for actuating the syringe actuation component.

In another embodiment, the automatic injection device further comprises a latch actuated by the activation button for latching the syringe actuation component in a retracted position prior to actuation by the activation button.

The invention also includes an automatic injection device for providing a subcutaneous injection of a substance into a user, comprising a housing having an open first end and a second end, a syringe movably disposed in the housing, the syringe including a barrel portion for holding the substance, a hollow needle in fluid communication with the barrel portion for ejecting the substance from the syringe, and a bung for sealing the barrel portion and selectively applying pressure to the substance to force the substance through the hollow needle, an actuator for selectively moving the syringe towards a first end of the housing so that the needle extends from the open first end of the housing and an actuator for expelling the substance from the syringe after movement of the syringe towards the open first end of the housing. A first removable cap may cover the first end of the housing.

The actuator may include a first biasing mechanism, a second biasing mechanism, a plunger-type syringe actuator and/or another actuator means.

In one embodiment, the automatic injection device further comprises a dose of a substance, e.g., a TNF inhibitor, loaded in the barrel portion of the syringe.

Included in the invention, is an automatic injection device for providing a subcutaneous injection of a substance into a user, comprising a housing having an open first end, a second end and a window disposed in a side wall for viewing the interior of the housing, a syringe movably disposed in the housing, the syringe including a barrel portion for holding the substance, a hollow needle in fluid communication with the barrel portion for ejecting the substance from the syringe, and a bung for sealing the barrel portion and selectively applying pressure to the substance to force the substance through the hollow needle, an actuator for selectively moving the syringe towards a first end of the housing so that the needle extends from the first end of the housing and an actuator for expelling the substance from the syringe after movement of the syringe towards the first end of the housing.

In one embodiment, the window has a substantially keyhole shape. In a further embodiment, the window includes a fill line at a position in the window for indicating a full dose of the substance.

The invention further provides an automatic injection device for providing a subcutaneous injection of a substance into a user, comprising a housing having an open first end and a second end, a syringe movably disposed in the housing, the syringe including a barrel portion for holding the substance, a hollow needle in fluid communication with the barrel portion for ejecting the substance from the syringe, and a bung for sealing the barrel portion and selectively applying pressure to the substance to force the substance through the hollow needle, a syringe actuation component for selectively applying pressure to the bung, the syringe actuation component including a pressurizer configured to be inserted into the barrel portion of the syringe, a compressible expanded central portion and an indicator disposed between the compressible expanded central portion and a second end of the syringe actuation component for indicating when the contents of the syringe have been expelled.

The invention includes an automatic injection device for providing a subcutaneous injection of a substance into a user, comprising a housing having an open first end, a second end and having a window formed in a side wall thereof, a syringe movably disposed within the housing for storing and selectively ejecting the substance from the open first end; and an indicator that aligns with the window in the side wall when the syringe is substantially empty of the substance.

Another aspect of the invention includes an automatic injection device, comprising a housing having a substantially tubular configuration with an open first end and a second end; a syringe movably disposed within the housing, the syringe containing a dose of a substance, e.g., a TNF inhibitor, wherein the syringe moves within the housing to inject the TNF inhibitor into a user.

In one embodiment, the automatic injection device further comprises an indicator for indicating when the substance, e.g., a TNF inhibitor, has been ejected from the syringe.

In one embodiment, the automatic injection device further comprises a window formed in the housing to allow viewing of the interior of the housing.

In one embodiment, the automatic injection device further comprises an indicator that aligns with the window when the substance, e.g., a TNF inhibitor, has been ejected from the syringe.

Another aspect of the invention is an automatic injection device for providing a subcutaneous injection of a substance into a user, comprising a housing having an open first end and a second end; a plunger including a rod configured to be connected at a first end to a bung of a syringe, a compressible expanded central portion and a flange between a second end of the rod and the compressible expanded central portion; and a biasing mechanism for biasing the plunger towards the first open end of the housing, the biasing mechanism disposed about the second end of the rod between the flange and the second end of the housing.

In one embodiment, the automatic injection device further comprises an activation button disposed on the housing for actuating the plunger.

In one embodiment, the automatic injection device further comprises a latch actuated by the activation button for latching the plunger in a retracted position prior to actuation by the activation button.

In one embodiment of the invention, the automatic injection device further comprises a window on the housing for viewing the interior of the housing.

In still another embodiment, the automatic injection device further comprises an indicator for indicating when the syringe is empty.

In another embodiment, the automatic injection device comprises a syringe comprising a dose of a substance, e.g., a TNF inhibitor, to be injected into a user.

In still another embodiment, the automatic injection device further comprises a removable cap for covering one of the first end and the second end of the housing.

In one embodiment, the invention provides an automatic injection device further comprising a needle sheath that advances over the needle projecting through the first end after ejection of the substance from the syringe.

The invention features automatic injection device comprising a dose of a TNFα inhibitor, e.g, adalimumab. In one embodiment, the automatic injection device further comprises a dose of a TNF inhibitor loaded in the barrel portion of the syringe.

The invention includes a housing for an automatic injection device, comprising a hollow substantially tubular housing including an open first end and a second end, the hollow substantially tubular housing configured to slidably receive a syringe therein; a first stop in an interior surface of the housing for limiting movement of the syringe in a first direction; and a second stop on the interior surface of the housing for limiting movement of the syringe in a second direction.

In one embodiment, the housing further comprises a shelf formed between the open first end and the first stop for seating a biasing mechanism for biasing the syringe away from the first end of the housing. In one embodiment, the housing further comprises a window formed in a side wall of the housing for allowing viewing of the interior of the housing. In one embodiment, the housing further comprises an activation button disposed at the second end of the tubular housing for selectively activating the syringe to move from a first, retracted position to a second, projecting position where a needle of the syringe projects from the first end, and, while the syringe is in the second, projecting position, apply pressure to eject a substance from the syringe.

The invention further includes a syringe for use in an automatic injection device, comprising a barrel portion for containing a substance; a hollow needle in fluid communication with the barrel portion; a bung for sealing the barrel portion, the bung movable within the barrel portion to increase pressure within the barrel portion to force the substance through the hollow needle; a first stop formed on an intermediate portion of the barrel portion for abutting a stop in a housing of the automatic injection device to limit movement of the syringe in a first direction; and a second stop formed on a distal end of the barrel portion for limiting movement of the syringe relative to the housing of the automatic injection device in a second direction. In another embodiment, the stops may be formed at other locations throughout the barrel.

In one embodiment, the syringe further comprises a plunger for selectively first moving the syringe towards an open first end of the housing of the automatic injection device, such that the needle projects from the first end, and subsequently applying pressure to the bung to cause the syringe to eject the substance through the hollow needle.

In one embodiment, the plunger comprises a rod connected at a first end to the bung and a compressible expanded central portion. In another embodiment, the plunger further includes an indicator for indicating when the syringe has ejected substantially all of the substance through the hollow needle. In one embodiment, the syringe further comprises a dose of a TNF inhibitor loaded in the barrel portion of the syringe.

The invention further provides a syringe actuation component for an injection device, comprising a rod portion having a first end, a second end and a compressible expanded central portion, and a pressurizer formed on the first end of the rod portion for applying pressure to a bung of a syringe.

In one embodiment, the syringe actuation component further comprises an anchoring portion formed on a second end of the rod portion for anchoring a coil spring to the syringe actuation component. In one embodiment, the syringe actuation component further comprises an indicator for indicating completion of an injection formed in a solid rod portion between the compressible expanded central portion and the second end of the rod portion. In one embodiment, the syringe actuation component further comprises a retaining flange for holding the coil spring in a compressed position until actuation. In one embodiment, the syringe actuation component further comprises a spring base for the coil spring extending between the anchoring end and the retaining flange. In one embodiment, the spring base comprises flexible legs around the spring coils. In another embodiment, the anchoring end comprises tabbed feet extending from the base and configured to releasably engage an activation button.

The invention further provides an article of manufacture comprising a packaging material and an automatic injection device comprising a TNFα inhibitor. In one embodiment, the TNFα inhibitor comprises adalimumab. In one embodiment, the dose of adalimumab is 40 mg. The article of manufacture may also comprise an alcohol prep and/or a dose tray for holding the automatic injection device.

The invention also provides an article of manufacture comprising an automatic injection device having a pre-filled syringe containing a dose of a TNFα inhibitor; and an alcohol preparation pad, packaged with instructions for use to treat arthritis by injecting the dose into the skin of a user using the automatic injection device.

The invention also provides an article of manufacture comprising: an automatic injection device having a pre-filled syringe containing a dose of a TNFα inhibitor; and an alcohol preparation pad, packaged with instructions for use to treat arthritis by injecting the dose into the skin of a user using the automatic injection device.

The invention also includes a method of injecting a substance, comprising the steps of providing an automatic injection device comprising a housing having an open first end, a second end, a syringe movably disposed within the housing containing the substance, a cap covering the first end and a cap covering an activating button on the second end; removing the first cap; removing a second cap to expose the activating button; positioning the open first end of the device adjacent the skin of a user; actuating the activating button to cause a needle of the syringe to first project from the open first end and into the skin of the user and subsequently ejecting the substance through the needle an into a subcutaneous region of the user; and removing the device after the substance is ejected.

In one embodiment, the automatic injection device is held at about a 90 degree angle relative to the skin of the user. In one embodiment, an indicator provides an indication to the user when the syringe is substantially empty of the substance. In one embodiment, the substance loaded and ejected from the syringe is a dose of a TNF inhibitor.

In still another embodiment of the invention, the method includes (a) positioning the automatic injection device at an injection site of the user; (b) engaging the activator mechanism to begin injection of the substance to the user; (c) maintaining engagement of the activator mechanism for a prescribed period of time to continue injection of the substance;

and (d) removing the automatic injection device from the injection site after passage of the prescribed period of time.

In yet another embodiment of the invention, the method includes (a) positioning the automatic injection device at an injection site; (b) engaging the activator mechanism to begin injection of the substance to the user; (c) maintaining engagement of the activator mechanism to continue injection of the substance until a visible indicator of completion is detected; and (d) removing the automatic injection device from the injection site once the visible indicator of completion is detected.

The invention also features a method of training a recipient on use of an automatic injection device.

One aspect of the invention is a device for training a recipient to use an automatic injection device, comprising a housing having a window, an activation button on a first end of the housing; and an indicator movably disposed within the housing, wherein the indicator aligns with the window of the housing after a user activates the activation button.

In an embodiment, the device further comprises an activation component for selectively moving the indicator from a hidden position to a position aligned with the window. In one embodiment, the activation component comprises a rod having an anchoring portion on a first end that is selectively latched by the activation button, a flanged portion for retaining a biasing mechanism towards the first end of the housing, and wherein the indicator is formed between a second end of the rod and the flanged portion.

The invention also provides a kit for training a recipient on use of an automatic injection device, wherein the automatic injection device comprises a needle and a medication, the kit comprising: (a) a demonstration automatic injection device which lacks the needle and the medication; and (b) instructions for using the automatic injection device.

In one embodiment, the instructions convey a method to the recipient for using the demonstration automatic injection device, the method comprising: (a) position the automatic injection device at an injection site; (b) engage the activator mechanism to begin injection of the medication; (c) maintain engagement of the activator mechanism for a prescribed period of time to continue injection of the medication; and (d) remove the automatic injection device from the injection site after passage of the prescribed period of time.

In one embodiment, the prescribed period of time is 10 seconds. In another embodiment, the prescribed period of time is at least 10 seconds.

In one embodiment, the instructions further convey that initial engagement of the activator mechanism is accompanied by an audible sound. In another embodiment, the instructions further convey that completion of injection of the medication is accompanied by a visible indicator of completion.

In one embodiment, the instructions further convey that the injection site may be sterilized prior to positioning the automatic injection device at the injection site.

In one embodiment, the instructions further convey that the automatic injection device be examined for proper dosage and formulation of the medication prior to positioning the automatic injection device at the injection site.

In one embodiment, the instructions further convey to the recipient, at least one message selected from the group consisting of: (a) the automatic injection device is less painful for a patient to use than a pre-filled syringe; (b) the automatic injection device is preferred for use by patients as compared to a pre-filled syringe; (c) the automatic injection device is easier to use by a patient than a pre-filled syringe; (d) the automatic injection device is more convenient for a patient to use than a pre-filled syringe; (e) the automatic injection device reduces anxiety of patients with a fear of needles, as compared to a pre-filled syringe, since the needle is not visible in the device; and (f) the automatic injection device is designed to be easy to use from initial use of the device.

In one embodiment, the recipient is a physician that prescribes the medication. In another embodiment, the recipient is a patient that uses the medication. In yet another embodiment, the recipient is a care-giver, such as a family member.

The invention also includes a demonstration automatic injection device comprising a housing having an open first end, a second end, and having a window formed in a side wall thereof, a syringe movably disposed within the housing; an activator mechanism associated with the syringe for depressing the syringe; and an indicator that aligns with the window in the side wall when the syringe is fully depressed.

The invention features an audiovisual device for promoting an automatic injection device comprising a medication to a recipient, wherein the device conveys to the recipient at least one message selected from the group consisting of: (a) the automatic injection device is less painful for a patient to use than a pre-filled syringe; (b) the automatic injection device is preferred for use by patients as compared to a pre-filled syringe; (c) the automatic injection device is easier to use by a patient than a pre-filled syringe; (d) the automatic injection device is more convenient for a patient to use than a pre-filled syringe; (e) the automatic injection device reduces anxiety of patients with a fear of needles, as compared to a pre-filled syringe, since the needle is not visible in the device; and (f) the automatic injection device is designed to be easy to use from initial use of the device.

The invention also includes an audiovisual device or printed material for training a recipient on the use of an automatic injection device, wherein the automatic injection device comprises an activator mechanism and a medication, the audiovisual device conveying to the recipient instructions to: (a) position the automatic injection device at an injection site; (b) engage the activator mechanism to begin injection of the medication; (c) maintain engagement of the activator mechanism for a prescribed period of time to continue injection of the medication; and (d) remove the automatic injection device from the injection site after passage of the prescribed period of time.

The invention also includes an audiovisual device or printed material for for training a recipient on the use of an automatic injection device, wherein the automatic injection device comprises an activator mechanism and a medication, the audiovisual device conveying to the recipient instructions to: (a) position the automatic injection device at an injection site; (b) engage the activator mechanism to begin injection of the medication; (c) maintain engagement of the activator mechanism to continue injection of the medication until a visible indicator of completion is detected; and (d) remove the automatic injection device from the injection site once the visible indicator of completion is detected.

The invention further provides a method of training a recipient on the use of an automatic injection device, wherein the automatic injection device comprises an activator mechanism and a medication. The method comprises, in one embodiment, conveying to the recipient instructions to: (a) position the automatic injection device at an injection site; (b) engage the activator mechanism to begin injection of the medication; (c) maintain engagement of the activator mechanism to continue injection of the medication until a visible indicator of completion is detected; and (d) remove the automatic injection device from the injection site once the visible indicator of completion is detected.

In one embodiment, the automatic injection device comprises an indicator window and the visible indicator of completion comprises a color indicator, e.g, yellow, appearing in the indicator window.

In one embodiment, the instructions further convey that initial engagement of the activator mechanism is accompanied by an audible sound.

In one embodiment, the instructions further convey that engagement of the activator mechanism is maintained for a prescribed period of time, e.g., 10 seconds, to continue injection of the medication. In one embodiment, the instructions further convey that the injection site be sterilized prior to positioning the automatic injection device at the injection site.

In one embodiment, the instructions further convey that the automatic injection device be examined for proper dosage and formulation of the medication prior to positioning the automatic injection device at the injection site.

In another aspect, the invention pertains to a method of training a user on the use of an automatic injection device, wherein the automatic injection device comprises a needle and a medication, the method comprising providing to the user: (a) a demonstration automatic injection device which lacks the needle and the medication; and (b) instructions for using the automatic injection device.

In yet another aspect, the invention pertains to a kit for training a recipient on the use of an automatic injection device comprises a needle and a medication, the kit comprising: (a) a demonstration or "trainer" automatic injection device which lacks the needle and the medication; and (b) instructions for using the automatic injection device.

In yet another aspect, the invention pertains to a method of training a recipient on the use of an automatic injection device, wherein the automatic injection device comprises an activator mechanism and a medication. The training method comprises conveying to the recipient instructions to: (a) position the automatic injection device at an injection site; (b) engage the activator mechanism to begin injection of the medication; (c) maintain engagement of the activator mechanism for a prescribed period of time to continue injection of the medication; and (d) remove the automatic injection device from the injection site after passage of the prescribed period of time.

Preferred prescribed periods of time for engaging the activator mechanism include 10 seconds, or engaging the activator mechanism for at least 10 seconds. In certain embodiments, the instructions further convey that initial engagement of the activator mechanism is accompanied by an audible sound. In certain embodiments, the instructions further convey that completion of injection of the medication is accompanied by a visible indicator of completion. In certain other embodiments, the instructions further convey that the injection site be sterilized prior to positioning the automatic injection device at the injection site. In certain embodiments, the instructions further convey that the automatic injection device should be examined for proper dosage and formulation of the medication prior to positioning the automatic injection device at the injection site.

In another aspect, the invention pertains to a method of training a recipient on the use of an automatic injection device, wherein the automatic injection device comprises an activator mechanism and a medication. The training method comprises conveying to the recipient instructions to: (a) position the automatic injection device at an injection site; (b) engage the activator mechanism to begin injection of the medication; (c) maintain engagement of the activator mechanism to continue injection of the medication until a visible indicator of completion is detected; and (d) remove the automatic injection device from the injection site once the visible indicator of completion is detected.

In a preferred embodiment, the automatic injection device comprises an indicator window and the visible indicator of completion comprises a color indicator appearing in the indicator window. The color indicator can be, for example, a yellow color indicator.

In one embodiment, the instructions are provided in a printed document or in an audiovisual device. In another embodiment, the audiovisual device is a Video Home System (VHS) cassette or a Digital Video Disc (DVD). In one embodiment, the instructions are conveyed orally to the recipient.

In one embodiment, the recipient is a physician that prescribes the medication. In one embodiment, the recipient is a patient that uses the medication.

The invention also includes an article of manufacture comprising a packaging material; a TNFα inhibitor, such as adalimumab; and a label or package insert contained within the packaging material indicating that in studies of the TNFα inhibitor using the automatic injection device of the invention for the treatment of a disorder in which TNFα is detrimental, such as rheumatoid arthritis, the most common adverse events (AEs) were bronchitis, hypersensitivity, arthritic pain, cough and rhinitis.

The invention further provides an article of manufacture comprising: a packaging material; an automatic injection device, e.g., an autoinjector pen filled with a TNFα inhibitor; and a label or package insert contained within the packaging material indicating that the bioequivalence of the TNFα inhibitor is similar regardless of whether the injection site is the thigh or abdomen.

The article of manufacture of the invention may comprise a label. In one embodiment, the label of the invention indicates how the TNFα inhibitor, e.g., TNF antibody, or antigen binding portion thereof, is packaged as an article of manufacture. In one embodiment, the label of the invention indicates the TNFα inhibitor, e.g., TNF antibody, or antigen binding portion thereof, is dispensed in a carton containing 6 alcohol preps and 6 dose trays (e.g., labeled Crohn's Disease Starter Package). In another embodiment, the label indicates that each dose tray consists of a single-use pen each pen, containing a 1 mL prefilled glass syringe with a fixed 27 gauge ½ inch needle, providing 40 mg (0.8 mL) of the TNFα inhibitor.

The present invention relates to automatic injection devices for administering medications and in particular relates to compositions and methods for promoting the use of such devices and to compositions and methods for training users (e.g., patients and medical personel) in the use of such devices. The invention is based, at least in part, on results of a clinical study comparing an automatic injection device for administering adalimumab (HUMIRA®) to a pre-filled syringe for administering adalimumab (HUMIRA®). The study revealed numerous advantageous features of the automatic injection device and identified particular aspects of using the device to be highlighted when training someone to use the device.

Accordingly, in one aspect, the invention pertains to a method of promoting an automatic injection device comprising a medication to a recipient. The method comprises conveying to the recipient at least one message selected from the group consisting of: (a) the automatic injection device is less painful for a patient to use than a pre-filled syringe; (b) the automatic injection device is preferred for use by patients as compared to a pre-filled syringe; (c) the automatic injection device is easier to use by a patient than a pre-filled syringe; (d)

the automatic injection device is more convenient for a patient to use than a pre-filled syringe; (e) the automatic injection device reduces anxiety of patients with a fear of needles, as compared to a pre-filled syringe, since the needle is not visible to the user while using the device; and (f) the automatic injection device is designed to be easy to use from the initial use of the device.

In a preferred embodiment, the message conveyed to the user is that the automatic injection device is less painful for a patient to use than a pre-filled syringe, for example that 80% of patients in a clinical trial rated the automatic injection device as less painful than a pre-filled syringe. In another preferred embodiment, the message conveyed to the recipient is that the automatic injection device is preferred for use by patients as compared to a pre-filled syringe, for example that 90% of patients in a clinical trial preferred the automatic injection device to a pre-filled syringe.

In certain embodiments, the user is conveyed the information that the automatic injection device comprises a five bevel needle, as compared to a three bevel needle for a pre-filled syringe.

In another aspect, the invention pertains to an audiovisual device for promoting an automatic injection device comprising a medication to a user, wherein the device conveys to the user at least one of the messages provided above. In the methods and compositions of the invention, the promotional messages or training instructions can be conveyed, for example, orally to the recipient and/or in writing to the recipient. Alternatively or in addition, the audiovisual device can be, for example, a Video Home System (VHS) cassette or a Digital Video Disc (DVD).

In the methods of the invention, the recipient of the promotional messages or training instructions can be, for example, a physician that prescribes the medication, a patient that uses the medication, or a caregiver.

In the methods and compositions of the invention, preferably the automatic injection device provides for subcutaneous injection of the medication. Preferred embodiments of the automatic injection device are described herein.

The automatic injection device used in the methods and compositions of the invention may comprise a substance or medication that is, for example, an antibody, a cytokine, a vaccine, a fusion protein or a growth factor. In a preferred embodiment, the medication is a TNFα inhibitor (e.g., an anti-TNF antibody or an antigen-binding portion thereof, a TNF fusion protein, or a recombinant TNF binding protein), such as infliximab (the REMICADE™ antibody, Centocor, Horsham, Pa.), CDP 571, CDP 870, anti-TNF dAb, golimumab, adalimumab, etanercept (the ENBREL™ protein, Amgen, Calif.), p55TNFR1gG (Lenercept) or r-TBP-1. A particularly preferred medication for use in the automatic injection device is adalimumab (HUMIRA®). Another particularly preferred medication for use in the automatic injection device is an isolated human antibody that dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an IC$_{50}$ of $1 \times 10^{-7}$ M or less. In one embodiment, the automatic injection device, including uses and compositions thereof, comprises a dose of a TNFα inhibitor.

In one embodiment, the anti-TNFα antibody, or antigen-binding portion thereof, is selected from the group consisting of a chimeric antibody, a humanized antibody, a human antibody, and a multivalent antibody.

In one embodiment, the anti-TNFα antibody is an isolated human antibody, or antigen-binding portion thereof, with the following characteristics: a) dissociates from human TNFα with a $K_{off}$ rate constant of $1 \times 10^{-3}$ s$^{-1}$ or less, as determined by surface plasmon resonance; b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9; and c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In one embodiment, the anti-TNFα antibody is an isolated human antibody, or an antigen binding portion thereof, with a light chain variable region (LCVR) comprising the amino acid sequence of SEQ ID NO: 1 and a heavy chain variable region (HCVR) comprising the amino acid sequence of SEQ ID NO: 2

In one embodiment, the anti-TNFα antibody, or antigen-binding portion thereof, is selected from the group consisting of infliximab, golimumab, and adalimumab In one embodiment, the TNFα inhibitor is selected from the group consisting of infliximab, CDP 571, CDP 870, anti-TNF dAb, golimumab, adalimumab, etanercept, p55TNFRIgG and r-TBP-1.

In one embodiment, the substance that is loaded into the automatic injection device is a formulation comprising adalimumab, sodium chloride, monobasic sodium phosphate dihydrate, dibasic sodium phosphate dihydrate, sodium citrate, citric acid monohydrate, mannitol, polysorbate 80, and water.

In one embodiment, the automatic injection device is used to deliver an anti-TNFα antibody, or antigen-binding portion thereof, to a used, wherein administration is given on a biweekly dosing regimen or a multiple variable dose regimen.

BRIEF DESCRIPTION OF THE FIGURES

The foregoing and other objects, features and advantages of the present invention, as well as the invention itself, will be more fully understood from the following description of preferred embodiments when read together with the accompanying drawings, in which:

FIG. 3 is a cross-sectional schematic view of an automatic injection device of an embodiment of the invention prior to use.

FIG. 4 is a cross-sectional schematic view of the automatic injection device of FIG. 3 during a subsequent stage of operation.

FIG. 5 is a cross-sectional schematic view of the automatic injection device of FIG. 3 during a final stage of operation.

FIG. 6 illustrates an embodiment of an automatic injection device according to one embodiment of the invention.

DETAILED DESCRIPTION OF THE INVENTION

Figures 1, 2:
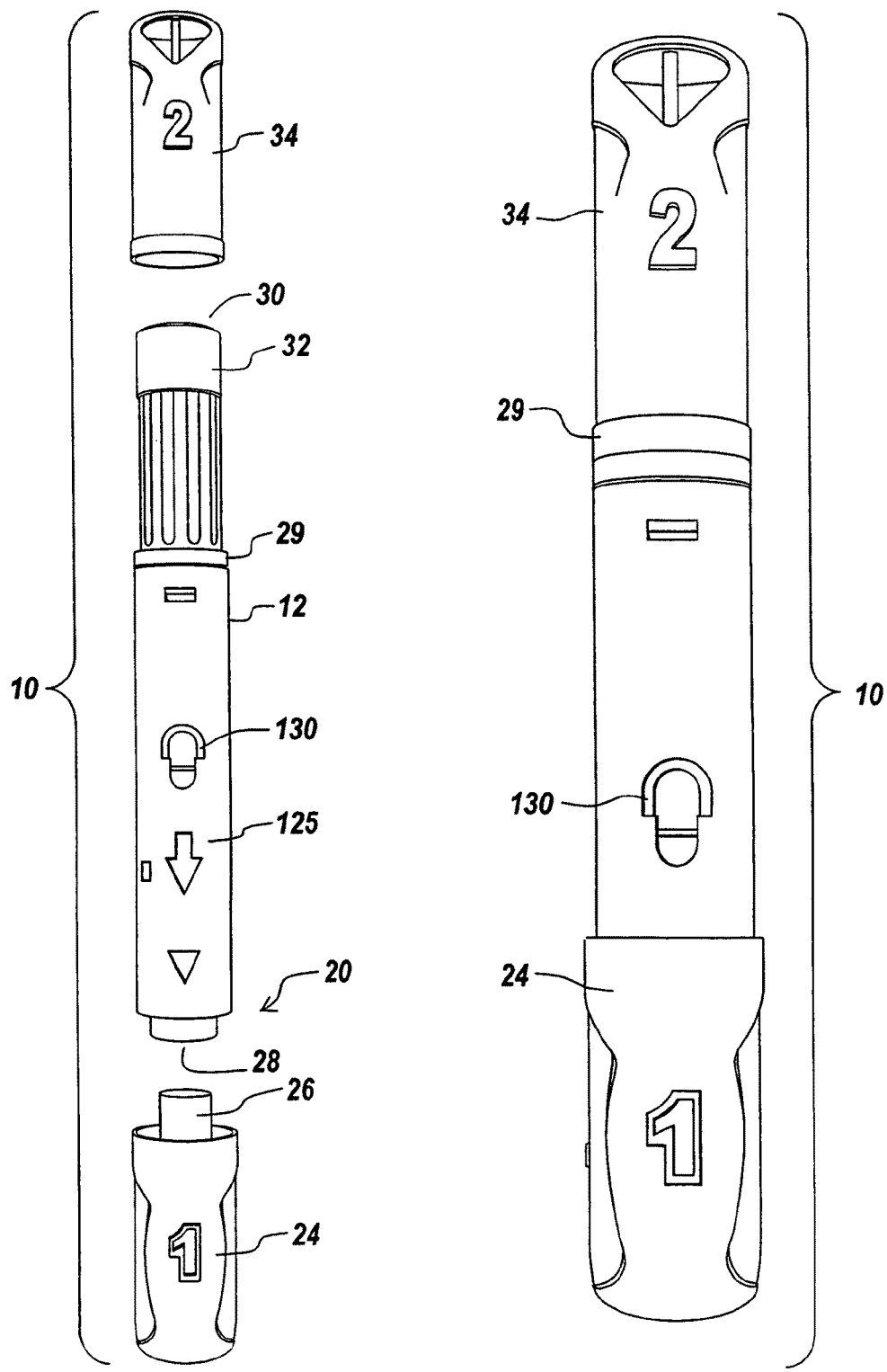
FIG. 1 is a perspective view of the automatic injection device according to an illustrative embodiment of the invention.
FIG. 2 is an exploded view of the automatic injection device according to an illustrative embodiment of the invention.

The present invention provides automatic injection devices, components thereof, and methods for injecting a substance, such as a liquid drug, into a patient to manage or cure a medical condition. In one embodiment, the automatic injection device is a pen, i.e., an autoinjector pen or autoinjection pen (used interchangeably herein). The present invention also provides a demonstration or "trainer" automatic injection device, which may be used to train a patient how to use an automatic injection device.

The present invention also relates to automatic injection devices for administering substances (also referred to herein as medications) and in particular relates to compositions and methods for promoting the use of such devices and to compositions and methods for training people in the use of such devices. The invention is based, at least in part, on results of a clinical study comparing an automatic injection device for administering adalimumab (HUMIRA®) to a pre-filled syringe for administering adalimumab (HUMIRA®). The study, described in detail in Examples 1 and 2 herein, revealed numerous advantageous features of the automatic injection device of the invention and identified particular aspects of methods of using the device that should be highlighted when training a recipient to use the device.

I. Definitions

So that the invention may be more readily understood, certain terms are defined, as follows:

As used herein, an "automatic injection device" (or "auto-injector") is intended to refer to a device that enables an individual (also referred to herein as a user or a patient) to self-administer a dosage of a substance, such as a liquid medication, wherein the device differs from a standard syringe by the inclusion of a mechanism for automatically delivering the medication to the individual by injection when the mechanism is engaged.

As used herein, the term "pre-filled syringe" is intended to encompass a syringe that is filled with a medication immediately prior to administration of the medication to an individual and a syringe that is filled with a medication and stored in this pre-filled form for a period of time before administration of the medication to an individual.

As used herein, a "recipient" is intended to refer to any person or individual that receives the promotional messages or training instructions of the methods and compositions of the invention described herein. Preferred recipients include physicians that prescribe the medication to be administered by the automatic injection device, and patients that use the medication to be administered by the automatic injection device, and their caregivers.

As used herein, the term "conveying to the recipient" is intended to encompass any means by which a promotional message or training instruction of the methods and compositions of the invention described herein is communicated to or expressed to a recipient. Non-limiting examples of means for conveying a message or instruction to a recipient include oral communication, written communication and communication via an audiovisual device.

As used herein, the term "initial use of the device" is intended to refer to the first time the automatic injection device is used to administer a substance, e.g., a medication, to an individual.

As used herein, the term "printed document" is intended to refer to any document that has written communication printed on it. Non-limiting examples of printed documents include brochures, leaflets, product inserts, flyers, flipcharts, tent cards and package labels.

As used herein, the term "audiovisual device" is intended to refer to any device that is capable of communicating information in auditory and visual form. Non-limiting examples of audiovisual devices include Video Home System (VHS) cassettes, Digital Video Discs (DVDs), CD-ROMS, digital videocassettes, 8 mm or 35 mm films and computers displaying Webcasts.

As used herein, the term "demonstration automatic injection device" or "a device for training" or "trainer" is intended to refer to an automatic injection device that is used to demonstrate the procedure for using the automatic injection device, including the look and feel of using the device, but which is not suitable for administering a substance, e.g., a medication, because it lacks one or more necessary components for administration of a substance, e.g., a medication and/or a needle. In a preferred embodiment, the demonstration automatic injection device lacks a needle and the substance, e.g., a medication, as compared to the automatic injection device.

II. Automatic Injection Device of Invention

The invention will be described below relative to certain illustrative embodiments. While the present invention is described with respect to using the device to provide a subcutaneous injection of a dose of a TNF inhibitor, one skilled in the art will recognize that the invention is not limited to the illustrative embodiment, and that the injection device may be used to inject any suitable substance into a user. In addition, the components and the method of using the automatic injection device are not limited to the illustrative embodiments described below.

As used herein, the term "distal" refers to the portion or end of an automatic injection device or component in the automatic injection device furthest from an injection site of the user when the device is held against the person for an injection or for mimicking an injection. The term "proximal" refers to the portion or end of an automatic injection device or a component of the automatic injection device closest to an injection site of the user during an injection.

FIGS. 1 and 2 superficially illustrate an automatic injection device 10 suitable for subcutaneously injecting a dose of a substance, such as a liquid drug, into a patient according to an illustrative embodiment of the invention. The automatic injection device 10 includes a housing 12 for housing a container, such as a syringe, containing a dose of a substance to be injected into a patient, as described in detail below. The housing 12 preferably has a tubular configuration, though one skilled in the art will recognize that the housing 12 may have any suitable size, shape and configuration for housing a syringe or other container of a substance to be injected. While the invention will be described with respect to a syringe mounted in the housing 12, one skilled in the art will recognize that the automatic injection device 10 may employ any suitable container for storing and dispensing a substance.

Referring to FIG. 2, the syringe is preferably slidably mounted in the housing 12, as described in detail below. In an inactivated position, the syringe is sheathed and retracted within the housing 12. When the device is actuated, a needle of the syringe projects from a first (proximal) end 20 of the housing 12 to allow ejection of a substance from the syringe into a patient. As shown, the first end of the housing 20, i.e., the proximal end, includes an opening 28 through which the needle of the syringe projects during actuation of the device 10.

Continuing to refer to FIGS. 1 and 2, a second (distal) end 30 of the housing 12, i.e., the distal end, includes an activation button 32 for actuating the syringe to move from a sheathed position within the housing 12 to a projecting position, and subsequently to expel the substance from the needle into the patient. The housing 12 houses one or more actuators that perform the functions of moving the syringe and expelling the substance from the syringe.

The illustrative automatic injection device 10 shown in FIGS. 1 and 2 may also include a first removable cap 24 (or needle cap) for covering the first end 20 of the housing 12, to prevent exposure of the needle in the syringe prior to use. In the illustrative embodiment, the first cap 24 may include a boss 26 for locking and/or covering the interior components of the device 10 until the user is ready to activate the device 10. Alternatively, the first cap 24 may comprise a threaded screw portion and the internal surface of the housing 12 at opening 28 may comprise screw thread. Any suitable mating mechanism may be used in accordance with the teachings of the invention.

A second removable cap 34 (or actuator cap) may cover the second end 30 of the housing 12 to prevent accidental actuation of the activation button 32.

The second cap 34 may have a distinctive color to differentiate the first end 20 and second end 30 of the device, though one skilled in the art will recognize that the cap 34 and housing 12 may have any suitable color, size and configuration.

In the illustrative embodiment of FIGS. 1 and 2, the housing 12 and caps 24 and 34 may further include graphics, symbols and/or numbers to facilitate use of the automatic injection device 10. For example, in the illustrative embodiment, the housing 12 includes an arrow 125 on an outer surface pointing towards the first end 20 of the device to indicate how the device 10 should be held relative to the patient (i.e., with the first end 20 adjacent to the injection site), as shown in FIG. 2. In addition, the first cap 24 is labeled with a "1" to indicate that a user should remove the first cap 24 of the device first, and the second cap is labeled with a "2" to indicate that the second cap 34 should be removed after the first cap 24 is removed during preparation for and subsequent injection using the illustrative automatic injection device 10. One skilled in the art will recognize that the automatic injection device 10 may have any suitable graphics, symbols and/or numbers to facilitate user instruction, or the automatic injection device may omit such graphics, symbols and/or numbers.

As shown in FIG. 2, the first end 20 of the housing 12 may have a wider diameter than the second end 30. A step 29 may be formed at the transition between the two diameters to accommodate the second cap 34 to facilitate seating of the second cap 34 on the second end 30 of the housing.

As illustrated in FIGS. 1 and 2, the housing 12 also preferably includes a display window 130 to allow a user to view the contents of the syringe housed within the housing 12, as described in detail below. The window 130 may comprise an opening in the sidewall of the housing 12, or may comprise a translucent material in the housing 12 to allow viewing of the interior of the device 10.

The housing 12 may be formed of any suitable surgical material, including, but not limited to, plastic and other known materials.

FIGS. 3-5 are schematic views of interior components of an automatic injection device 10 according to one embodiment of the invention. As shown, a syringe 50 or other suitable container for a substance is disposed within the interior of the housing 12. The illustrative syringe 50 includes a hollow barrel portion 53 for holding a dose of a liquid substance to be injected. The illustrative barrel portion 53 is substantially cylindrical in shape, though one skilled in the art will recognize that the barrel portion 53 may have any suitable shape or configuration. A seal, illustrated as a bung 54, seals the dose within the barrel portion 53. The syringe 50 may further include a hollow needle 55 connected to and in fluid communication with the barrel portion 53, through which the dose can be ejected by applying pressure to the bung 54. The hollow needle 55 extends from a first, proximal end 53a of the barrel portion 53. The second end 53b of the barrel portion 53 includes a flange 56, or other suitable mechanism, for abutting a stop, represented schematically as 123, in the housing 12 to limit the movement of the syringe 50 within the housing 12, as described below. One skilled in the art will recognize that the invention is not limited to the illustrative embodiment of the syringe 50 and that any suitable container for containing a dose of a substance to be injected may be used in accordance with the teachings of the invention. In the illustrative embodiment of FIGS. 3-5, the needle 55 is a fixed twenty-seven gauge one-half inch needle. The tip of the illustrative hollow needle 55 may include five bevels to facilitate insertion. However, the needle 55 may have any suitable size, shape and configuration suitable for piercing a user's skin to deliver a substance to a subcutaneous region and is not limited to the illustrative embodiment. Suitable types of needles are well-known in the art.

The automatic injection device 10 shown in FIGS. 3-5 further includes a syringe actuator 70, illustrated as a plunger, for selectively moving and actuating the syringe 50 to inject the dose contained in the syringe 50 into a user. The illustrative plunger 70 includes a rod portion 71 having a first end 71a integral with, connected to or in fluid communication with the bung 54 for selectively applying pressure to the bung 54 to expel the dose from the needle 55. The plunger 70 may include a flanged second end 72.

In an embodiment, the syringe activator comprises multiple components and/or more actuators are present in the automatic injection device of the invention.

The plunger 70 of FIGS. 3-5 is biased forward towards the first end 20 of the device 10 by a first biasing mechanism, illustrated as a coil spring 88 disposed about or above a flanged second end of the plunger 70. In the embodiment illustrated in FIGS. 3-5, a proximate end 88a of the coiled spring 88 abuts the flanged second end 72 of the plunger 70 to selectively apply pressure and move the plunger 70 proximally. Alternatively, the plunger 70 extends through the center of the spring 88. Prior to use of the device 10, the coil spring 88 (or another suitable mechanism) is compressed between the plunger 70 and the housing 12, storing energy. A trigger 91, which is activated by any suitable actuation means, such as the activation button 32 shown in FIGS. 1 and 2, retains the plunger 70 and first biasing mechanism 88 in a retracted, latched position, shown in FIG. 3, the activation button 32 is activated. In the illustrative embodiment, the trigger 91 latches the flanged second end 72 of the plunger 70. When a user activates the activation button 32 or other actuation means, the trigger 91 releases the flanged second end 72 of the plunger 70, allowing the coil spring 88, which applies pressure to the flanged second end 72, to propel the plunger 70 towards the first end of the device 10.

A second biasing mechanism, illustrated as a coil spring 89 in FIGS. 3-5, holds the syringe 50 in a retracted position within the housing 12 prior to use, as shown in FIGS. 1 and 3. In the retracted position, the needle 55 is preferably sheathed entirely within the housing 12. The illustrative syringe coil spring 89 is disposed about the proximal portion of the barrel portion 53 and may be seated in a shelf 121 formed within the housing interior. The top end of the coil spring 89 abuts the flanged second end 56 of the syringe 50. The spring force of the second biasing mechanism 89 pushes the flanged second end 56 of the syringe 50 away from the first end 20 of the housing 12, thereby holding the syringe 50 in the retracted position until activated. Other components of the device 10 may also position the syringe 50 relative to the housing 12.

The first biasing mechanism 88 and the second biasing mechanism 89 may have any suitable configuration and tension suitable for use in biasing certain components of the device. For example, the first biasing mechanism 88 has any suitable size, shape, energy and properties suitable for moving the plunger 70 and syringe 50 forward when released. The second biasing mechanism 89 has any suitable size, shape, energy and properties suitable for retracting the syringe 50 prior to activation. Other suitable means for facilitating movement and expulsion from the syringe may also be used.

Referring still to the illustrative embodiment of FIGS. 3-5, the plunger 70 further includes a compressible expanded central portion 76. In the illustrative embodiment, the rod 71 is split in the central portion to form a pair of projecting elbows 78 that define the compressible expanded central portion 76. The projecting elbows 78 may be pre-formed as part of the molded plunger 70, or may be attached to the plunger 70 separately. The projecting elbows 78 are compressible, so that they can be moved radially inwardly to cause that portion of the rod to adopt a circumference similar to the rest of the rod. The compressible expanded central portion 76 facilitates movement, of the syringe 50, followed by expulsion of the dose in two substantially separate stages, as described below.

As shown in FIG. 4, when an activation means 320 activates the trigger 91 to release the plunger 70, the spring force of the coil spring 88 propels the plunger 70 forward (proximally). During a first operational stage, the moving plunger 70 pushes the syringe 50 forward, such that the tip of the needle 55 projects from the first end 20 of the housing 12.

The initial biasing force provided by the first coil spring 88 is sufficient to overcome the biasing force of the second coil spring 89 to allow movement of the syringe 50 against the backward biasing force of the second coil spring 89. In the first operational stage, the expanded region 76 of the plunger 70, formed by the projecting elbows 78, rests against the second end 56 of the barrel portion 53, preventing the plunger 70 from traveling within the syringe barrel portion 53. In this manner, all biasing force from the first coil spring 88 is applied to move the syringe 50 forward towards the first end 20 of the device 10.

The activation means 320 illustrated in FIGS. 3-5 may have any suitable size, shape, configuration and location suitable for releasing the plunger 70 or otherwise activating the device 10. For example, still referring to FIG. 2, the activation means 320 may be an activation button 32 formed on a distal end 30 of the housing 12, or may comprise another suitable device, such as a latch, twist-activated switch and other devices known in the art. While the illustrative activation means 320 is located towards a distal end 30 of the device 10, one skilled in the art will recognize that the activation means 320 may be positioned in any suitable location on the device 10.

The forward motion of the syringe 50 towards the proximal end 20 of the device 10 continues against the biasing force of the coil spring 89 until the flanged end 56 of the barrel portion 53 abuts a stop 123, such as a protrusion or flange, on the housing 12, as shown in FIG. 4. One skilled in the art will recognize that alternate stopping or limited mechanisms may be employed and that the invention is not limited to the illustrative stopping mechanism.

As shown in FIG. 4, the first operational stage propels the tip of the needle 55 through the opening 28 at the first end 20 of the device 10, so that the needle 55 may pierce the skin of a patient. During this stage, the syringe barrel portion 53 preferably remains sealed without expelling the substance through the needle 55. The interference caused by the stopping mechanisms 56, 123 maintains the needle 55 in a selected position extending from the proximal open end 28 of the device 10 during subsequent steps. Until the stopping mechanisms 56, 123 stop the movement of the syringe 50, the compressible expanded central portion 76 of the plunger 70 prevents movement of the plunger 70 relative to the barrel portion 53.

The stops 56, 123 may be positioned at any suitable location relative to the open first end 20 to allow the syringe 50 to penetrate the skin by any suitable depth suitable for an injection.

In the second operational stage, which commences after the stopping mechanism 123 housing 12 catches the flanged portion 56, or other stopping mechanism, stopping further movement of the barrel portion 53, the continued biasing force of the coil spring 88 continues to push the plunger 70 relative to the housing 12, as shown in FIG. 5. The biasing force causes the elbows 78 of the plunger 70 to compress radially inward and slide into the interior of the barrel portion 53. While the interference between components 123 and 56 retains the barrel portion 53 in a selected position (with the needle exposed) and with the elbows 78 in a collapsed stage, the coil spring 88 pushes the plunger 70 within the barrel portion. After the plunger 70 overcomes the necessary force to allow the elbows 78 to compress and extend into the barrel portion 53, the plunger 70 applies pressure to the bung 54, causing ejection of the contents of the syringe 50 through the projecting needle 55. Because the first operational stage has displaced the needle 55 into the skin, the contents of the barrel portion 53 are injected directly into a subcutaneous region of the patient.

Referring to FIG. 6, in one embodiment of the invention, the automatic injection device 10 may comprise two interlocking components: a syringe housing assembly 121 containing the proximal components of the device 10 (e.g., the syringe barrel 53, coil spring 89, needle 55 and other proximal components), and a firing mechanism assembly 122 containing the distal components of the device (e.g., the means for actuating the syringe). The syringe housing assembly 121 and the firing mechanism assembly 122 may be coupled through any suitable means. In the illustrative embodiment, a proximal end 122a of the firing mechanism assembly 122 may be sized and configured to be inserted into a distal end 121b of the syringe housing assembly 121. In addition, one or more tabs 127 (shown in detail in FIGS. 7, 8A-8C, and 9) on the proximal end 122a of the firing mechanism assembly 122 may snap-fit into corresponding openings 126 on the distal end 121b of the syringe housing assembly 122 to ensure alignment and coupling of the two assemblies 121, 122 and the components housed therein.

Figure 7:
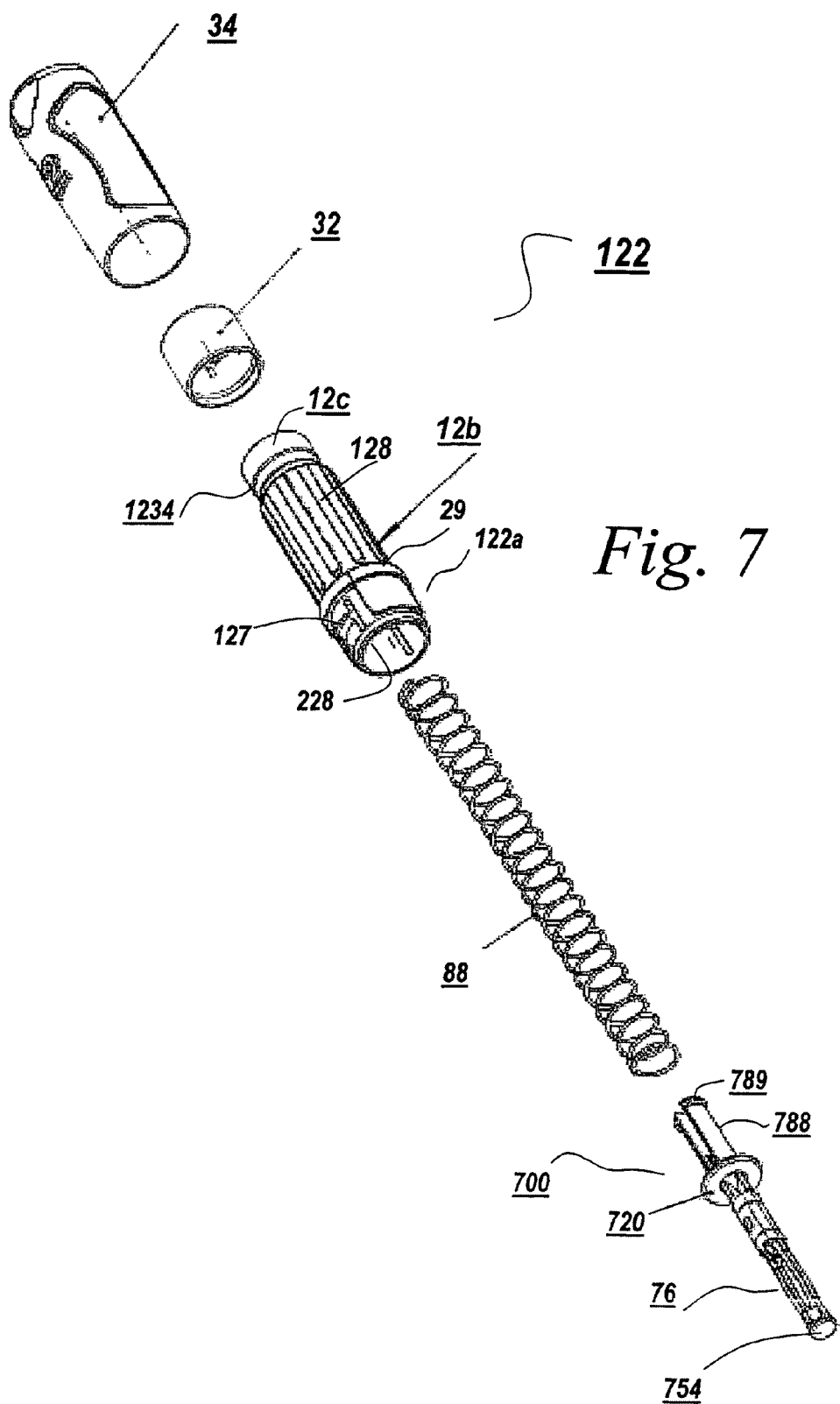
FIG. 7 is an exploded view of the firing mechanism assembly of the automatic injection device of FIG. 6 according to an illustrative embodiment of the invention.

FIG. 7 is an exploded view of the firing mechanism assembly 122 according to an illustrative embodiment of the invention. As shown, the firing mechanism assembly 122 includes the illustrative activation button 32, the illustrative actuator cap 34, an illustrative distal housing component 12b (firing body) and a coil spring 88 or other biasing mechanism. The illustrative firing mechanism assembly 122 further includes a syringe actuator, illustrated as a syringe actuation component 700, that extends from the proximal end 122a of the distal housing component 12b for moving the syringe 50 in a first stage and actuating the syringe 50 to expel its contents in a second phase.

Figure 8A:
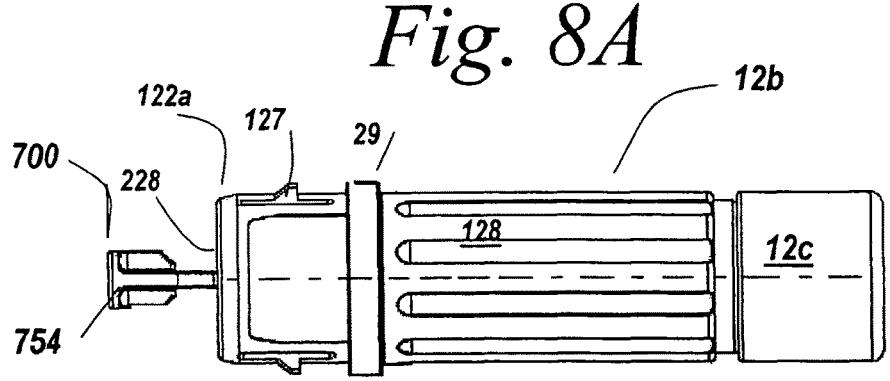
FIGS. 8A-8C are different views illustrating the distal housing component, coil spring and syringe actuation component of the firing mechanism assembly of FIG. 7 when assembled without the activation button.
Figure 8B:
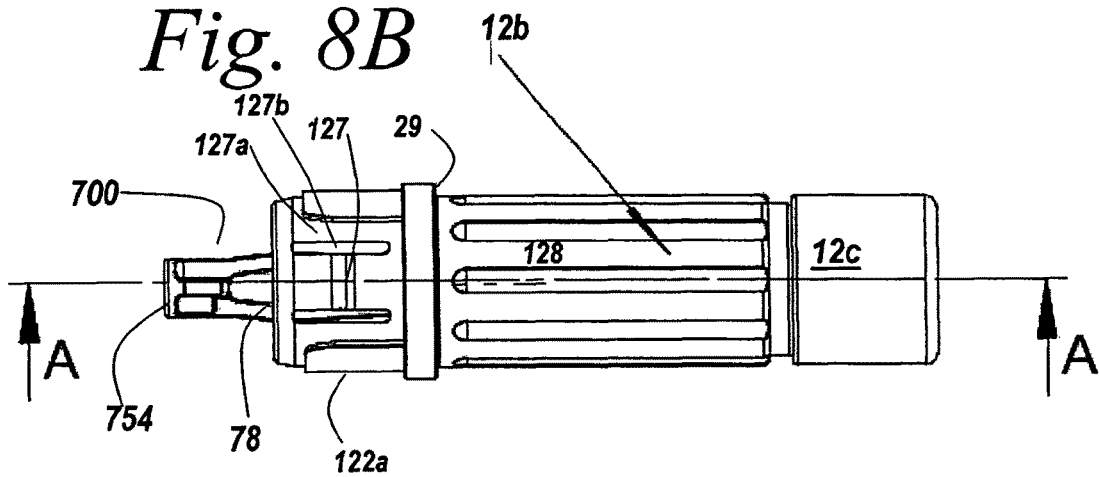
Figure 8C:
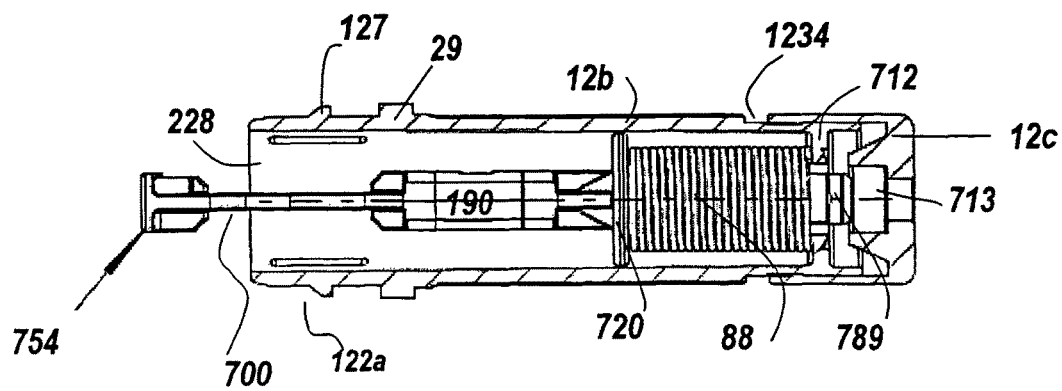
Figure 9:
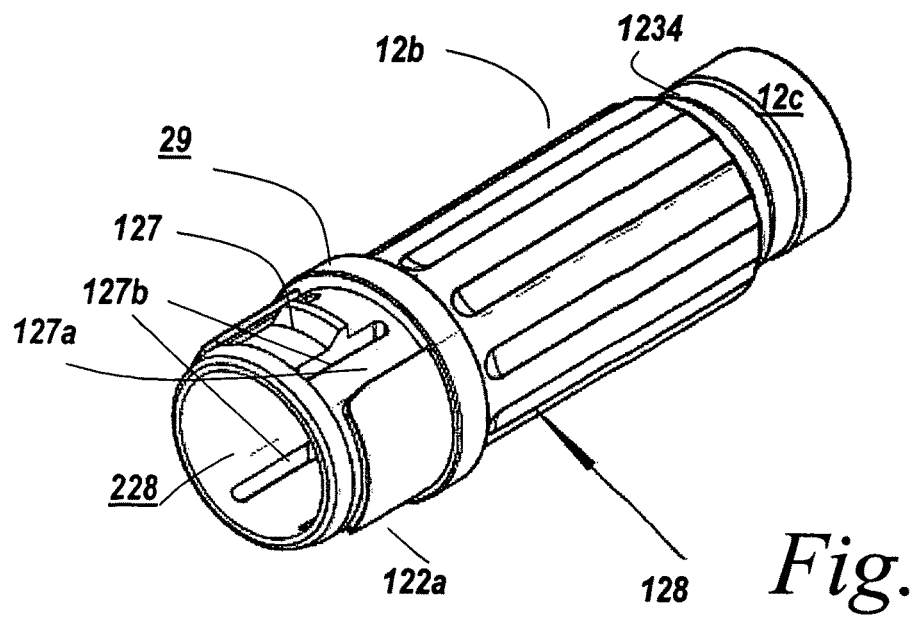
FIG. 9 is a perspective view of the distal housing component of the firing mechanism assembly of FIG. 7.

FIGS. 8A-8C illustrate the distal housing component 12b, coil spring 88 and syringe actuation component 700 when assembled without the activation button 32. FIG. 9 is a perspective view of the distal housing component 12b and FIG. 10 is a perspective view of the syringe actuation component 700 according to illustrative embodiments of the invention.

As shown in FIGS. 1-2 and 7-9, the distal housing component 12b includes a substantially tubular body, which may include contours 128 to facilitate gripping of the device 10 by a user. A step 29 may be formed in a distal region 30 to facilitate seating of the actuator cap 34, as described above. Forward of the step 29, the distal housing component 12b has a size and shape configured to be inserted into the distal end of the syringe housing 121. Tabs 127 are formed to facilitate coupling and/or locking of the two housing components 12a and 12b together. As shown in FIG. 9, the tabs 127 may be formed in a depression 127a on the surface of the proximate end of the distal housing component 12b, and may also or alternatively include ribs 127b for guiding the tabs into a locking position relative to the proximate housing component 12a. One skilled in the art will recognize that any suitable means for coupling the two assemblies together may be used and that the invention is not limited to the illustrative coupling means.

As shown in FIGS. 2 and 8C, the distal housing component 12b may include an anchoring cap 12c coupled to a smaller diameter distal end of the distal housing component 12b for anchoring the firing mechanisms for actuating the device 10 to the distal housing component 12b. The interface of the anchoring cap 12c and the distal housing component 12b may form a groove 1234 to facilitate a snap fit of the activation button 32 on the distal end of the distal housing component 12b, or may be joined by other suitable joining means as described above.

Figure 10:
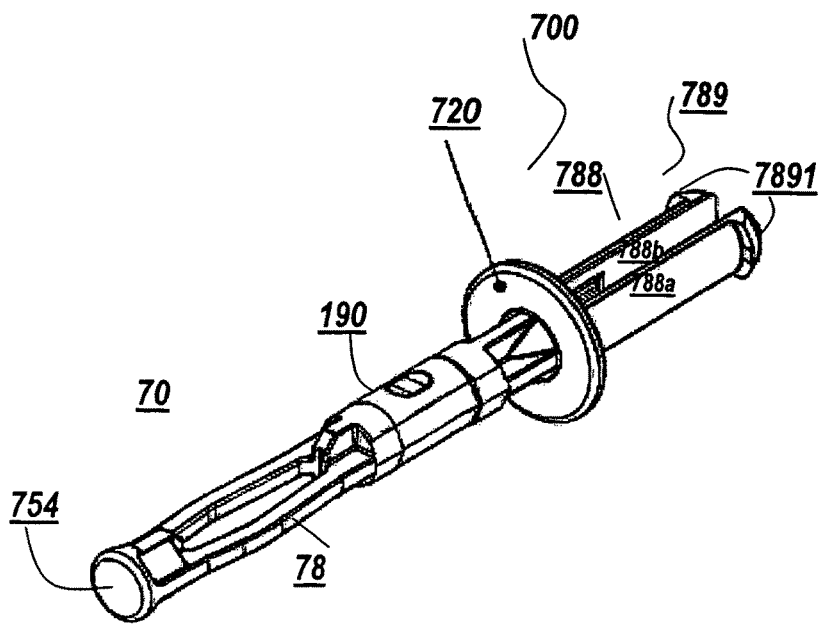
FIG. 10 is a perspective view of the syringe actuation component of the firing mechanism assembly of FIG. 7.

Referring to FIGS. 3 and 10, the syringe actuation component 700 is preferably an integrated component formed of any suitable material, such as an acetal-based plastic, though other suitable materials may also be used. The syringe actuation component 700 comprises a pressurizing end 754 for applying pressure to the bung 54 of a corresponding syringe 50, a plunger rod portion 70 with a compressible expanded central portion, illustrated as the plunger elbows 78, as well as other components, such as components for anchoring the coil spring 88 to the syringe actuation component 700, as described below. The compressible expanded central portion 76 facilitates movement of a corresponding syringe 50 into a protracted position and expulsion of the contents of the syringe 50 in two separate steps, as described above. Alternatively, the syringe actuator may comprise multiple actuators for moving and/or promoting expulsion of the syringe 50.

The syringe actuation component 700 of FIGS. 2 and 10 further may include an indicator 190 in a solid rod portion 70 distal from the elbows 78. During operation of the device 10 and after completion of an injection, the indicator 190 is configured to align with the window 130 on the housing 12 to indicate completion of the injection. The indicator 190 preferably has a distinctive color or design to represent completion of an injection.

As shown in FIGS. 2, 7, 8C and 10, the illustrative syringe actuation component 700 further includes a retaining flange 720 for holding the actuating coil spring 88 in a compressed position until actuation. The retaining flange 720 is sized, dimensioned and formed of a material that preferably allows the syringe actuation component 700 to slidably and easily move within the housing 12 when the device 10 is actuated. Extending distally from the retaining flange 720, the syringe actuation component 700 forms a base 788 for the actuating coil spring 88. The base 788 terminates in a trigger anchoring portion 789. The illustrative base 788 may comprise flexible legs 788a, 788b around which the spring 88 coils. The trigger anchoring portion 789 may comprise tabbed feet 7891 extending from the base 788 and configured to selectively engage the anchoring cap 12c and/or distal housing component 12b. The activation button 32 coupled to the distal end of the distal housing component 12b is configured to hold the trigger anchoring portion 789 until activation. When activated, the activation button 32 releases the trigger anchoring portion 789, allowing the coil spring 88 to propel the syringe actuation component 700 towards the proximal end 20 of the device 10 in an operation described above.

In a retracted, anchored position shown FIGS. 2, 8C and 10 (corresponding to the schematic of FIG. 3), the trigger anchoring portion 789 interacts with the housing 12, which holds the tabbed feet 7891 in a latched position, against the biasing force of the coil spring 88, to maintain the syringe actuation component 700 in a retracted position. In this position, the flange 720 retracts the spring 88 against the back, distal wall 712 of the distal housing component 12b. An opening 713 in the anchoring cap 12c allows the activation button 32 access to the anchoring portion 789. In the retracted position, the pressurizer 754 of the syringe actuation component 700 extends out of an opening 228 on the proximal end 122a of the distal housing component 12b. When the distal housing component 12b couples to a corresponding syringe actuation mechanism 121, the pressurizer 754 extends into the barrel portion of a syringe housed therein. The pressurizer 754 may be integral with, the same as, connected to, or otherwise in communication with the bung 54 of a syringe 50 housed in the device 10 and may have any suitable size, shape and configuration suitable for applying pressure to the bung 54. In one embodiment, the pressurizer 754 has a cross-section corresponding to the shape of the barrel portion 53 of a corresponding syringe 50 so as to substantially seal the barrel portion 53, and the pressurizer 754 is configured to slidably move within the barrel portion 53 to apply pressure to the bung 54 and actuate the syringe 50.

In the illustrative embodiment of FIGS. 7-10, the syringe actuation component 700 constitutes a single, integrated mechanism for anchoring a corresponding syringe 50, spring 88 and other components, actuating and moving the syringe 50 to a protracted position, and separately expelling the contents of the syringe 50.

Figure 11:
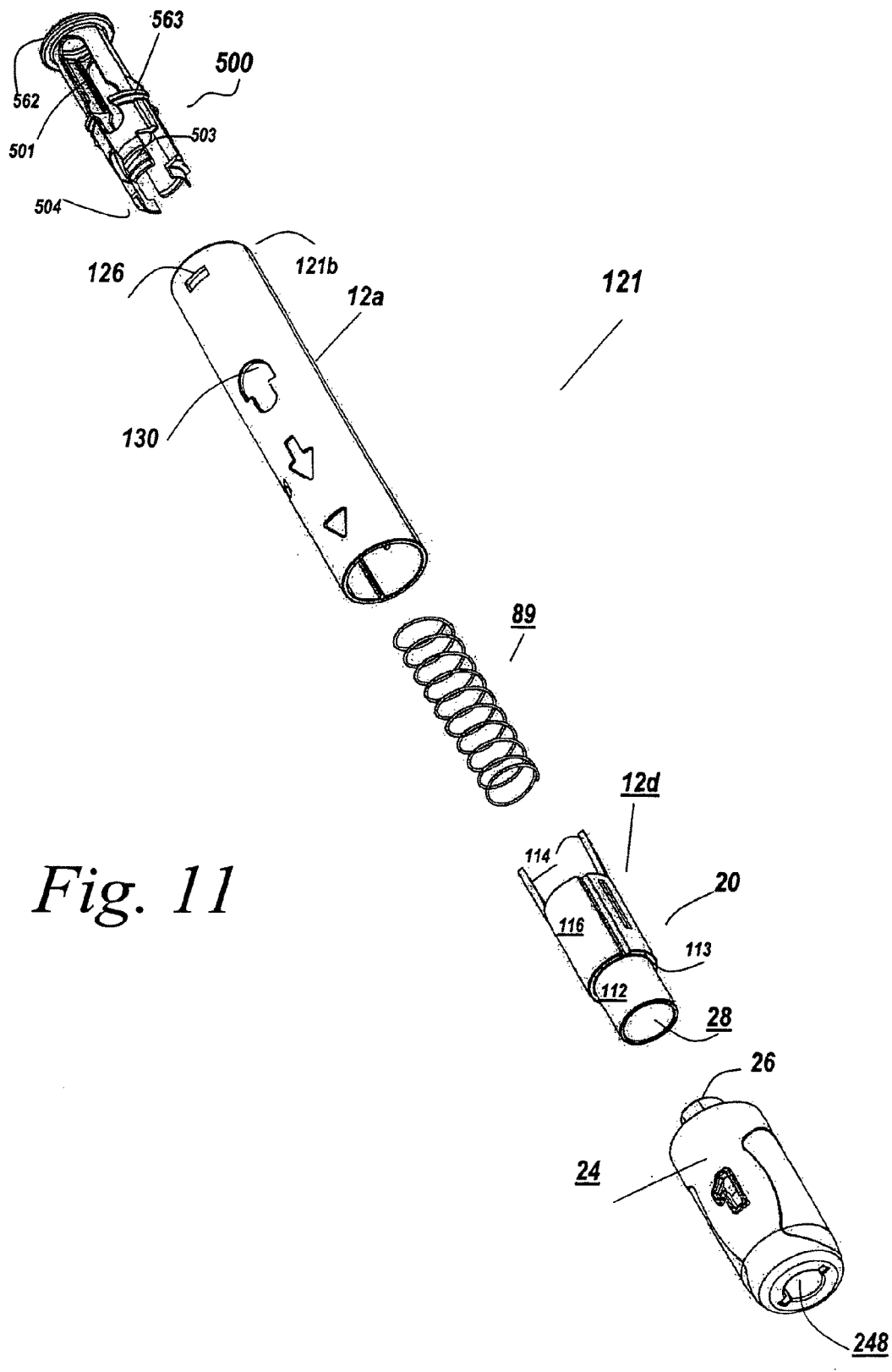
FIG. 11 is an exploded view of the syringe housing assembly of the automatic injection device of FIG. 6 according to an illustrative embodiment of the invention.

FIG. 11 is an exploded view of the syringe housing assembly 121 of an illustrative embodiment of the invention, which is configured to couple to and interact with the firing mechanism assembly 122 of FIGS. 7-10. The illustrative syringe housing assembly 121 includes a proximal housing component 12a, the proximate cap 24, a proximal, second biasing mechanism 89, a syringe carrier 500 and a stepped shroud 12d forming a proximate portion 20 of the housing 12 when assembled and includes the proximate opening 28, as also shown in FIG. 2. The components 12a, 12d, 89, 500 and 24 cooperate to house a syringe 50 containing a substance to be injected and facilitate operation of the device 10 in the two different operational stages as described above.

Figure 12:
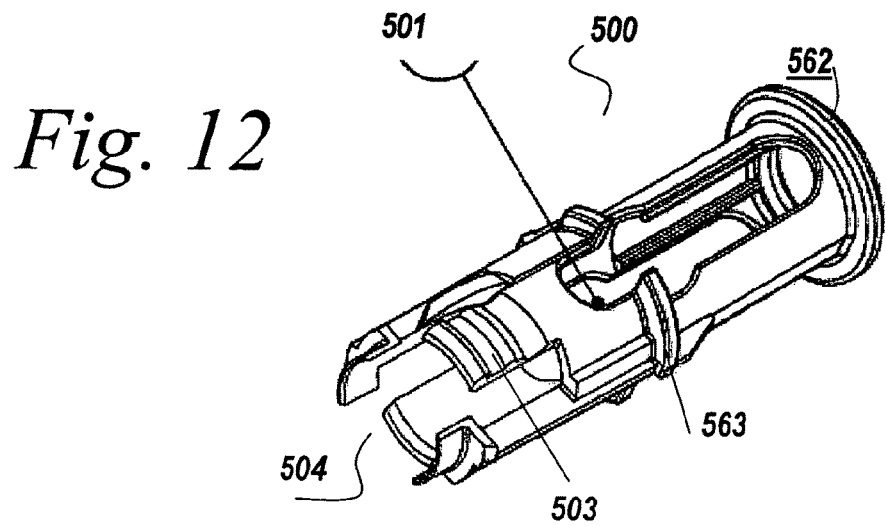
FIG. 12 illustrates an embodiment of the syringe carrier of the syringe housing assembly of FIG. 11.
Figure 13:
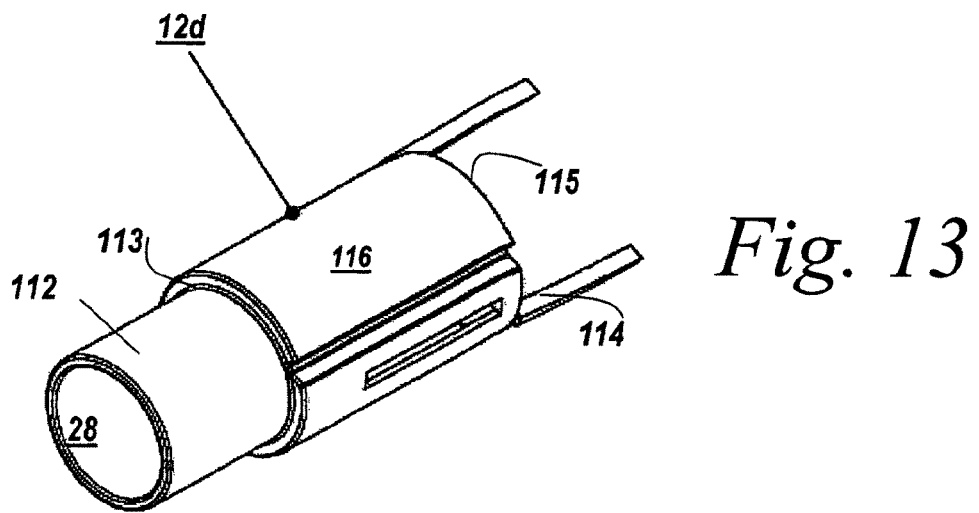
FIG. 13 illustrates an embodiment of the stepped shroud of the syringe housing assembly of FIG. 11.
Figure 14:
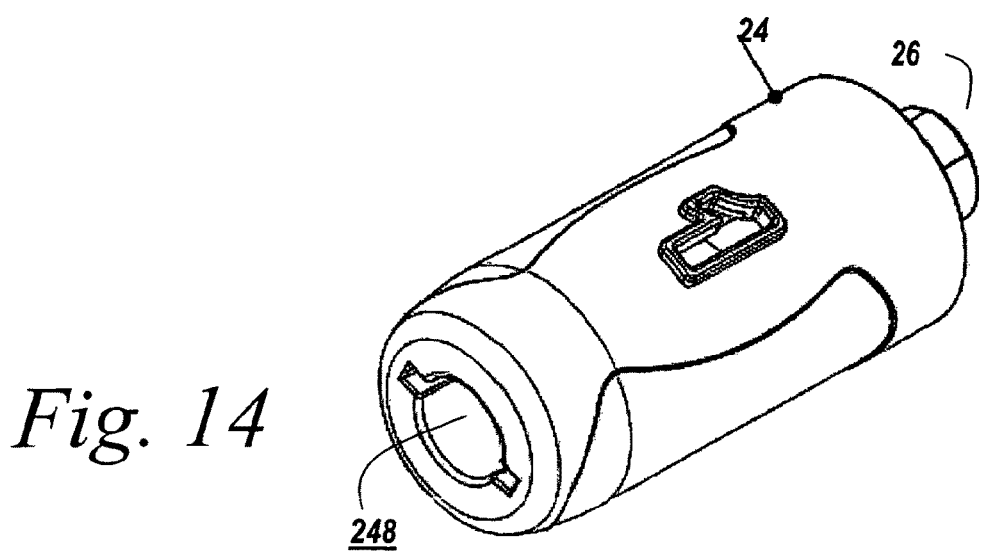
FIG. 14 illustrates an embodiment of the proximate cap of the syringe housing assembly of FIG. 11.
Figure 15A:
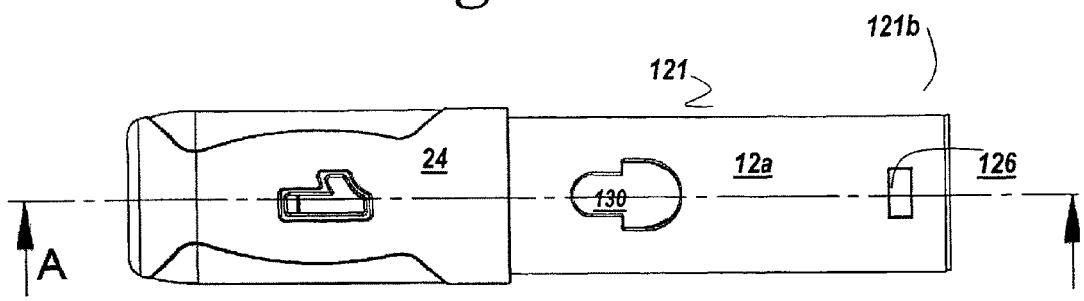
FIGS. 15a and 15b are a perspective side view and a cross-sectional side view, respectively, of the assembled spring housing assembly of FIG. 11 according to one embodiment of the invention.
Figure 15B:
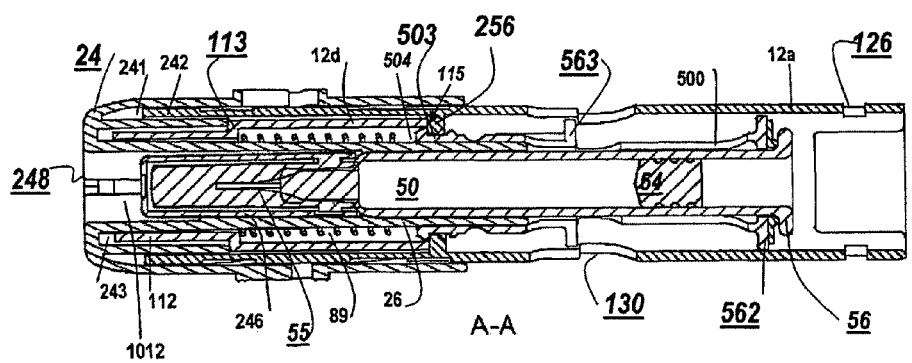

Illustrative embodiments of the syringe carrier 500, the stepped shroud 12d and the proximate cap 24 are shown in detail in FIGS. 12, 13 and 14, respectively. FIGS. 15a and 15b are a perspective side view and a cross-sectional side view, respectively, of the assembled spring housing assembly 121 according to one embodiment of the invention. One skilled in the art will recognize that the invention is not limited to the illustrative embodiments.

Referring now to FIGS. 1, 2, 11, 12 and 15b, the syringe carrier 500 of the illustrative embodiment envelopes the distal half of a syringe 50 used in the device 10. The syringe 50 rests in the carrier 500, and both are contained in the housing 12. During operation, the syringe 50 and carrier 500 move forward (e.g., proximally) within the housing 12. The housing 12 stops and limits the movement of the carrier 500, and the carrier 500 in turn stops and limits the movement of the syringe 50. The illustrative syringe carrier 500 has a substantially tubular structure including window cutouts 501 preferably aligned with the window 130 on the housing 12a to allow a user to view the contents of the syringe 50 prior to operation. The syringe carrier 500 may include a flanged distal end 562 configured to interface with a flanged distal end 56 (shown in FIGS. 3 and 15b) of the syringe 50. The flanged distal end 562 may serve as a damper for the syringe 50. The syringe carrier 500 may further include an intermediate flange 563, which in the illustrative embodiment forms a stop for the syringe 50 that interacts with an interior stop 256 (shown in FIG. 15b) on the proximate housing component 12a to limit forward motion of the syringe 50. The illustrative syringe carrier 500 may further include a proximate anchor portion 503 that limits movement of the syringe 50 in a distal, rearward direction. In the illustrative embodiment, the proximate anchor portion 503 includes a radial groove configured to engage the interior stop 256. A syringe carrier coupler 504 extends forward past the proximate anchor portion 503 to facilitate coupling of the syringe carrier 500 with the distal end of the spring 89 and the stepped shroud 12d, as shown in FIG. 15b. In one embodiment, the syringe carrier 500 is stationary within the housing 12 and the syringe 50 selectively and controllably slides within and relative to the syringe carrier 500. Alternatively, the syringe carrier 500 is slidably disposed within the housing 12 and selectively carries the syringe 50 within the housing 12. The syringe carrier 500 may have any suitable configuration and size suitable for carrying or guiding the syringe 50 within the housing 12.

Referring to FIGS. 13 and 15b, the illustrative stepped shroud 12d forms a proximate end 20 of the housing 12. The illustrative stepped shroud 12d has a substantially tubular body, including a proximate boss 112 defining the proximate opening 28 of the device 10, through which the syringe needle 55 projects during operation of the device 10. A step 113 from the main tubular body portion 116 forms the proximate boss 112 of smaller diameter than the main tubular body portion 116 of the stepped shroud 12d. As shown in FIG. 15b, the step 113 forms a forward stop for the spring 89 to confine the spring 89 and prevent forward movement of the spring 89 towards the proximate end 20 of the device 10. In the illustrative embodiment, shown in FIG. 15b, the distal rim 115 of the stepped shroud 12d abuts the proximate side of the stop 256 of the proximal housing component 12a. Referring now to FIG. 13, distal arms 114 extend from the stepped shroud 12d to lock in the stepped shroud 12d to prevent accidental needle sticks.

Referring to FIGS. 14, 15a and 15b, the interior of the illustrative cap 24 may include a plurality of radial grooves 241, 243 for receiving protruding portions of the stepped shroud 12d and the proximal housing component 12a. For example, as best illustrated in FIG. 15b, a first radially outer groove 241 receives a proximate end of the sidewall 242 of the proximal housing component 12a. A second, radially inner groove 243 receives the proximate end of the boss 112. The cap boss 26 extends into the inner lumen 1012 of the housing 12 and surround the proximal end of a syringe 50 loaded therein when the cap 24 is coupled to the housing 12. In an embodiment, an interior needle cover 246 (shown in FIG. 15b) of the cap 24 sheaths the syringe needle 55. When the cap 24 is removed, the syringe needle 55 is exposed within the lumen 1012 of the housing 12. The cap 24 may also include an opening in a proximal end 248 thereof.

As described above and shown in FIG. 15a, openings 126 in the proximal housing component 12a receive tabs 127 of the firing mechanism assembly 122 to facilitate assembly of the device 10. The window 130 described above for allowing a user to view the contents of a syringe contained in the assembly 121, as well as to view an indicator 190 that fills the window 130 after completion of an injection may be formed in the proximal housing component 12a.

Figure 16A:
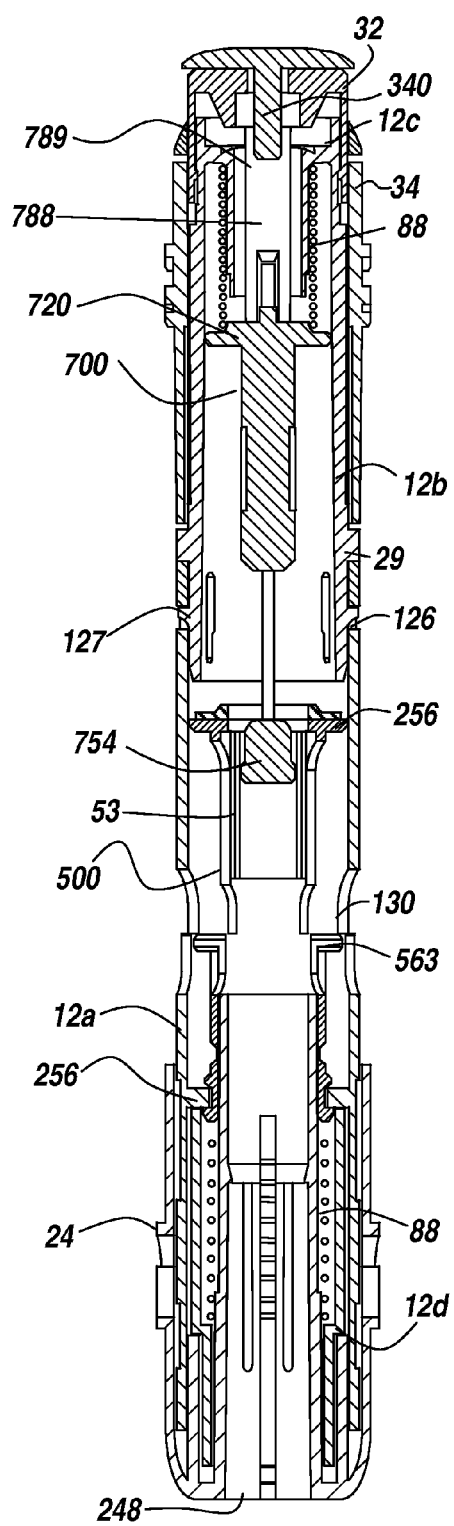
FIGS. 16A and 16B are cross-sectional views at 90 degree offset angles from each other, illustrate an assembled automatic injection device, wherein a syringe housing assembly and a firing mechanism assembly are coupled together.
Figure 16B:
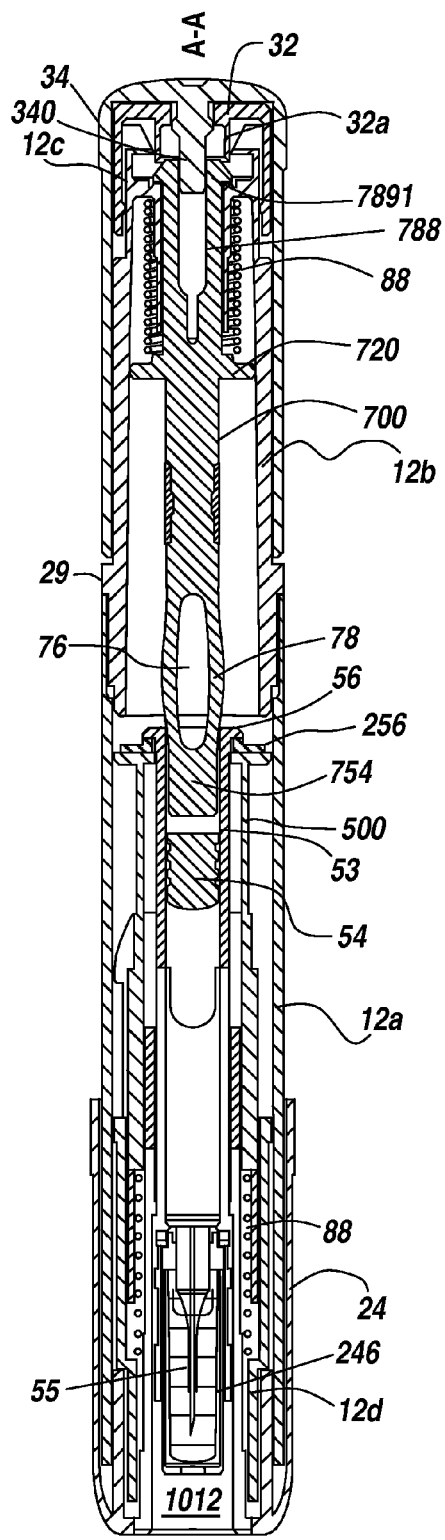

FIGS. 16A and 16B are cross-sectional views at 90 degree offset angles from each other, illustrating an assembled automatic injection device 10, wherein the syringe housing assembly 121 and a firing mechanism assembly 122 are coupled together, such that the pressurizer 754 of the syringe actuation component 700 extends into the barrel portion 53 of a syringe 50 housed in the syringe housing assembly 121 and in communication with a bung 54 of the syringe 50.

As shown, in FIG. 16b the trigger anchoring portion 789 of the syringe actuation component 700 is anchored towards the distal end of the housing 12 by the activation button 32. When a user depresses the activation button 32, driving arms 32a connected to the activation button 32 compress the tabbed feet 7891 of the trigger anchoring portion 789, releasing the syringe actuation mechanism 700 and releasing the spring 88.

Prior to operation, the compressible expanded central portion 76, illustrated as elbows 78, of the syringe actuation component 700 rests above the flange 56 of the syringe 50 to allow the compressible expanded central portion 76, when pushed by a released coil spring 88, to apply pressure to the syringe barrel portion 53, thereby moving the syringe 50 forward within the housing 12 when actuated. As described above, once a stop, such as a stop 256 on the proximal housing component 12*a* shown in FIG. 15*b* and FIG. 16*a*, catches the syringe and halts additional forward motion of the projecting syringe 50, the continued biasing force on the spring 88 will continue to move the syringe actuation component 700 forward, causing the compressible expanded central portion 76 to compress and move into the barrel portion 53 of the syringe 50. The forward motion of the syringe actuation component 700 within the barrel portion 53 causes the pressurizer 754 to apply pressure to the bung 54, causing expulsion of the syringe contents into an injection site.

As also shown in FIGS. 16*a* and 16*b*, the actuator cap 34 may include a stabilizing protrusion 340 that extends through the activator button 32 and between the feet tabbed 7891 of the syringe actuation component 700 to stabilize the components of the device prior to activation.

Figure 17:
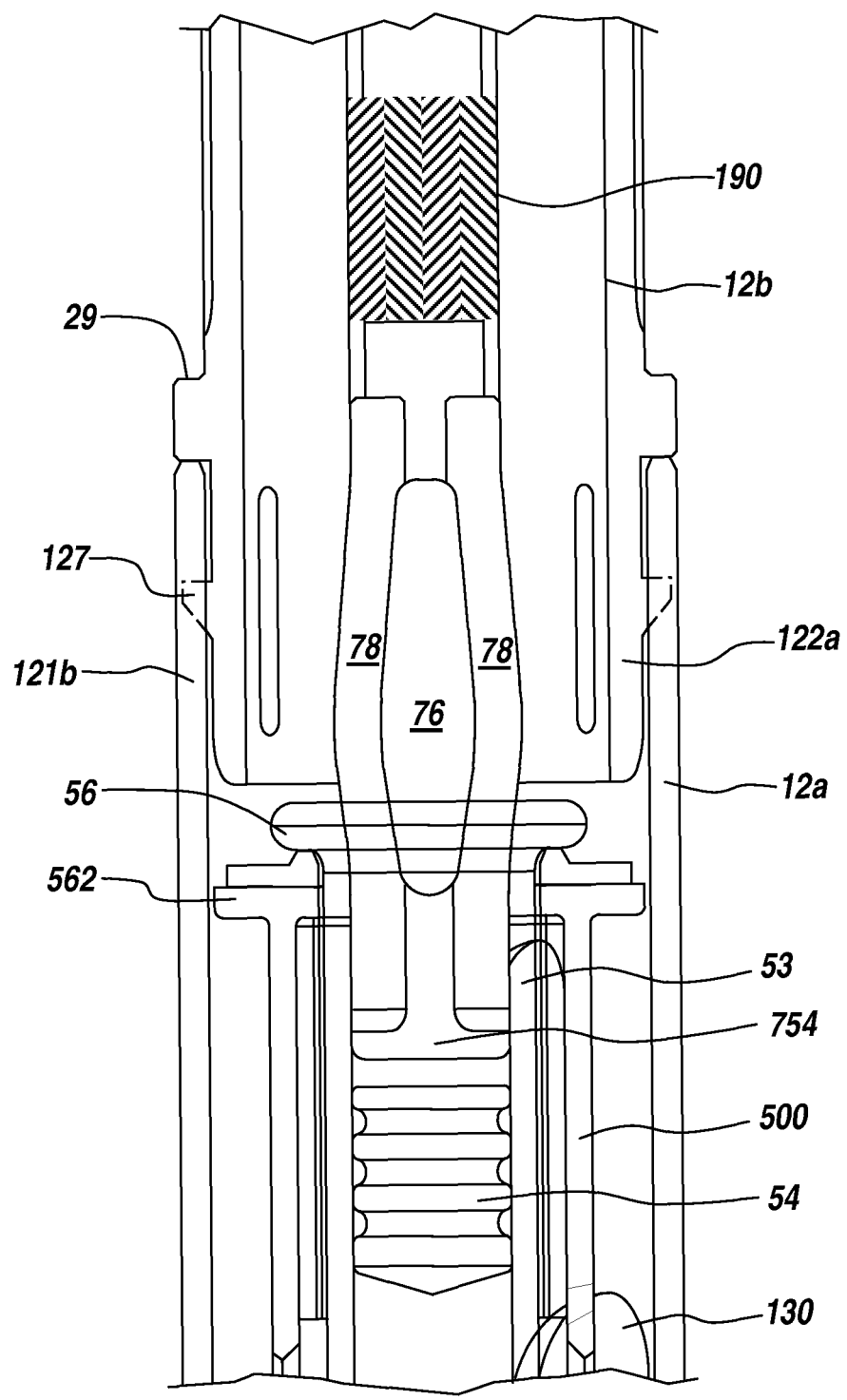
FIG. 17 is a detailed view of the interface between a syringe housing assembly and a firing mechanism assembly of an automatic injection device of an embodiment of the invention, illustrating the indicator of the syringe actuation component according to one embodiment of the invention.
Figure 18:
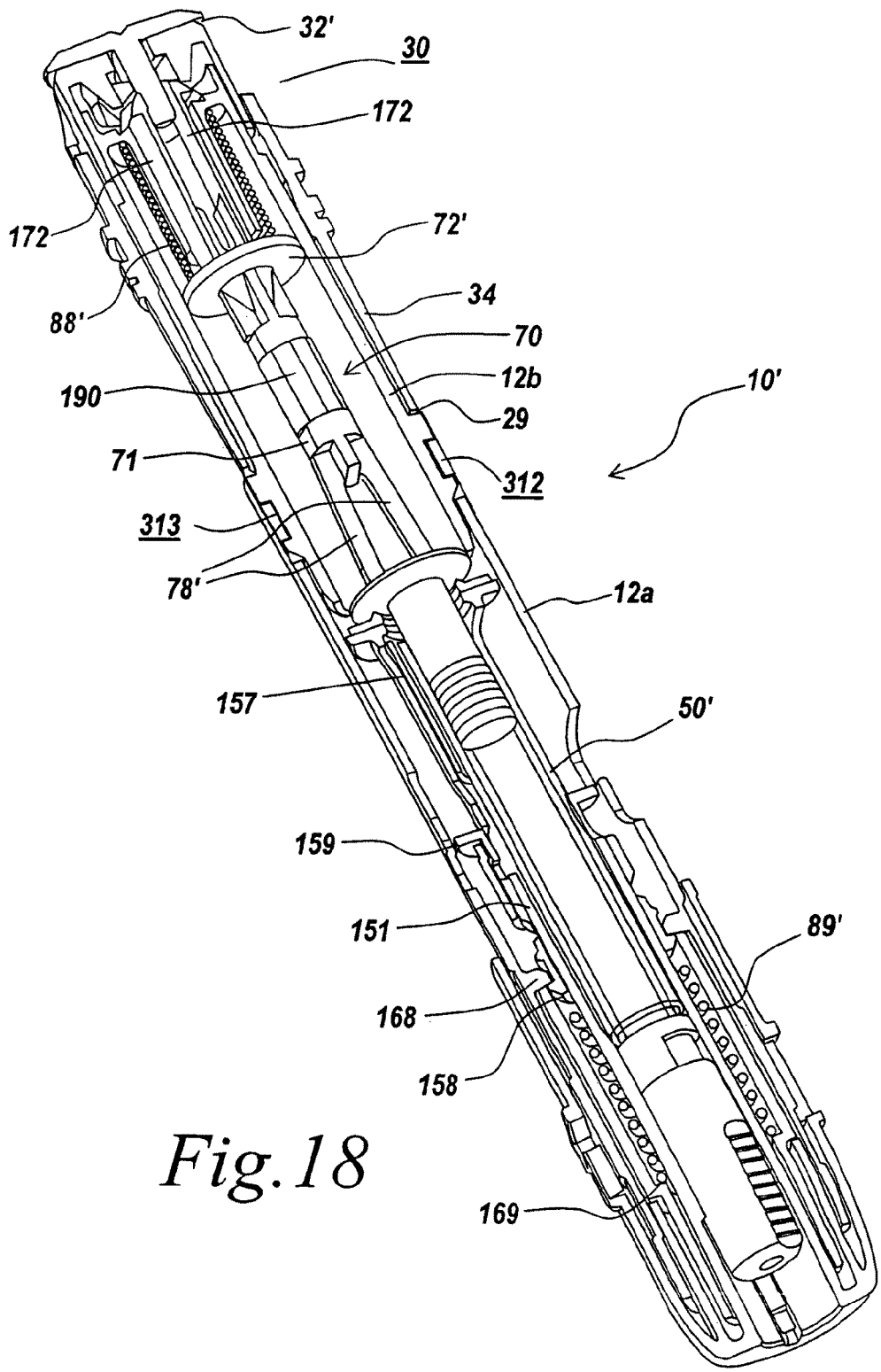
FIGS. 18-22 are cross-sectional view of an automatic injection device according to another embodiment of the invention.

FIG. 17 is a detailed view of the interface between a syringe housing assembly 121 and a firing mechanism assembly 122 (referring to FIGS. 6 and 8*a*) of an automatic injection device 10 of an embodiment of the invention, illustrating the indicator 190 of the syringe actuation component 700 according to one embodiment of the invention. The indicator 190 may have a distinctive color and/or design to indicate to a user that an injection is complete. Also referring to FIG. 2, the indicator 190 is configured to align with the window 130 of the housing 12 after the syringe actuation component 700, with the compressible expanded central portion 76 collapsed and moved forward within the barrel portion 53, completes an injection and fully or substantially fully expels the contents of the syringe 50 out of the needle 55 and into a patient. Thus, prior to operation of the device 10, the syringe barrel 53 aligns with the window 130 and the contents are viewable therein. After injection, with the syringe barrel portion 53 has moved towards the proximal end 20 of the device 10, such that the needle 55 protrudes from the proximal end 20 into an injection site, and the syringe actuation component 700 has moved forward within the syringe barrel portion 53, the indicator 190 aligns with the window 130 to indicate completion of an injection. Therefore, even if the first stage of operation (movement of the syringe 50 into an exposed position with the needle 55 protruding) is complete, the indicator 190 will not align with the window 130 or otherwise indicate completion of an injection until the syringe actuation component 700 has pushed the contents of the syringe 50 out of the barrel 53.

FIGS. 18-22 are cross-sectional views of an assembled automatic injection device 10' according to an illustrative embodiment of the invention. The illustrative embodiment of the automatic injection device 10' includes two mating proximal and distal housing components 12*a*, 12*b*. The proximal and distal housing components 12*a*, 12*b* mate to form a complete housing 12. As shown, a proximal housing component 12*a*, forming a proximal end of the housing 12, receives a proximal end of the distal housing components 12*b*. A cooperating projection 312 and groove 313, or a plurality of cooperating projections 312 and grooves 313, facilitate mating of the proximal and distal housing components 12*a*, 12*b* in the illustrative embodiment. Other suitable mating mechanisms may alternatively be employed. A shelf 29 formed on an outer surface of the distal housing component 12*b* may form a stop for the second removable cap 34.

Figure 20:
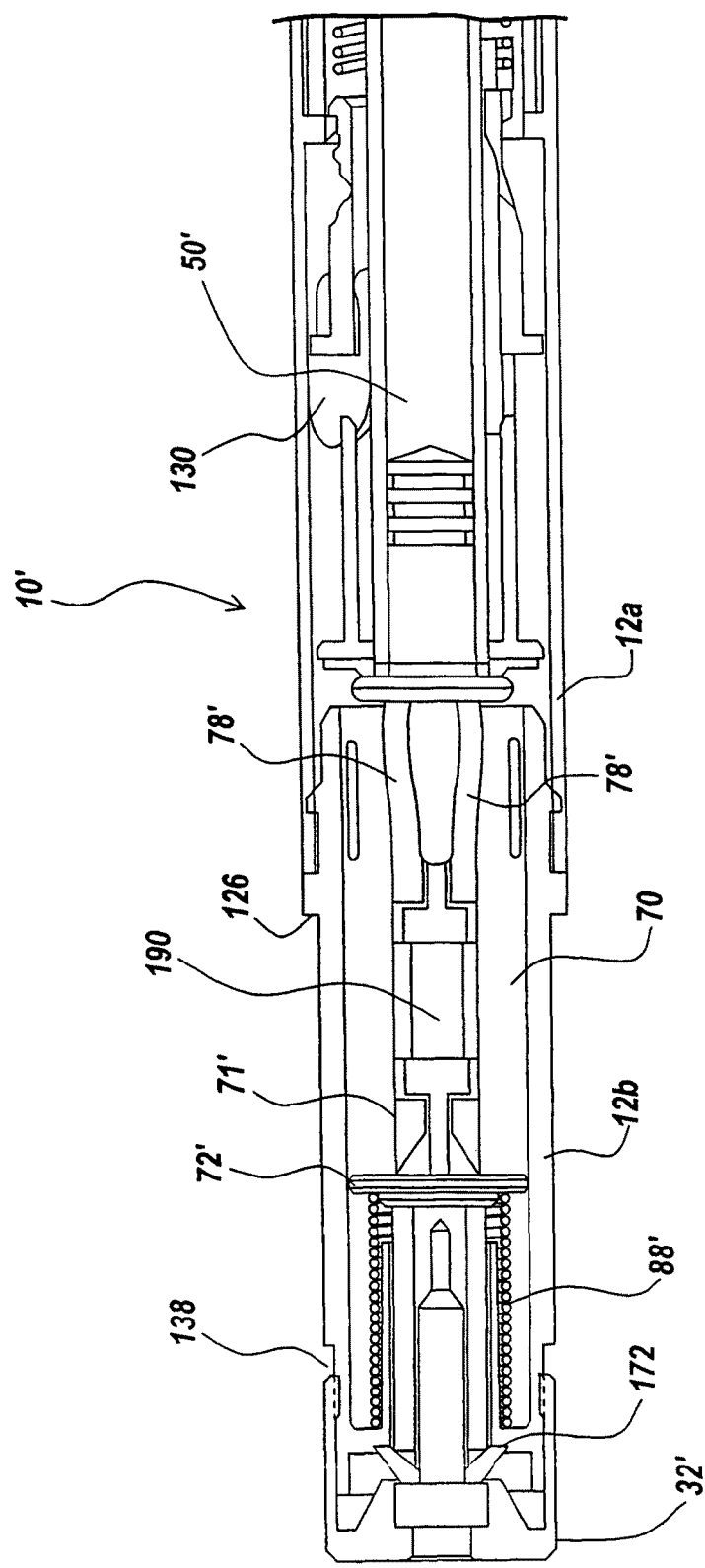
Figure 21:
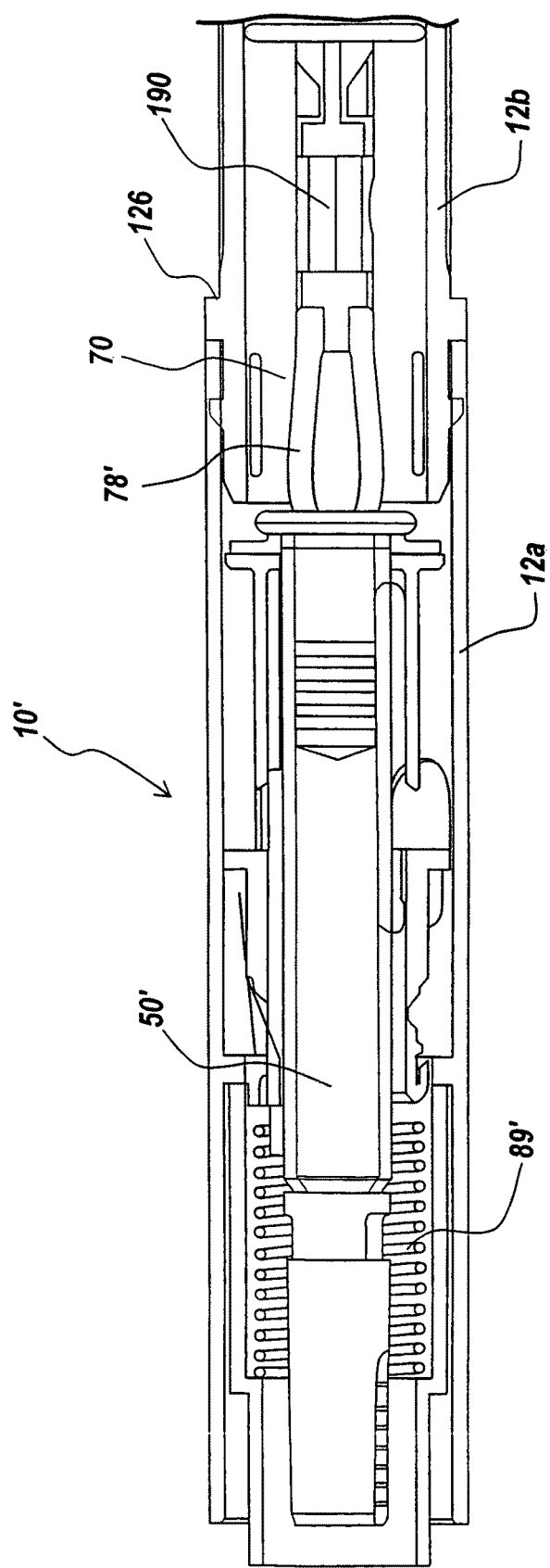
Figure 22:
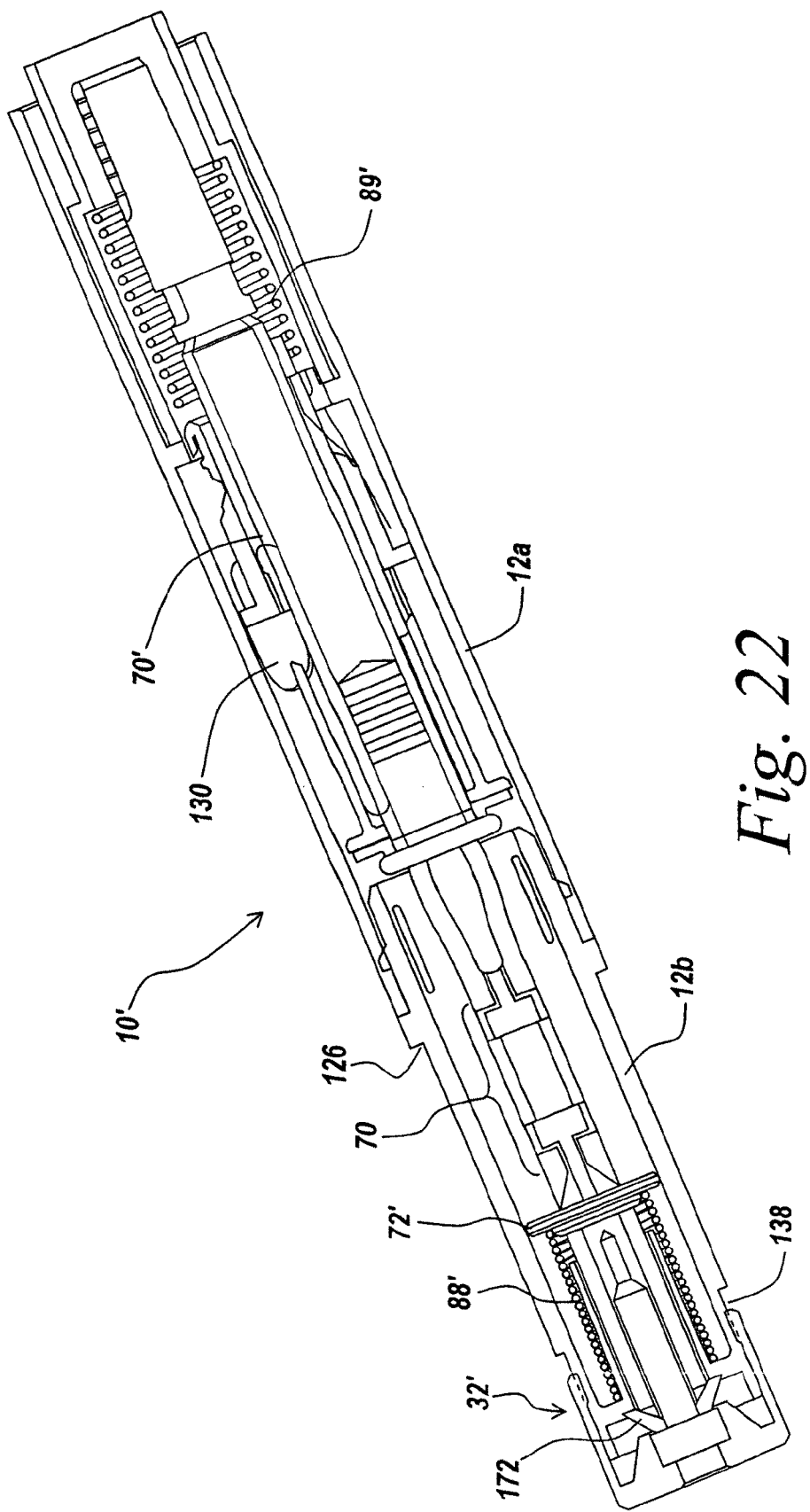

As shown, the activation button 32' may be a cap covering the distal end of the distal housing component 12*b*. The illustrative activation button 32' slides relative to the distal housing component 12*b* to actuate a syringe actuator, such as the plunger 70 or syringe actuation component 700. A shelf/step 138 formed on the outer surface of the distal housing component 12*b* near the distal end 30 of the distal housing component 12*b* allows for and limits the movement of the activation button 32' relative to the housing 12, as shown in FIGS. 20 and 22. The illustrative activation button 32' releasably retains flexible anchoring arms 172 of the plunger 70'. When depressed, the activation button 32' releases the flexible anchoring arms 172 to allow a first biasing mechanism, illustrated as spring 88' to propel the plunger 70' towards the proximal end of the device 10'.

In the embodiment of FIGS. 18-22, the plunger 70' further includes a flange 72' located between the compressible extended middle portion 78 and the distal end of the plunger rod 71'. A first biasing mechanism 88' is seated between an interior distal end of the housing 12 and the flange 72' to bias the plunger 70 towards the proximal end of the housing 12'. As described above, when the activation button 34' releases the anchoring arms 172, the coil spring 88', or other suitable biasing mechanism propels the plunger 70' towards the proximal end 20 of the device 10.

The illustrative embodiment 10' further includes an indicator 190 formed at an intermediate portion of the plunger rod 71' between the flange 72' and the compressible extended portion 76, illustrated as flexible elbows 78'.

The syringe 50' of FIGS. 18-22 may include protrusions or other suitable component to facilitate controlled movement of the syringe within the housing 12'. For example, with reference to FIG. 18, the syringe 50' includes a sleeve 157 forming a proximal protrusion 158 for abutting a proximal side of a first protrusion 168 formed on an inner surface of the housing 12' for limited movement of the syringe 50' in the distal direction within the housing 12'. The sleeve 157 may also form a flange 159 that may abut the distal side of the first protrusion 168 to limit movement of the syringe 50' in the proximal direction during an injection.

Figure 19:
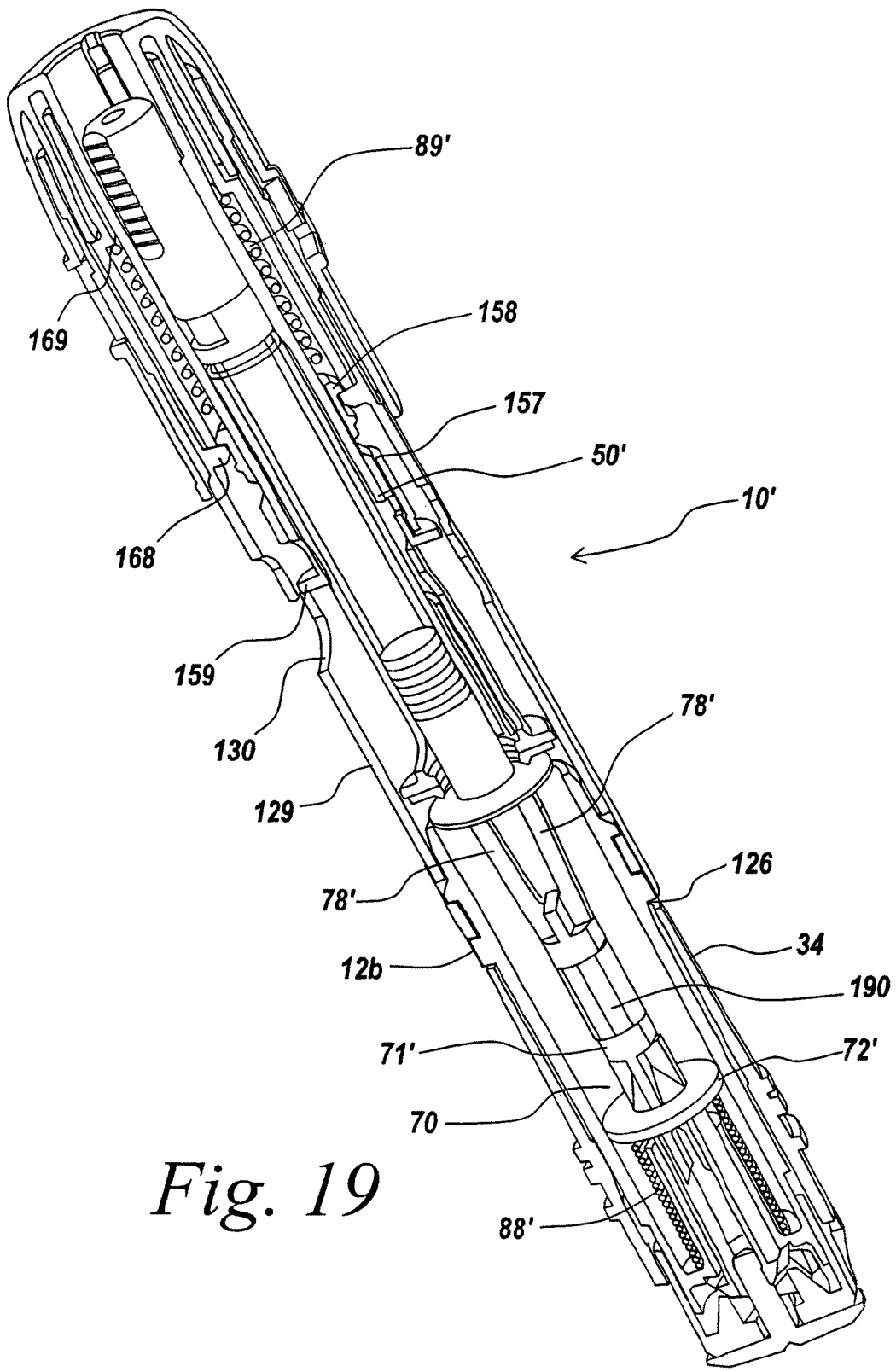

In the embodiment of FIGS. 18-22, the second biasing mechanism, illustrated as coil spring 89' is disposed about a proximal portion of the syringe 50'. A shelf 169 formed at a proximal inner surface of the housing 12' receives a proximal end of the coil spring 89'. Referring to FIG. 19, the proximal protrusion 158 of the syringe sleeve 157, or another suitably disposed mechanism, receives the distal end of the coil spring 89'. As described above, the second biasing mechanism 89' biases the syringe 50' in a retracted position within the housing 12' until activation of the device 10.

As shown in FIGS. 18-22, the automatic injection device 10' incorporates an indicator 190 to indicate to the user of the device 10 when the dose from the syringe 50 has been fully or substantially fully ejected. In the illustrative embodiment, the indicator 190 is formed on a portion of the plunger rod 71' between the compressible expanded central portion 76 and the flange 72'. As the plunger rod 71 moves during operation, the indicator 190 advances towards and aligns with window 130 as the dose empties from the syringe. The indicator 190, which is preferably a different color or pattern from the substance being injected, fills the window 130 entirely to indicate that the dosage has been ejected. Any suitable indicator may be used.

After injection of the dose from the device 10 via the needle 55, a needle sheath 112, which may be formed by the proximal end 20 of the shroud 12*d* may automatically advance over the exposed needle 55 extending from the housing proximal end 20 to prevent accidental sticks.

Figure 23:
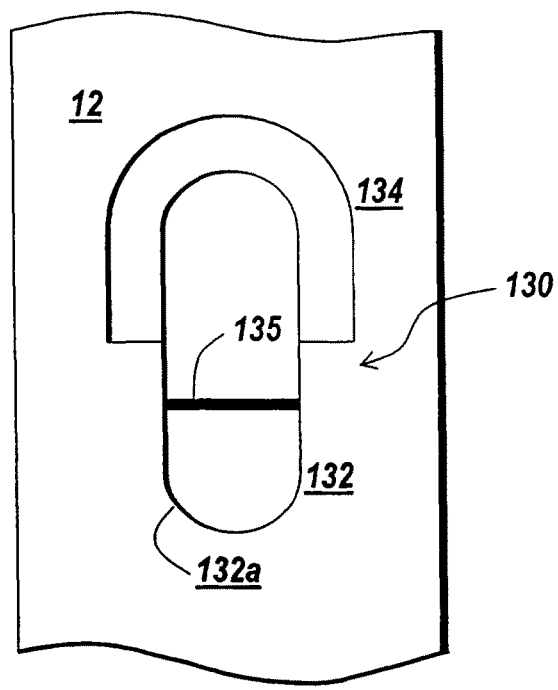
FIG. 23 is a detailed view of the display window of an automatic injection device according to one embodiment of the invention.

Referring to FIG. 23, the illustrative housing 12 includes a window 130 formed through a side wall of the housing 12 to allow a user to view the contents of the syringe.

The illustrative window 130 preferably has a keyhole shape. For example, the window 130 includes a first end 132 that is substantially linear, and may include a curved inner edge 132a. The second end 134 of the window 130 may be substantially hemispherical in shape and wider than the first end 132 of the window 130. The window 130 may include a fill line 135 to allow verification of the proper dosage within the syringe.

According to one embodiment of the invention, the illustrative automatic injection device may be used to deliver a dose of a TNF inhibitor used to treat arthritis and other diseases. In one embodiment, the solution contained in the syringe 50 or 50' contains 40 milligrams of drug product (TNFα blocker or inhibitor), 1 mL of adalimumab: 40 mg adalimumab, 4.93 mg sodium chloride, 0.69 mg monobasic sodium phosphate dehydrate, 1.22 mg dibasic sodium phosphate dehydrate, 0.24 mg sodium citrate, 1.04 mg citric acid monohydrate, 9.6 mg mannitol, 0.8 mg polysorbate 50 and water for injection, with USP sodium hydroxide added as necessary to adjust pH to be about 5.2.

Figure 24:
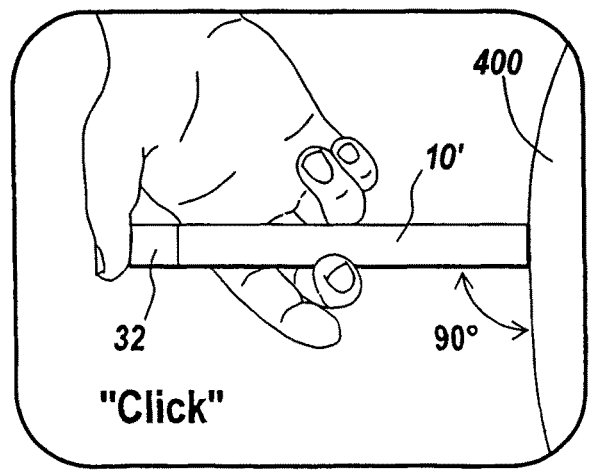
FIG. 24 illustrates use of an automatic injection device of an illustrative embodiment of the invention to inject a drug, such as a TNF inhibitor, into a subcutaneous region of a user.

FIG. 24 illustrates use of the device to deliver a dosage of a substance, such as a TNF inhibitor, to a subcutaneous region of a user according to an illustrative embodiment of the invention. In a first step, a pre-loaded automatic injection device, such as the device 10 or device 10' described above, is provided to a user. Next, the user selects and prepares an injection site 400 for receiving the substance in a subcutaneous region. For example, the user may clean the injection site using a suitable cleaning device, such as an alcohol preparation pad, which may be integrated with the device 10 or 10' of the present invention. Following the preparation, the user prepares the dose for injection. For example, the user may examine the solution through the window 130 to ensure that the solution has a proper color and consistency and that the level of the liquid is at the fill line to ensure proper dosage. After ensuring proper dosage and contents in the pre-filled syringe 50, the user then removes the first cap 24 and second cap 34 of the device 10 or 10' to expose the opening 28 on the first end 20 and the activation button 32 on the second end 30. Then, the user places the automatic injection device 10 or 10' with the open first end 20 adjacent or proximal to the injection site. The user may squeeze the skin in this area to facilitate injection. The automatic injection device 10 or 10' is preferably held at about a ninety-degree angle to the body of the user, flush against the skin, as shown in FIG. 24. After placement, the user presses the activation button 32 to initiate an injection. The depression of the activation button may effect an audible indicator (noise), such as a "click" to indicate initiation of the injection. As described above, depression of the activation button 32 causes the activation button to release the anchor, such as the anchor end 789 of the syringe actuation component 700, allowing a biasing spring 88 to propel the syringe actuation component 700, and thus, the syringe 50 towards the proximal end 20 of the device 10 or 10'. After the syringe 50 pierces the skin, or otherwise enters an administration site, the syringe 50 forward movement stops, which the syringe actuator mechanism, or other mechanism, then pushes on the syringe bung 54 to expel the contents of the syringe 50. The user maintains the automatic injection device 10 or 10' in the position shown in FIG. 24 for a predetermined time period. If an indicator 190 is provided in the automatic injection device 10, the user maintains the automatic injector device 10 in position until the indicator 190 fills the window 130 indicating that a full or substantially full dose of the substance has been injected. Afterwards, the user removes the device 100 to pull the needle 55 out of the skin. The needle 55 is preferably automatically sheathed to prevent accidental pricks. The user may then dispose of the empty automatic injection device 10 or 10'.

According to another embodiment of the invention, a training automatic injection device may be provided for training users how to use the automatic injection device 10 or 10'. The illustrative training injection device mimics the functionality of the automatic training device 10 or 10' without injecting a substance into a patient. The training automatic injection device may have substantially similar components as the automatic injection devices 10, 10' described above, yet lacks a needle and/or a drug. For example, the training automatic injection device may be filled with air that is expelled from the syringe barrel portion 53 when activated. The operation of the training automatic injection device advances the syringe and expels the air or other benign substance, preferably without penetrating the skin of the user. The training automatic injection device preferably includes an indicator, such as indicator 190. The training automatic injection device may help train user to become accustomed to toe handling, sound, feel, operation, use of the indicator 190 and/or timing of the automatic injection device without wasting valuable resources.

The present invention provides significant advantages over prior methods for administering drugs, particularly TNFα inhibitors. For example, the automatic injection device enhances administration, convenience, is less painful, includes a hidden needle to remove apprehension and anxiety for patients who are "needle phobic" to one degree or another so that fear is not a factor. In addition, the automatic injection device efficiently delivers a drug or other substance while being safe. The automatic injection device of the invention also offers safety advantages. Unlike traditional syringes, there is no needle exposure with the automatic injection device. The automatic injection device contains a white needle sleeve that surrounds the needle and protects patients from needlestick injury before and after use. Also, a safety cap on the automatic injection device prevents accidental misfiring, a potential occurrence with prefilled syringes. An audible "click" announces the beginning of the injection, and a distinctive indicator in the inspection window shows the patient that the complete dose was fully administered.

Examples of uses of the automatic injection device of the invention also are described in detail in U.S. Provisional Application Ser. No. 60/818,231, which is expressly incorporated herein by reference in its entirety. Other examples of automatic injection devices are described in PCT/EP2005/002487, which is expressly incorporated herein by reference in its entirety. U.S. Design patent applications Ser. Nos. 29/265,691 and 29/265,646 also describe automatic injection devices, which are also each incorporated herein by reference.

III. TNFα Inhibitors for Use in Compositions and Methods of Invention

The present invention can be used to administer a dose of a substance, such as a liquid drug, e.g., a TNFα inhibitor, to a user (also referred to herein as a patient). In one embodiment, the dose delivered by the automatic injection device of the invention comprises a human TNFα antibody, or antigen-binding portion thereof. A particularly preferred medication is a TNFα inhibitor.

The term "human TNFα" (abbreviated herein as hTNFα, or simply hTNF), as used herein, is intended to refer to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) *Nature* 312:724-729; Davis, J. M., et al. (1987) *Biochemistry* 26:1322-1326; and Jones, E. Y., et al. (1989) *Nature* 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.). TNFα is also referred to as TNF.

The term "TNFα inhibitor" refers to an agent that interferes with TNFα activity. The term also includes each of the anti-TNFα human antibodies (used interchangeably herein with TNFα antibodies) and antibody portions described herein as well as those described in U.S. Pat. Nos. 6,090,382; 6,258,562; 6,509,015, and in U.S. patent application Ser. Nos. 09/801,185 and 10/302,356. In one embodiment, the TNFα inhibitor used in the invention is an anti-TNFα antibody, or a fragment thereof, including infliximab (the REMICADE™ antibody, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (HUMIRA® Abbott Laboratories, a human anti-TNF mAb, described in U.S. Pat. No. 6,090,382 as D2E7). Additional TNF antibodies that may be used in the invention are described in U.S. Pat. Nos. 6,593,458; 6,498,237; 6,451,983; and 6,448,380, each of which is incorporated by reference herein. In another embodiment, the TNFα inhibitor is a TNF fusion protein, e.g., etanercept (the ENBREL™ protein, Amgen; described in WO 91/03553 and WO 09/406476, incorporated by reference herein). In another embodiment, the TNFα inhibitor is a recombinant TNF binding protein (r-TBP-I) (Serono).

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibodies of the invention are described in further detail in U.S. Pat. Nos. 6,090,382; 6,258,562; and 6,509,015, each of which is incorporated herein by reference in its entirety.

The term "antigen-binding portion" of an antibody (or simply "antibody portion"), as used herein, refers to one or more fragments of an antibody that retain the ability to specifically bind to an antigen (e.g., hTNFα). It has been shown that fragments of a full-length antibody can perform the antigen-binding function of an antibody. Examples of binding fragments encompassed within the term "antigen-binding portion" of an antibody include (i) a Fab fragment, a monovalent fragment consisting of the VL, VH, CL and CH1 domains; (ii) a F(ab')₂ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 341:544-546), which consists of a VH or VL domain; (vi) an isolated complementarity determining region (CDR); and (vii) a dual variable domain (DVD) antibody. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. USA* 90:6444-6448; Poljak et al. (1994) *Structure* 2:1121-1123). The antibody portions of the invention are described in further detail in U.S. Pat. Nos. 6,090,382, 6,258,562, 6,509,015, each of which is incorporated herein by reference in its entirety.

In one embodiment, the TNF inhibitor used in the methods and compositions of the invention includes a TNF fusion protein, e.g., etanercept (the ENBREL™ protein, Amgen; described in WO 91/03553 and WO 09/406476, incorporated by reference herein), as well as a recombinant TNF binding protein (r-TBP-I) (Serono).

In one embodiment, the TNF inhibitor used in the methods and compositions of the invention includes isolated human antibodies, or antigen-binding portions thereof, that bind to human TNFα with high affinity and a low off rate, and have a high neutralizing capacity. Preferably, the human antibodies of the invention are recombinant, neutralizing human anti-hTNFα antibodies. The most preferred recombinant, neutralizing antibody of the invention is referred to herein as D2E7, also referred to as HUMIRA® or adalimumab (the amino acid sequence of the D2E7 VL region is shown in SEQ ID NO: 1 of U.S. Pat. No. 6,090,382 the amino acid sequence of the D2E7 VH region is shown in SEQ ID NO: 2 of U.S. Pat. No. 6,090,382). The properties of D2E7 (HUMIRA®) have been described in Salfeld et al., U.S. Pat. Nos. 6,090,382, 6,258,562, and 6,509,015, which are each incorporated by reference herein. Other examples of TNFα inhibitors include chimeric and humanized murine anti-hTNFα antibodies that have undergone clinical testing for treatment of rheumatoid arthritis (see e.g., Elliott et al. (1994) *Lancet* 344:1125-1127; Elliot et al. (1994) *Lancet* 344:1105-1110; Rankin et al. (1995) *Br. J. Rheumatol.* 34:334-342). In another embodiment, the TNFα inhibitor used in the invention is an anti-TNFα antibody, or a fragment thereof, comprising infliximab (the REMICADE™ antibody, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), and CNTO 148 (golimumab; Medarex and Centocor, see WO 02/12502).

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) *Nucl. Acids Res.* 20:6287) or antibodies prepared, expressed, created or isolated by any other means that involves splicing of human immunoglobulin gene sequences to other DNA sequences. Such recombinant human antibodies have variable and constant regions derived from human germ line immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germ line VH and VL sequences, may not naturally exist within the human antibody germ line repertoire in vivo.

Such chimeric, humanized, human, and dual specific antibodies can be produced by recombinant DNA techniques known in the art, for example using methods described in PCT International Application No. PCT/US86/02269; European Patent Application No. 184,187; European Patent Application No. 171,496; European Patent Application No. 173, 494; PCT International Publication No. WO 86/01533; U.S. Pat. No. 4,816,567; European Patent Application No. 125, 023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314: 446-449; Shaw et al. (1988) *J. Natl. Cancer Inst.* 80:1553-1559; Morrison (1985) *Science* 229:1202-1207; Oi et al. (1986) *BioTechniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141: 4053-4060, Queen et al., *Proc. Natl. Acad. Sci. USA* 86:10029-10033 (1989), U.S. Pat. No. 5,530,101, 5,585,089, 5,693,761, 5,693,762, Selick et al., WO 90/07861, and Winter, U.S. Pat. No. 5,225,539.

An "isolated antibody", as used herein, is intended to refer to an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may, however, have cross-reactivity to other antigens, such as TNFα molecules from other species. Moreover, an isolated antibody may be substantially free of other cellular material and/or chemicals.

A "neutralizing antibody", as used herein (or an "antibody that neutralized hTNFα activity"), is intended to refer to an antibody whose binding to hTNFα results in inhibition of the biological activity of hTNFα. This inhibition of the biological activity of hTNFα can be assessed by measuring one or more indicators of hTNFα biological activity, such as hTNFα-induced cytotoxicity (either in vitro or in vivo), hTNFα-induced cellular activation and hTNFα binding to hTNFα receptors. These indicators of hTNFα biological activity can be assessed by one or more of several standard in vitro or in vivo assays known in the art (see U.S. Pat. No. 6,090,382). Preferably, the ability of an antibody to neutralize hTNFα activity is assessed by inhibition of hTNFα-induced cytotoxicity of L929 cells. As an additional or alternative parameter of hTNFα activity, the ability of an antibody to inhibit hTNFα-induced expression of ELAM-1 on HUVEC, as a measure of hTNFα-induced cellular activation, can be assessed.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 of U.S. Pat. No. 6,258,562 and Jönsson et al. (1993) *Ann. Biol. Clin.* 51:19; Jönsson et al. (1991) *Biotechniques* 11:620-627; Johnsson et al. (1995) *J. Mol. Recognit.* 8:125; and Johnnson et al. (1991) *Anal. Biochem.* 198:268.

The term "$K_{off}$", as used herein, is intended to refer to the off rate constant for dissociation of an antibody from the antibody/antigen complex. The term "$K_d$", as used herein, is intended to refer to the dissociation constant of a particular antibody-antigen interaction.

The term "$IC_{50}$" as used herein, is intended to refer to the concentration of the inhibitor required to inhibit the biological endpoint of interest, e.g., neutralize cytotoxicity activity.

The term "dose," as used herein, refers to an amount of a substance, such as a TNFα inhibitor, which is administered to a user preferably using the automatic injection device of the invention. In one embodiment, the dose comprises an effective amount, for example, including 20 mg, 40 mg, 80 mg, and 160 mg, of the TNFα inhibitor adalimumab.

The term "dosing", as used herein, refers to the administration of a substance (e.g., an anti-TNFα antibody) to achieve a therapeutic objective (e.g., treatment of rheumatoid arthritis).

A "dosing regimen" describes a treatment schedule for a substance, such as a TNFα inhibitor, e.g., a treatment schedule over a prolonged period of time and/or throughout the course of treatment, e.g. administering a first dose of a TNFα inhibitor at week 0 followed by a second dose of a TNFα inhibitor on a biweekly dosing regimen.

The terms "biweekly dosing regimen", "biweekly dosing", and "biweekly administration", as used herein, refer to the time course of administering a substance (e.g., an anti-TNFα antibody) to a patient to achieve a therapeutic objective, e.g., throughout the course of treatment. The biweekly dosing regimen is not intended to include a weekly dosing regimen. Preferably, the substance is administered every 9-19 days, more preferably, every 11-17 days, even more preferably, every 13-15 days, and most preferably, every 14 days. In one embodiment, the biweekly dosing regimen is initiated in a patient at week 0 of treatment. In another embodiment, a maintenance dose is administered on a biweekly dosing regimen.

In one embodiment, both the loading and maintenance doses are administered according to a biweekly dosing regimen. In one embodiment, biweekly dosing includes a dosing regimen wherein doses of a TNFα inhibitor are administered to a patient every other week beginning at week 0. In one embodiment, biweekly dosing includes a dosing regimen where doses of a TNFα inhibitor are administered to a patient every other week consecutively for a given time period, e.g., 4 weeks, 8 weeks, 16, weeks, 24 weeks, 26 weeks, 32 weeks, 36 weeks, 42 weeks, 48 weeks, 52 weeks, 56 weeks, etc. Biweekly dosing methods are also described in US 20030235585, incorporated by reference herein.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent.

The term "concomitant" as in the phrase "concomitant therapeutic treatment" includes administering an agent in the presence of a second agent. A concomitant therapeutic treatment method includes methods in which the first, second, third, or additional substances are co-administered. A concomitant therapeutic treatment method also includes methods in which the first or additional agents are administered in the presence of a second or additional substances, wherein the second or additional agents, for example, may have been previously administered. A concomitant therapeutic treatment method may be executed step-wise by different patients. For example, one subject may administer to a user a first agent and a second subject may to administered to the user a second substance, and the administering steps may be executed at the same time, or nearly the same time, or at distant times, so long as the first substance (and additional substances) are after administration in the presence of the second substance (and additional substances). The actor and the user may be the same entity (e.g., human).

The term "combination therapy", as used herein, refers to the administration of two or more therapeutic substances, e.g., an anti-TNFα antibody and another drug. The other drug(s) may be administered concomitant with, prior to, or following the administration of an anti-TNFα antibody.

The term "treatment," as used within the context of the present invention, is meant to include therapeutic treatment, as well as prophylactic or suppressive measures, for the treatment of a disorder, such as a disorder in which TNFα is detrimental, e.g., rheumatoid arthritis.

In one embodiment, the invention provides improved uses and compositions for treating a disorder in which TNFα is detrimental, e.g., rheumatoid arthritis with a TNFα inhibitor, e.g., a human TNFα antibody, or an antigen-binding portion thereof, through an automatic injection device.

The substance that is delivered via the automatic injection device of the invention may be a TNFα inhibitor . A TNFα inhibitor includes any agent (or substance) that interferes with TNFα activity. In a preferred embodiment, the TNFα inhibitor can neutralize TNFα activity, particularly detrimental TNFα activity which is associated with disorders in which TNFα activity is detrimental, including, but not limited to, rheumatoid arthritis, juvenile rheumatoid arthritis, ankylosing spondylitis, Crohn's disease, psoriasis, and psoriatic arthritis.

In one embodiment, the TNFα inhibitor used in the invention is an anti-TNFα antibody (also referred to herein as a TNFα antibody), or an antigen-binding fragment thereof, including chimeric, humanized, and human antibodies. Examples of TNFα antibodies that may be used in the invention include, but are not limited to, infliximab (the REMICADE™ antibody, Johnson and Johnson; described in U.S. Pat. No. 5,656,272, incorporated by reference herein), CDP571(a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (HUMIRA® Abbott Laboratories, a human anti-TNF mAb, described in U.S. Pat. No. 6,090,382 as D2E7). Additional TNF antibodies that may be used in the invention are described in U.S. Pat. Nos. 6,593,458; 6,498,237; 6,451,983; and 6,448,380, each of which is incorporated by reference herein.

Other examples of TNFα inhibitors which may be used in the methods and compositions of the invention include etanercept (the ENBREL™ protein, described in WO 91/03553 and WO 09/406476), soluble TNF receptor Type I, a pegylated soluble TNF receptor Type I (PEGs TNF-R1), p55TNFR1gG (Lenercept), and recombinant TNF binding protein (r-TBP-I) (Serono). Examples of TNFα inhibitors include but are not limited to infliximab (the REMICADE™ antibody), CDP 571, CDP 870, anti-TNF dAb, golimumab, adalimumab, etanercept (the ENBREL™ protein), p55TNFR1gG (Lenercept) and r-TBP-1. A particularly preferred TNFα inhibitor is adalimumab (HUMIRA®).

In one embodiment, the term "TNFα inhibitor" excludes infliximab. In one embodiment, the term "TNFα inhibitor" excludes adalimumab. In another embodiment, the term "TNFα inhibitor" excludes adalimumab and infliximab.

In one embodiment, the term "TNFα inhibitor" excludes etanercept, and, optionally, adalimumab, infliximab, and adalimumab and infliximab.

In one embodiment, the term "TNFα antibody" excludes infliximab. In one embodiment, the term "TNFα antibody" excludes adalimumab. In another embodiment, the term "TNFα antibody" excludes adalimumab and infliximab.

In one embodiment, the invention features uses and composition for treating or determining the efficacy of a TNFα inhibitor for the treatment of rheumatoid arthritis, wherein the TNFα antibody is an isolated human antibody, or antigen-binding portion thereof, that binds to human TNFα with high affinity and a low off rate, and also has a high neutralizing capacity. Preferably, the human antibodies used in the invention are recombinant, neutralizing human anti-hTNFα antibodies. The most preferred recombinant, neutralizing antibody of the invention is referred to herein as D2E7, also referred to as HUMIRA® or adalimumab (the amino acid sequence of the D2E7 VL region is shown in SEQ ID NO: 1; the amino acid sequence of the D2E7 VH region is shown in SEQ ID NO: 2). The properties of D2E7 (adalimumab/HUMIRA®) have been described in Salfeld et al., U.S. Pat. Nos. 6,090,382, 6,258,562, and 6,509,015, which are each incorporated by reference herein. The methods of the invention may also be performed using chimeric and humanized murine anti-hTNFα antibodies which have undergone clinical testing for treatment of rheumatoid arthritis (see e.g., Elliott, M. J., et al. (1994) *Lancet* 344:1125-1127; Elliot, M. J., et al. (1994) *Lancet* 344:1105-1110; Rankin, E. C., et al. (1995) *Br. J. Rheumatol.* 34:334-342).

In one embodiment, the method of the invention includes determining the efficacy of adalimumab antibodies and antibody portions, adalimumab-related antibodies and antibody portions, or other human antibodies and antibody portions with equivalent properties to adalimumab, such as high affinity binding to hTNFα with low dissociation kinetics and high neutralizing capacity, for the treatment of rheumatoid arthritis. In one embodiment, the invention provides treatment with an isolated human antibody, or an antigen-binding portion thereof, that dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an $IC_{50}$ of $1 \times 10^{-7}$ M or less. More preferably, the isolated human antibody, or antigen-binding portion thereof, dissociates from human TNFα with a $K_{off}$ of $5 \times 10^{-4}$ s$^{-1}$ or less, or even more preferably, with a $K_{off}$ of $1 \times 10^{-4}$ s$^{-1}$ or less. More preferably, the isolated human antibody, or antigen-binding portion thereof, neutralizes human TNFα cytotoxicity in a standard in vitro L929 assay with an $IC_{50}$ of $1 \times 10^{-8}$ M or less, even more preferably with an $IC_{50}$ of $1 \times 10^{-9}$ M or less and still more preferably with an $IC_{50}$ of $1 \times 10^{-10}$ M or less. In a preferred embodiment, the antibody is an isolated human recombinant antibody, or an antigen-binding portion thereof.

It is well known in the art that antibody heavy and light chain CDR3 domains play an important role in the binding specificity/affinity of an antibody for an antigen. Accordingly, in another aspect, the invention pertains to treating Crohn's disease by administering human antibodies that have slow dissociation kinetics for association with hTNFα and that have light and heavy chain CDR3 domains that structurally are identical to or related to those of D2E7. Position 9 of the D2E7 VL CDR3 can be occupied by Ala or Thr without substantially affecting the $K_{off}$. Accordingly, a consensus motif for the D2E7 VL CDR3 comprises the amino acid sequence: Q-R-Y-N-R-A-P-Y-(T/A) (SEQ ID NO: 3). Additionally, position 12 of the D2E7 VH CDR3 can be occupied by Tyr or Asn, without substantially affecting the $K_{off}$. Accordingly, a consensus motif for the D2E7 VH CDR3 comprises the amino acid sequence: V-S-Y-L-S-T-A-S-S-L-D-(Y/N) (SEQ ID NO: 4). Moreover, as demonstrated in Example 2 of U.S. Pat. No. 6,090,382, the CDR3 domain of the D2E7 heavy and light chains is amenable to substitution with a single alanine residue (at position 1, 4, 5, 7 or 8 within the VL CDR3 or at position 2, 3, 4, 5, 6, 8, 9, 10 or 11 within the VH CDR3) without substantially affecting the $K_{off}$. Still further, the skilled artisan will appreciate that, given the amenability of the D2E7 VL and VH CDR3 domains to substitutions by alanine, substitution of other amino acids within the CDR3 domains may be possible while still retaining the low off rate constant of the antibody, in particular substitutions with conservative amino acids. Preferably, no more than one to five conservative amino acid substitutions are made within the D2E7 VL and/or VH CDR3 domains. More preferably, no more than one to three conservative amino acid substitutions are made within the D2E7 VL and/or VH CDR3 domains. Additionally, conservative amino acid substitutions should not be made at amino acid positions critical for binding to hTNFα. Positions 2 and 5 of the D2E7 VL CDR3 and positions 1 and 7 of the D2E7 VH CDR3 appear to be critical for interaction with hTNFα and thus, conservative amino acid substitutions preferably are not made at these positions (although an alanine substitution at position 5 of the D2E7 VL CDR3 is acceptable, as described above) (see U.S. Pat. No. 6,090,382).

Accordingly, in another embodiment, the antibody or antigen-binding portion thereof preferably contains the following characteristics:

a) dissociates from human TNFα with a $K_{off}$ rate constant of $1 \times 10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

More preferably, the antibody, or antigen-binding portion thereof, dissociates from human TNFα with a $K_{off}$ of $5 \times 10^{-4}$ s$^{-1}$ or less. Even more preferably, the antibody, or antigen-binding portion thereof, dissociates from human TNFα with a $K_{off}$ of $1 \times 10^{-4}$ s$^{-1}$ or less.

In yet another embodiment, the antibody or antigen-binding portion thereof preferably contains a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and with a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. Preferably, the LCVR further has a CDR2 domain comprising the amino acid sequence of SEQ ID NO: 5 (i.e., the D2E7 VL CDR2) and the HCVR further has a CDR2 domain comprising the amino acid sequence of SEQ ID NO: 6 (i.e., the D2E7 VH CDR2). Even more preferably, the LCVR further has CDR1 domain comprising the amino acid sequence of SEQ ID NO: 7 (i.e., the D2E7 VL CDR1) and the HCVR has a CDR1 domain comprising the amino acid sequence of SEQ ID NO: 8 (i.e., the D2E7 VH CDR1). The framework regions for VL preferably are from the $V_\kappa I$ human germ line family, more preferably from the A20 human germ line Vk gene and most preferably from the D2E7 VL framework sequences shown in FIGS. 1A and 1B of U.S. Pat. No. 6,090,382. The framework regions for VH preferably are from the $V_H 3$ human germ line family, more preferably from the DP-31 human germ line VH gene and most preferably from the D2E7 VH framework sequences shown in FIGS. 2A and 2B of U.S. Pat. No. 6,090,382.

Accordingly, in another embodiment, the antibody or antigen-binding portion thereof preferably contains a light chain variable region (LCVR) comprising the amino acid sequence of SEQ ID NO: 1 (i.e., the D2E7 VL) and a heavy chain variable region (HCVR) comprising the amino acid sequence of SEQ ID NO: 2 (i.e., the D2E7 VH). In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In still other embodiments, the invention includes uses of an isolated human antibody, or antigen-binding portion thereof, containing D2E7-related VL and VH CDR3 domains. For example, antibodies, or antigen-binding portions thereof, with a light chain variable region (LCVR) having a CDR3 domain comprising an amino acid sequence selected from the group consisting of SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26 or with a heavy chain variable region (HCVR) having a CDR3 domain comprising an amino acid sequence selected from the group consisting of SEQ ID NO: 4, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 and SEQ ID NO: 35.

The TNFα antibody used in the methods and compositions of the invention may be modified for improved treatment of rheumatoid arthritis. In some embodiments, the TNFα antibody or antigen binding fragments thereof, is chemically modified to provide a desired effect. For example, pegylation of antibodies and antibody fragments of the invention may be carried out by any of the pegylation reactions known in the art, as described, for example, in the following references: *Focus on Growth Factors* 3:4-10 (1992); EP 0 154 316; and EP 0 401 384 (each of which is incorporated by reference herein in its entirety). Preferably, the pegylation is carried out via an acylation reaction or an alkylation reaction with a reactive polyethylene glycol molecule (or an analogous reactive water-soluble polymer). A preferred water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (CI—ClO) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Pegylated antibodies and antibody fragments may generally be used to treat rheumatoid arthritis by administration of the TNFα antibodies and antibody fragments described herein. Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

In yet another embodiment of the invention, TNFα antibodies or fragments thereof can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see e.g., Canfield, S. M. and S. L. Morrison (1991) *J. Exp. Med.* 173:1483-1491; and Lund, J. et al. (1991) *J. of Immunol.* 147:2657-2662). Reduction in FcR binding ability of the antibody may also reduce other effector functions that rely on FcR interactions, such as opsonization and phagocytosis and antigen-dependent cellular cytotoxicity.

An antibody or antibody portion used in the compositions and methods of the invention can be derivatized or linked to another functional molecule (e.g., another peptide or protein). Accordingly, the antibodies and antibody portions of the invention are intended to include derivatized and otherwise modified forms of the human anti-hTNFα antibodies described herein, including immunoadhesion molecules. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

An antibody, or antibody portion, used in the methods and compositions of the invention, can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss et al.

To express adalimumab (D2E7) or an adalimumab (D2E7)-related antibody, DNA fragments encoding the light and heavy chain variable regions are first obtained. These DNAs can be obtained by amplification and modification of germline light and heavy chain variable sequences using the polymerase chain reaction (PCR). Germline DNA sequences for human heavy and light chain variable region genes are known in the art (see e.g., the "Vbase" human germline sequence database; see also Kabat, E. A., et al. (1991) *Sequences of Proteins of Immunological Interest, Fifth Edition*, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_{78}$ Segments Reveals a Strong Bias in their Usage" *Eur. J. Immunol.* 24:827-836; the contents of each of which are expressly incorporated herein by reference). To obtain a DNA fragment encoding the heavy chain variable region of D2E7, or a D2E7-related antibody, a member of the $V_H3$ family of human germline VH genes is amplified by standard PCR. Most preferably, the DP-31 VH germline sequence is amplified. To obtain a DNA fragment encoding the light chain variable region of D2E7, or a D2E7-related antibody, a member of the $V_\kappa I$ family of human germline VL genes is amplified by standard PCR. Most preferably, the A20 VL germline sequence is amplified. PCR primers suitable for use in amplifying the DP-31 germline VH and A20 germline VL sequences can be designed based on the nucleotide sequences disclosed in the references cited supra, using standard methods.

Once the germline VH and VL fragments are obtained, these sequences can be mutated to encode the D2E7 or D2E7-related amino acid sequences disclosed herein. The amino acid sequences encoded by the germline VH and VL DNA sequences are first compared to the D2E7 or D2E7-related VH and VL amino acid sequences to identify amino acid residues in the D2E7 or D2E7-related sequence that differ from germline. Then, the appropriate nucleotides of the germline DNA sequences are mutated such that the mutated germline sequence encodes the D2E7 or D2E7-related amino acid sequence, using the genetic code to determine which nucleotide changes should be made. Mutagenesis of the germline sequences is carried out by standard methods, such as PCR-mediated mutagenesis (in which the mutated nucleotides are incorporated into the PCR primers such that the PCR product contains the mutations) or site-directed mutagenesis.

Moreover, it should be noted that if the "germline" sequences obtained by PCR amplification encode amino acid differences in the framework regions from the true germline configuration (i.e., differences in the amplified sequence as compared to the true germline sequence, for example as a result of somatic mutation), it may be desirable to change these amino acid differences back to the true germline sequences (i.e., "backmutation" of framework residues to the germline configuration).

Once DNA fragments encoding D2E7 or D2E7-related VH and VL segments are obtained (by amplification and mutagenesis of germline VH and VL genes, as described above), these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4-Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., *Nature* (1990) 348:552-554).

To express the antibodies, or antibody portions used in the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the D2E7 or D2E7-related light or heavy chain sequences, the expression vector may already carry antibody constant region sequences. For example, one approach to converting the D2E7 or D2E7-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors used in the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr− CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It is understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hTNFα. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hTNFα by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

In view of the foregoing, nucleic acid, vector and host cell compositions that can be used for recombinant expression of the antibodies and antibody portions used in the invention include nucleic acids, and vectors comprising said nucleic acids, comprising the human TNFα antibody adalimumab (D2E7). The nucleotide sequence encoding the D2E7 light chain variable region is shown in SEQ ID NO: 36. The CDR1 domain of the LCVR encompasses nucleotides 70-102, the CDR2 domain encompasses nucleotides 148-168 and the CDR3 domain encompasses nucleotides 265-291. The nucleotide sequence encoding the D2E7 heavy chain variable region is shown in SEQ ID NO: 37. The CDR1 domain of the HCVR encompasses nucleotides 91-105, the CDR2 domain encompasses nucleotides 148-198 and the CDR3 domain encompasses nucleotides 295-330. It will be appreciated by the skilled artisan that nucleotide sequences encoding D2E7-related antibodies, or portions thereof (e.g., a CDR domain, such as a CDR3 domain), can be derived from the nucleotide sequences encoding the D2E7 LCVR and HCVR using the genetic code and standard molecular biology techniques.

Recombinant human antibodies of the invention in addition to D2E7 or an antigen binding portion thereof, or D2E7-related antibodies disclosed herein can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia *Recombinant Phage Antibody System*, catalog no. 27-9400-01; and the Stratagene the SUR-FZAP™ phage display vector phage display kit, catalog no. 240612), examples of methods and reagents particularly amenable for use in generating and screening antibody display libraries can be found in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-65; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226: 889-896; Clackson et al. (1991) *Nature* 352:624-628; Gram et al. (1992) PNAS 89:3576-3580; Garrard et al. (1991) *Bio/Technology* 9:1373-1377; Hoogenboom et al. (1991) *Nuc Acid Res* 19:4133-4137; and Barbas et al. (1991) *PNAS* 88:7978-7982.

In a preferred embodiment, to isolate human antibodies with high affinity and a low off rate constant for hTNFα, a murine anti-hTNFα antibody having high affinity and a low off rate constant for hTNFα (e.g., MAK 195, the hybridoma for which has deposit number ECACC 87 050801) is first used to select human heavy and light chain sequences having similar binding activity toward hTNFα, using the epitope imprinting methods described in Hoogenboom et al., PCT Publication No. WO 93/06213. The antibody libraries used in this method are preferably scFv libraries prepared and screened as described in McCafferty et al., PCT Publication No. WO 92/01047, McCafferty et al., *Nature* (1990) 348:552-554; and Griffiths et al., (1993) *EMBO J* 12:725-734. The scFv antibody libraries preferably are screened using recombinant human TNFα as the antigen.

Once initial human VL and VH segments are selected, "mix and match" experiments, in which different pairs of the initially selected VL and VH segments are screened for hTNFα binding, are performed to select preferred VL/VH pair combinations. Additionally, to further improve the affinity and/or lower the off rate constant for hTNFα binding, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be rescreened for binding to hTNFα and sequences that exhibit high affinity and a low off rate for hTNFα binding can be selected.

Following screening and isolation of an hTNFα antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention (e.g., linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in above.

Methods of isolating human neutralizing antibodies with high affinity and a low off rate constant for hTNFα are described in U.S. Pat. Nos. 6,090,382, 6,258,562, and 6,509,015, each of which is incorporated by reference herein.

IV. Substances for Use in the Automatic Injection Device

The methods and compositions of the invention can be used with automatic injection devices that administer essentially any substance or medication that is suitable for administration by injection. Typically, the substance or medication will be in a fluid, e.g., liquid form, although medications in other forms such as gels or semi-solids, slurries, particulate solutions, etc. also may suitable for use if the automatic injection device is designed to permit the administration of such forms of the medication.

Preferred medications are biological agents, such as antibodies, cytokines, vaccines, fusion proteins and growth factors. Methods of making antibodies are described above.

Non-limiting examples of other biological agents that can be used as the medication in the automatic injection device include but are not limited to antibodies to or antagonists of human cytokines or growth factors, for example, TNF, LT, IL-1, IL-2, IL-3, IL-4, IL-5, IL-6, IL-7, IL-8, IL-15, IL-16, IL-18, IL-21, IL-23, interferons, EMAP-II, GM-CSF, FGF, and PDGF; antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L); TNFα converting enzyme (TACE) inhibitors; IL-1 inhibitors (Interleukin-1-converting enzyme inhibitors, IL-1RA etc.); Interleukin 11; IL-18 antagonists including IL-18 antibodies or soluble IL-18 receptors, or IL-18 binding proteins; non-depleting anti-CD4 inhibitors; antagonists of the co-stimulatory pathway CD80 (B7.1) or CD86 (B7.2) including antibodies, soluble receptors or antagonistic ligands; agents which interfere with signalling by proinflammatory cytokines such as TNFα or IL-1 (e.g. I RAK, NIK, IKK, p38 or MAP kinase inhibitors); IL-1β converting enzyme (ICE) inhibitors; T-cell signalling inhibitors such as kinase inhibitors; metalloproteinase inhibitors; angiotensin converting enzyme inhibitors; soluble cytokine receptors and derivatives thereof (e.g. soluble p55 or p75 TNF receptors and the derivatives p75TNFRIgG (the ENBREL™ protein and p55TNFRIgG (Lenercept)), sIL-1RI, sIL-1RII, sIL-6R); antiinflammatory cytokines (e.g. IL-4, IL-10, IL-11, IL-13 and TGF-beta); Rituximab; IL-1 TRAP; MRA; CTLA4-Ig; IL-18 BP; anti-IL-18; anti-IL15; IDEC-CE9.1/SB 210396 (non-depleting primatized anti-CD4 antibody; IDEC/SmithKline; see e.g., *Arthritis & Rheumatism* (1995) Vol. 38, S185); DAB 486-IL-2 and/or DAB 389-IL-2 (IL-2 fusion proteins; Seragen; see e.g., *Arthritis & Rheumatism* (1993) Vol. 36, 1223); Anti-Tac (humanized anti-IL-2Ra; Protein Design Labs/Roche); IL-4 (anti-inflammatory cytokine; DNAX/Schering); IL-10 (SCH 52000; recombinant IL-10, anti-inflammatory cytokine; DNAX/Schering); IL-10 and/or IL-4 agonists (e.g., agonist antibodies); IL-1RA (IL-1 receptor antagonist; Synergen/Amgen); anakinra (the KINERET™ interleukin-1 receptor antagonist/Amgen); TNF-bp/s-TNF (soluble TNF binding protein; see e.g., *Arthritis & Rheumatism* (1996) Vol. 39, No. 9 (supplement), S284; *Amer. J. Physiol.—Heart and Circulatory Physiology* (1995) Vol. 268, pp. 37-42); R973401 (phosphodiesterase Type IV inhibitor; see e.g., *Arthritis & Rheumatism* (1996) Vol. 39, No. 9 (supplement), S282); MK-966 (COX-2 Inhibitor; see e.g., Arthritis & Rheumatism (1996) Vol. 39, No. 9 (supplement), S81); Iloprost (see e.g., *Arthritis & Rheumatism* (1996) Vol. 39, No. 9 (supplement), S82); zap-70and/or lck inhibitor (inhibitor of the tyrosine kinase zap-70 or lck); VEGF inhibitor and/or VEGF-R inhibitor (inhibitors of vascular endothelial cell growth factor or vascular endothelial cell growth factor receptor; inhibitors of angiogenesis); TNF-convertase inhibitors; anti-IL-12 antibodies; anti-IL-18 antibodies; interleukin-11 (see e.g., *Arthritis & Rheumatism* (1996) Vol. 39, No. 9 (supplement), S296); interleukin-13 (see e.g., *Arthritis & Rheumatism* (1996) Vol. 39, No. 9 (supplement), S308); interleukin -17 inhibitors (see e.g., *Arthritis & Rheumatism* (1996) Vol. 39, No. 9 (supplement), S120); anti-thymocyte globulin; anti-CD4 antibodies; CD5-toxins; ICAM-1 antisense phosphorothioate oligo-deoxynucleotides (ISIS 2302; Isis Pharmaceuticals, Inc.); soluble complement receptor 1 (TP10; T Cell Sciences, Inc.); and anti-IL2R antibodies.

Pharmaceutical compositions may be loaded into the automatic injection device of the invention for delivery to a user. In one embodiment, antibodies, antibody-portions, as well as other TNFα inhibitors, can be incorporated into pharmaceutical compositions suitable for administration to a user using the device of the invention. Typically, the pharmaceutical composition comprises an antibody, antibody portion, or other TNFα inhibitor, and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody, antibody portion, or other TNFα inhibitor.

The compositions for use in the methods and compositions of the invention may be in a variety of forms in accordance with administration via the device of the invention, including, for example, liquid solutions (e.g., injectable and infusible solutions), dispersions or suspensions. In a preferred embodiment, the antibody or other TNFα inhibitor is administered by subcutaneous injection using the device of the invention. In one embodiment, the user administers the TNFα inhibitor, including, but not limited to, TNFα antibody, or antigen-binding portion thereof, to himself/herself using the device of the invention Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody, antibody portion, or other TNFα inhibitor) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required-other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In one embodiment, the invention includes an automatic injection device, e.g., autoinjector pen, comprising an effective TNFα inhibitor and a pharmaceutically acceptable carrier. Thus, the invention provides a prefilled automatic injection device comprising a TNFα inhibitor.

In one embodiment, the antibody or antibody portion for use in the methods of the invention is incorporated into a pharmaceutical formulation as described in PCT/IB03/04502 and U.S. Appln. No. 20040033228, incorporated by reference herein. This formulation includes a concentration 50 mg/ml of the antibody D2E7 (adalimumab), wherein one autoinjector pen comprises 40 mg of antibody for subcutaneous injection. In one embodiment, the automatic injection device of the invention (or more specifically the syringe of the device) comprises a formulation of adalimumab having the following formula: adalimumab, sodium chloride, monobasic sodium phosphate dihydrate, dibasic sodium phosphate dihydrate, sodium citrate, citric acid monohydrate, mannitol, polysorbate 80 and water, e.g., water for injection. In another embodiment, the automatic injection device comprises a volume of adalimumab including 40 mg adalimumab, 4.93 mg sodium chloride, 0.69 mg monobasic sodium phosphate dihydrate, 1.22 mg dibasic sodium phosphate dihydrate, 0.24 mg sodium citrate, 1.04 mg citric acid monohydrate, 9.6 mg mannitol, 0.8 mg polysorbate 80 and water, e.g., water for injection. In one embodiment, sodium hydroxide is added as necessary to adjust pH.

The dose amount of TNFα inhibitor in the automatic injection device may vary according to the disorder for which the TNFα inhibitor is being used to treat. In one embodiment, the invention includes an automatic injection device comprising a dose of adalimumab of about 20 mg of adalimumab; 40 mg of adalimumab; 80 mg of adalimumab; and 160 mg of adalimumab. It should be noted that for all ranges described herein, including the dose ranges, all numbers intermediary to the recited values are included in the invention, e.g., 36 mg of adalimumab, 48 mg of adalimumab, etc. In addition ranges recited using said numbers are also included, e.g., 40 to 80 mg of adalimumab. The numbers recited herein are not intended to limit the scope of the invention.

The TNFα antibodies and inhibitors used in the invention may also be administered in the form of protein crystal formulations that include a combination of protein crystals encapsulated within a polymeric carrier to form coated particles. The coated particles of the protein crystal formulation may have a spherical morphology and be microspheres of up to 500 micro meters in diameter or they may have some other morphology and be microparticulates. The enhanced concentration of protein crystals allows the antibody of the invention to be delivered subcutaneously. In one embodiment, the TNFα antibodies of the invention are delivered via a protein delivery system, wherein one or more of a protein crystal formulation or composition, is administered to a user with a TNFα-related disorder. Compositions and methods of preparing stabilized formulations of whole antibody crystals or antibody fragment crystals are also described in WO 02/072636, which is incorporated by reference herein. In one embodiment, a formulation comprising the crystallized antibody fragments described in PCT/IB03/04502 and U.S. Appln. No. 20040033228, incorporated by reference herein, is used to treat rheumatoid arthritis using the methods of the invention.

Supplementary active compounds can also be incorporated into the compositions. In certain embodiments, an antibody or antibody portion for use in the methods of the invention is coformulated with and/or coadministered with one or more additional therapeutic agents, including a rheumatoid arthritis inhibitor or antagonist. For example, an anti-hTNFα antibody or antibody portion may be coformulated and/or coadministered with one or more additional antibodies that bind other targets associated with TNFα related disorders (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751) or any combination thereof. Furthermore, one or more antibodies of the invention may be used in combination with two or more of the foregoing therapeutic agents. Such combination therapies may advantageously utilize lower dosages of the administered therapeutic agents, thus avoiding possible side effects, complications or low level of response by the patient associated with the various monotherapies. Additional agents that may be used in combination with a TNFα antibody or antibody portion are described in U.S. application Ser. No. 11/800,531, which is incorporated in its entirety herein.

The automatic injection device, e.g., autoinjector pen, of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody, antibody portion, or other TNFα inhibitor may vary according to factors such as the disease state, age, sex, and weight of the individual, and the ability of the antibody, antibody portion, other TNFα inhibitor to elicit a desired response in the individual. A therapeutically effective amount is also one in which any toxic or detrimental effects of the antibody, antibody portion, or other TNFα inhibitor are outweighed by the therapeutically beneficial effects. A "prophylactically effective amount" refers to an amount effective, at dosages and for periods of time necessary, to achieve the desired prophylactic result. Typically, since a prophylactic dose is used in patients prior to or at an earlier stage of disease, the prophylactically effective amount will be less than the therapeutically effective amount.

V. Articles of Manufacture of the Invention

The invention also provides an article of manufacture or kit comprising the automatic injection device of the invention. In one embodiment of the invention, the kit comprises an automatic injector device, e.g., an autoinjector pen such as the HUMIRA® pen, comprising a liquid drug, e.g., a TNFα inhibitor, such as an antibody, and instructions for administration of the liquid drug. In one embodiment, the kit comprises instructions for delivering a TNFα inhibitor for treatment of a disorder in which TNFα is detrimental, e.g., rheumatoid arthritis, using the automatic injection device. The instructions may describe how, e.g., subcutaneously, and when, e.g., at week 0, week 2, week 4, etc., the dose of TNFα inhibitor shall be administered to a patient for treatment.

An article of manufacture, also referred to herein as a kit, refers to a packaged product comprising the automatic injection device of the invention. The kit preferably comprises a box or container that holds the components of the kit, i.e., automatic injection device. In one embodiment, the automatic injection device, e.g., an autoinjector pen, is housed in a dose tray within the kit or article. The kit may also include instructions for administering a substance, such as a liquid drug, e.g., a TNFα antibody, to a patient using the automatic injection device of the invention. The term "package insert" is used to refer to instructions customarily included in commercial packages of therapeutic products, including liquid drugs, that contain information about the indications, usage, dosage, administration, contraindications and/or warnings concerning the use of such therapeutic products. In one embodiment, the package insert is the label for the therapeutic substance provided by the kit.

The kit or article of manufacture may include a label or a Food and Drug Administration approved label, which provides a protocol for using the automatic injection device for administering the substance, e.g., TNFα inhibitor. Thus, the invention also includes labels used alone or in combination with articles of manufacture which provide information to a patient regarding the automatic injection device, including information such as how to use the device, what substance, e.g., liquid dose, the device holds for administration to a patient, and how to dispose of the device once administration is complete. In one embodiment, the label is found on a package insert. In one embodiment, the label is a package insert that includes a Patient Information Leaflet which provides information to a patient regarding how to use the automatic injection device of the invention.

The kit or article of manufacture of the invention may contain information regarding the automatic injection device with respect to how the device is packaged within the kit or article. The kit may comprise a dose tray comprising the automatic injection device of the invention containing a substance, e.g., a TNFα inhibitor. In one embodiment, the dose tray is for single use of the device for delivering the agent. In another example, the kit may include 2 or more dose trays, each containing an automatic injection device, e.g., autoinjector pen. The kit or article of manufacture may also indicate related items needed for using the automatic injection device, e.g., alcohol preps, package insert with an attached patient information leaflet, and/or a patient information booklet. Such written material, e.g., package inserts with an attached patient information leaflet, and/or a patient information booklet, may be used to provide the recipient with information regarding administration techniques, common adverse events, disposal information, etc. In one embodiment, the kit or article of manufacture of the invention indicates in a manner visible from the outside of the packaging of the kit or article, that the kit or article contains 2 dose trays, 2 alcohol preps, one package insert with an attached patient information leaflet, and one patient information booklet.

The kit or article of manufacture of the invention may contain information, for example on a label, regarding how a liquid dose of a drug, e.g., a TNFα inhibitor, such as a TNFα antibody (adalimumab), is packaged within the automatic injection device, e.g, autoinjector pen, of the invention. For example, in one embodiment, the label of the invention may indicate that adalimumab is dispensed in a carton containing 6 alcohol preps and 6 dose trays (Crohn's Disease Starter Package). In one embodiment, the label also may indicate each dose tray consists of a single-use pen each pen, containing a 1 mL prefilled glass syringe with a fixed 27 gauge ½ inch needle, providing 40 mg (0.8 mL) of HUMIRA®.

In one embodiment the kit or article of manufacture of the invention includes information indicating that the automatic injection device provided within the kit comprises a formulation comprising the human antibody adalimumab (adalimumab/HUMIRA®/D2E7), as described in PCT/IB03/04502 and U.S. application Ser. No. 10/222,140, incorporated by reference herein.

In one embodiment, the kit or article of manufacture of the invention may contain information, for example on a label, which describes that HUMIRA® is supplied as a sterile, preservative-free solution of adalimumab for subcutaneous administration. The label may further describe that the drug product is supplied as either a single-use, 1 mL prefilled glass syringe or as a single-use, prefilled pen (HUMIRA® Pen). The label of the invention may indicate that enclosed within the pen is a single-use, 1 mL prefilled glass syringe. The label of the invention may further indicate that the solution of HUMIRA® is clear and colorless, with a pH of about 5.2. The label may also indicate that HUMIRA® (adalimumab) is supplied in pre-filled syringes or in prefilled pens as a preservative-free, sterile solution for subcutaneous administration. In one embodiment, the label indicates that the automatic injection device of the invention containing adalimumab is provided in a HUMIRA® pen carton, wherein HUMIRA® is dispensed in a carton containing two alcohol preps and two dose trays. The label may further specify that each dose tray consists of at least one single-use pen, containing a 1 mL prefilled glass syringe with a fixed 27 gauge ½ inch needle, providing 40 mg (0.8 mL) of HUMIRA®.

The kit or article of manufacture of the invention may contain information, for example on a label, which provides information regarding how the automatic invention device should appear in the kit and/or how the substance contained within the automatic injection device, e.g., liquid drug, should appear. Such information may be provided to insure safety regarding the administration of the substance to a patient, such that a patient would know whether the kit and/or automatic injection device had been tampered with and/or whether the substance had been compromised such that administration should not be performed. In one embodiment, the label indicates that the solution in the HUMIRA® Pen should be carefully inspected visually for particulate matter and discoloration prior to subcutaneous administration.

The kit or article of manufacture of the invention may contain information, for example on a label, which provides instructions regarding how to use the automatic injection device of the invention, including administration of the substance, e.g., liquid drug, held within the device. In one embodiment, the label indicates that patients using the HUMIRA® Pen should be instructed to inject the full amount in the syringe (0.8 mL), which provides 40 mg of HUMIRA®, according to the directions provided in the Patient Information Leaflet.

The kit or article of manufacture of the invention may contain information, for example on a label, which provides instruction for preparing to use the pen of the invention. For example, the label may provide instructions for setting up for an injection with the pen. In one embodiment, the invention provides a pen filled with HUMIRA®, wherein a label for said pen may indicate that a patient will need the following items for each dose: one HUMIRA® Pen and 1 alcohol prep (swab). The label may also indicate that the patient should find a clean flat working surface. The label may also indicate that the pen should not be used if seals on top and bottom of carton are broken or missing, as well as, optionally, an indication that the patient should contact their pharmacist if the seals are broken. The label may indicate to a patient that he should remove one dose tray containing, for example, a pen of HUMIRA®, from the refrigerator (if the substance, e.g., liquid drug, requires refrigeration). Additionally, a label indicating use of pen filled with HUMIRA® may indicate that a patient should not use a Pen that is frozen or if it has been left in direct sunlight. The label may also indicate that if the patient does not have all of the pieces needed to give an injection, a pharmacist should be called. The label may also indicate that the patient should use only the items provided in the box the substance, e.g., HUMIRA®, comes in.

For labels of the invention relating to an autoinjector pen comprising adalimumab, the label may indicate that the patient should check and make sure the name HUMIRA® appears on the dose tray and pen label; that the patient should check the expiration date on the dose tray label and the pen label to make sure the date has not passed, and, further that the patient should not use a pen if the date has passed; and that the patient should have a puncture proof container nearby for disposing of the used pen.

The kit or article of manufacture may also contain material for use, either within the package or through accompanying information, for treatment of the disorders described herein. In one embodiment, the packaging is specific to a disorder that is being treated with a TNFα antibody, e.g., adalimumab. The kit or article of manufacture further can include a second agent (as described herein) packaged with or co-introduced with instructions for using the second agent with a first agent (as described herein).

Methods for using the automatic injection device of the invention are described in more detail below and in the Examples. Moreover, any of the methods described herein relating to the automatic injection device may be included in a label of the invention.

VI. Methods and Compositions for Use of an Automatic Injection Device

Methods and Compositions for Delivery of a Substance Using an Automatic Injection Device The invention also provides methods of using the automatic injection device of the invention for delivering a substance, e.g., medication or liquid dose of a drug such as a TNFα inhibitor. In one embodiment, the automatic injection device is an autoinjector pen, such as a HUMIRA® pen.

Included in the methods are methods for preparing to use the automatic injection device, e.g., autoinjector pen, of the invention.

Use of the automatic injection device may require that a patient first choose and prepare an injection site. For example, methods for choosing and preparing an injection site for administration with an autoinjector pen, such as the HUMIRA® pen, include first washing the hands of the patient thoroughly. Generally, a clean and healthy part of the patient's body is selected to receive the injection from the automatic injection device. In one embodiment, a site is chosen on the front of the patient's thighs or abdomen. If the abdomen is chosen, the patient should avoid the area 2 inches around the navel. For injection with an autoinjector pen, such as a HUMIRA® pen, a different site should be chosen each time an injection is given. Each new injection should be given at least one inch from a site used previously. Areas where the skin is tender, bruised, red or hard or where there are scars or stretch marks should generally not be used as injection sites. A patient may find it helpful to keep notes on the location of previous injections.

Once an injection site is selected, the patient generally cleans the area. In one embodiment, the site where HUMIRA® is to be injected is first wiped with an alcohol prep (swab), using a circular motion. Once cleaned, the injection site area should not be touched again until the patient is ready to inject.

The methods of the invention also include preparing the dose of the substance within the automatic injection device, e.g., autoinjector pen, to be injected. In one embodiment, the autoinjector pen is held with the first removable cap pointing up. The patient should examine the solution or substance, e.g., liquid drug, through the windows on the side of the automatic injection device, e.g., autoinjector pen, to make sure, for example, the liquid is clear and colorless. Generally, the automatic injection device, e.g., autoinjector pen, should not be used if the liquid is cloudy or discolored or has flakes or particles in it. In addition, an automatic injection device, e.g., autoinjector pen, comprising adalimumab should be not used if it is frozen.

Once it has been determined that the automatic injection device, e.g., autoinjector pen, is satisfactory for use in and injection, the device may be held with the first removable cap pointed down. Such an action may serve to determine the level of the liquid drug within the automatic injection device, e.g., autoinjector pen.

In one embodiment, prior to injection, one should check to make sure that the amount of liquid in the automatic injection device, e.g., autoinjector pen, is the same or close to the line visible through the window. In one embodiment, the line represents a full dose of the product. The top of the liquid may be curved. If the automatic injection device, e.g., autoinjector pen, does not have the correct amount of liquid, the autoinjector pen should not be used and, optionally, a pharmacist should be called.

Injection methods for delivering a substance, such as a liquid drug, using the automatic injection device, e.g., autoinjector pen, of the invention may include the following. The automatic injection device, e.g., autoinjector pen, is held with one hand. With the patient's other hand, the first removable cap is removed and discarded. In one embodiment, the first removable cap should be pulled straight off and/or should not be twisted. Following removal of the first removable cap, the patient should check that the needle sheath of the syringe has come off with the first removable cap. After removal, the interior needle cover is held in the cap. The needle housed in the syringe barrel should not be touched. The distal end of the stepped shroud will be exposed following removal of the first removable cap. The first removable cap should not be recapped as the needle may be damaged. In addition, the patient should take care to avoid dropping or crushing the automatic injection device, e.g., autoinjector pen, as it contains a syringe.

Following removal of the first removable cap, the second removable cap (also referred to as a safety cap) is removed to expose the activation button at the top. The patient should pull the second removable cap straight off. The second removable cap should not be twisted off. Following removal of the first and second removable caps, the automatic injection device, e.g., an autoinjector pen, is now ready to use. The patient should be aware that the automatic injection device, e.g., an autoinjector pen, is activated after removing the second removable cap, and, furthermore, that pressing the activation button under the second removable cap will result in discharge of medication. The patient should also be aware that the activation button should not be removed until properly positioned. In addition, at this point the automatic injection device, e.g., an autoinjector pen, should not be recapped, as this may cause the unit to discharge.

Once the patient is ready to deliver the injection, the automatic injection device, e.g., an autoinjector pen, should be positioned so that the window is in view. With the patient's free hand, a sizable area of the cleaned skin may be gently squeezed at the injection site, creating a platform on which to position the automatic injection device, e.g., an autoinjector pen. The proximal end of the automatic injection device, e.g., an autoinjector pen, may be positioned the at a 90 degree angle flush against the platform of skin. The automatic injection device, e.g., so that it will not inject the needle into the patient's fingers. To begin injection, the activation button is pressed. In one embodiment, the activation button is pressed using a finger, e.g., the index finger of the patient, to begin the injection. Alternatively, in another embodiment, the patient may also use a thumb to press the activation button to begin the injection. During the injection, the patient should try not to cover the window. In one embodiment, when the activation button is pressed, there will be an audible indicator, e.g, click. The audible indicator, e.g., click, may indicate the start of the injection. In one embodiment, an autoinjector pen comprising adalimumab makes noise once the activation button is pressed. Once the activation button is pressed, pressure should be kept on the activation button and the patient may continue to hold the automatic injection device, e.g., autoinjector pen, with steady pressure on the injection site until the process is finished. In one embodiment, the process of pressing the activation button to complete the injection may take up to about 10 seconds. For injection, constant pressure is maintained at the injection site for the entire period of time.

Using the automatic injection device, e.g., autoinjector pen, of the invention, a patient will know that the injection has finished when the indicator in the window appears in full view and stops. When the injection is finished, the automatic injection device, e.g., autoinjector pen, is pulled from the skin of the user. The shroud will automatically advance over the needle tip. The patient may press a cotton ball over the injection site and hold it, e.g., for 10 seconds. The patient should not rub the injection site, and should not be alarmed if there is slight bleeding. Following injection, the automatic injection device, e.g., autoinjector pen, should be disposed of, such that the patient tries not to touch the needle. The needle sleeve prevents the patient from touching the needle.

It should be noted that any of the instructions recited in the methods for using the automatic injection device of the invention may be included in a label for the automatic injection device, e.g., autoinjector pen, of the invention.

Methods and Compositions for Training a Recipient for Use of an Automatic Injection Device Another aspect of the invention pertains to methods and compositions for training a recipient in the use of an automatic injection device. Based on experience in use of the device in clinical studies, particular important features for successful use of the device have now been discovered and these features can be incorporated into business methods for training recipients in the use of the automatic injection device. Such training methods, and compositions used in such methods, are beneficial for communicating to an end user of the device, or to a party that will introduce, prescribe or sell the device to an end user, important features for successful use of the device.

Moreover, the use of a demonstration automatic injection device or trainer device that mimics the look and feel of the actual automatic injection device but which is incapable of administering the substance or medication, is particularly useful in training a recipient in the successful use of the actual automatic injection device, since it allows the recipient to experience and practice the handling and control of the device without the possibility of inadvertently administering the medication.

Accordingly, in one aspect, the invention provides a method of training a recipient on use of an automatic injection device, wherein the automatic injection device comprises a needle and a medication, the method comprising providing to the recipient:

(a) a demonstration automatic injection device which lacks the needle and the medication; and (b) instructions for using the automatic injection device.

In another aspect, the invention provides a kit for training a recipient on use of an automatic injection device, wherein the automatic injection device comprises a needle and a medication, the kit comprising:

(a) a demonstration automatic injection device which lacks the needle and the medication; and (b) instructions for using the automatic injection device.

In a preferred embodiment, the recipient is a physician that prescribes the medication contained within the automatic injection device. In another embodiment, the recipient is a patient that uses the medication contained within the automatic injection device. Other examples of recipients include pharmacists that dispense the automatic injection device, family members or other caregivers of patients that use the medication and representatives that train physicians or patients in use of the automatic injection device.

In certain embodiments of the method, including the training methods described herein, the instructions for using the automatic injection device are conveyed orally to the recipient. In other preferred embodiments, instructions are conveyed in writing (e.g., via a printed document) or via an audiovisual device to the recipient. In the kits of the invention, the instructions for using the automatic injection device typically are contained with a printed document or audiovisual device. Preferred audiovisual devices include VHS cassettes and DVDs.

The demonstration automatic injection device is designed to look and feel like the actual automatic injection device, but lacks at least one component necessary to allow for successful administration of a medication by an end user and most preferably at least lacks a needle such that inadvertent needle pricks are avoided when using the demonstration automatic injection device. Preferably, the demonstration automatic injection device lacks both the needle and the medication that is contained in the actual automatic injection device.

In another aspect, the invention provides a method of training a recipient on use of an automatic injection device, wherein the automatic injection device comprises an activator mechanism and a medication, the method comprising conveying to the recipient instructions to:

(a) position the automatic injection device at an injection site;

(b) engage the activator mechanism to begin injection of the medication;

(c) maintain engagement of the activator mechanism for a prescribed period of time to continue injection of the medication; and (d) remove the automatic injection device from the injection site after passage of the prescribed period of time.

The invention also provides an audiovisual device for training a recipient on use of an automatic injection device, wherein the automatic injection device comprises an activator mechanism and a medication, the audiovisual device conveying to the recipient instructions to:

(a) position the automatic injection device at an injection site;

(b) engage the activator mechanism to begin injection of the medication;

(c) maintain engagement of the activator mechanism for a prescribed period of time to continue injection of the medication; and (d) remove the automatic injection device from the injection site after passage of the prescribed period of time.

Preferably, the audiovisual device is an VHS cassette or an DVD.

In the above training methods and audiovisual devices, the instructions can further convey that initial engagement of the activator mechanism is accompanied by an audible sound, such as a "click". Other examples of audible sounds include a bell, a buzzer or a ring-tone.

In other embodiments of the above training methods and audiovisual devices, the instructions can further convey that completion of injection of the medication is accompanied by a visible indicator of completion and/or the instructions can further convey that the injection site should be sterilized prior to positioning the automatic injection device at the injection site Other examples of instruction that can be conveyed in the above training methods and audiovisual devices are described in further detail in Example 4.

In yet another aspect, the invention provides a method of training a recipient on use of an automatic injection device, wherein the automatic injection device comprises an activator mechanism and a medication, the method comprising conveying to the recipient instructions to:

(a) position the automatic injection device at an injection site;

(b) engage the activator mechanism to begin injection of the medication;

(c) maintain engagement of the activator mechanism to continue injection of the medication until a visible indicator of completion is detected; and (d) remove the automatic injection device from the injection site once the visible indicator of completion is detected.

The invention also provides an audiovisual device for training a recipient on use of an automatic injection device, wherein the automatic injection device comprises an activator mechanism and a medication, the audiovisual device conveying to the recipient instructions to:

(a) position the automatic injection device at an injection site;

(b) engage the activator mechanism to begin injection of the medication;

(c) maintain engagement of the activator mechanism to continue injection of the medication until a visible indicator of completion is detected; and (d) remove the automatic injection device from the injection site once the visible indicator of completion is detected.

Preferably, the automatic injection device comprises an indicator window and the visible indicator of completion comprises a color indicator appearing in the indicator window. A preferred color indicator is a yellow color indicator. Other examples of suitable color indicators include red, orange, blue, green, pink or purple color indicators. Other examples of visible indicators of completion include the appearance of a symbol or design in an indicator window upon completion of injection and appearance of a "pop-up" button on the automatic injection device upon completion of injection.

In other embodiments of the above training methods and audiovisual devices, the instructions can further convey that engagement of the activator mechanism should be maintained for a prescribed period of time to continue injection of the medication and/or the instructions can further convey that the injection site should be sterilized prior to positioning the automatic injection device at the injection site. Preferably the prescribed period of time is 10 seconds. Another preferred prescribed period of time is at least 10 seconds. In various other embodiments, the prescribed period of time is 1 second, 2 seconds, 3 seconds, 4 seconds, 5 seconds, 6 seconds, 7 seconds, 8 seconds, 9 seconds, 11 seconds, 12 seconds, 13 seconds, 14 seconds, 15 seconds, 30 seconds, 45 seconds or 1 minute.

In another embodiment of the above training methods and audiovisual devices, the instructions further convey that the automatic injection device should be examined for proper dosage and formulation of the medication prior to positioning the automatic injection device at the injection site. Such examination can be done, for example, by looking at the medication through a window present in the automatic injection device that allows for visualization of the liquid medication contained in the device. Examples of examination for proper dosage and formulation include examining whether the medication is clear and colorless (e.g., is not cloudy and does not contain particulate matter) and examining whether the level of medication is the same as or close to a "fill-line" indication visible in the window. Other examples of instruction that can be conveyed in the above training methods and audiovisual devices are described in further detail in Example 4.

VII. Methods and Compositions for Promoting Use of an Automatic Injection Device One aspect of the invention pertains to methods and compositions for promoting the use of an automatic injection device. Based on the results of clinical studies, advantageous features of an automatic injection device have now been discovered and these features can be incorporated into business methods for promoting the use of the automatic injection device. Such promotional methods, and compositions used in such methods, are beneficial for communicating to an end user of the device, or to a party that will introduce, prescribe or sell the device to an end user, the advantageous features of the device.

Accordingly, in one aspect, the invention provides a method of promoting an automatic injection device comprising a substance, such as a medication, to a recipient, the method comprising conveying to the recipient at least one message selected from the group consisting of:
  (a) the automatic injection device is less painful for a patient to use than a pre-filled syringe;
  (b) the automatic injection device is preferred for use by patients as compared to a pre-filled syringe;
  (c) the automatic injection device is easier to use by a patient than a pre-filled syringe;
  (d) the automatic injection device is more convenient for a patient to use than a pre-filled syringe;
  (e) the automatic injection device reduces anxiety of patients with a fear of needles, as compared to a pre-filled syringe, since the needle is not visible in the device; and
  (f) the automatic injection device is designed to be easy to use from initial use of the device.

In a preferred embodiment, the message that the automatic injection device is less painful for a patient to use than a pre-filled syringe is conveyed to the recipient. For example, a message that 80% of patients in a clinical trial rated the automatic injection device as less painful than a pre-filled syringe can be conveyed to the recipient.

In another preferred embodiment, the message that the automatic injection device is preferred for use by patients as compared to a pre-filled syringe is conveyed to the recipient. For example, a message that 90% of patients in a clinical trial preferred the automatic injection device to a pre-filled syringe can be conveyed to the recipient.

Particular structural features of the automatic injection device also can be conveyed to the recipient. For example, a message that the automatic injection device comprises a five-bevel needle, as compared to a three-bevel needle for a pre-filled syringe, additionally can be conveyed to the recipient. As another example, a message that the needle is not visible in the device (i.e., not visible to the user of the device when the device is used as instructed) can be conveyed to the recipient.

In a preferred embodiment, the recipient is a physician that prescribes the medication contained within the automatic injection device. In another embodiment, the recipient is a patient that uses the medication contained within the automatic injection device. Other examples of recipients include pharmacists that dispense the automatic injection device, family members or caretakers thereof, of patients that use the medication and representatives that train physicians or patients in use of the automatic injection device.

In a preferred embodiment, the at least one message is conveyed orally to the recipient. In another preferred embodiment, the at least one message is conveyed in writing to said recipient (e.g., via a printed document, such as a package insert). In yet another preferred embodiment, the at least one message is conveyed to the recipient via an audiovisual device.

In another aspect, the invention provides an audiovisual device for promoting an automatic injection device comprising a medication to a recipient, wherein the device conveys to the recipient at least one message selected from the group consisting of:
  (a) the automatic injection device is less painful for a patient to use than a pre-filled syringe;
  (b) the automatic injection device is preferred for use by patients as compared to a pre-filled syringe;
  (c) the automatic injection device is easier to use by a patient than a pre-filled syringe;
  (d) the automatic injection device is more convenient for a patient to use than a pre-filled syringe;
  (e) the automatic injection device reduces anxiety of patients with a fear of needles, as compared to a pre-filled syringe, since the needle is not visible in the device; and
  (f) the automatic injection device is designed to be easy to use from initial use of the device.

In a preferred embodiment, the audiovisual device is a Video Home System (VHS) cassette. In another preferred embodiment, the audiovisual device is a Digital Video Disc (DVD).

In a preferred embodiment, the audiovisual device conveys the message that the automatic injection device is less painful for a patient to use than a pre-filled syringe. For example, the audiovisual device can convey a message that 80% of patients in a clinical trial rated the automatic injection device as less painful than a pre-filled syringe.

In another preferred embodiment, the audiovisual device conveys the message that the automatic injection device is preferred for use by patients as compared to a pre-filled syringe. For example, the audiovisual device can convey a message that 90% of patients in a clinical trial preferred the automatic injection device to a pre-filled syringe.

The audiovisual device also can convey particular structural features of the automatic injection device to the recipient. For example, the audiovisual device can convey a message that the automatic injection device comprises a five-bevel needle, as compared to a three-bevel needle for a pre-filled syringe. As another example, the audiovisual device can convey a message that the needle is not visible in the device (i.e., not visible to the user of the device when the device is used as instructed).

In still other embodiments, an automatic injection device previously described in the art is used in the methods and compositions of the invention relating to training and promoting an automatic injection device. Suitable automatic injection devices have been described in the art, including but not limited to the devices described in U.S. Pat. Nos. 3,941,130; 4,261,358; 5,085,642; 5,092,843; 5,102,393; 5,267,963; 6,149,626; 6,270,479; and 6,371,939.

VII. Disorders in which TNFα Activity is Detrimental which can be Treated with a TNFα Inhbitor Using an Automatic Injection Device The automatic injection device, e.g., autoinjector pen, of the invention may be used in methods of treating disorders, including, in one embodiment, disorders associated with detrimental TNF activity. In one embodiment, the automatic injection device, e.g., autoinjector pen, is used to deliver a substance, e.g., a TNFα inhibitor, to a patient for treatment, wherein the disorder includes, but not limited to, rheumatoid arthritis (including juvenile arthritis), Crohn's disease, psoriasis, psoriatic arthritis, and ankylosing spondylitis.

As used herein, the term "a disorder in which TNFα activity is detrimental" is intended to include diseases and other disorders in which the presence of TNFα in a patient suffering from the disorder has been shown to be or is suspected of being either responsible for the pathophysiology of the disorder or a factor that contributes to a worsening of the disorder. Accordingly, a disorder in which TNFα activity is detrimental is a disorder in which inhibition of TNFα activity is expected to alleviate the symptoms and/or progression of the disorder. Such disorders may be evidenced, for example, by an increase in the concentration of TNFα in a biological fluid of a patient suffering from the disorder (e.g., an increase in the concentration of TNFα in serum, plasma, synovial fluid, etc. of the patient), which can be detected, for example, using an anti-TNFα antibody as described above. There are numerous examples of disorders in which TNFα activity is detrimental which are discussed further below:

A. Autoimmune Diseases

Tumor necrosis factor has been implicated in playing a role in the pathophysiology of a variety of autoimmune diseases. For example, TNFα has been implicated in activating tissue inflammation and causing joint destruction in rheumatoid arthritis (see e.g., Moeller, A., et al. (1990) *Cytokine* 2:162-169; U.S. Pat. No. 5,231,024 to Moeller et al.; European Patent Publication No. 260 610 B1 by Moeller, A.; Tracey and Cerami, supra; Arend, W. P. and Dayer, J-M. (1995) *Arth. Rheum.* 38:151-160; Fava, R. A., et al. (1993) *Clin. Exp. Immunol.* 94:261-266). TNFα also has been implicated in promoting the death of islet cells and in mediating insulin resistance in diabetes (see e.g., Tracey and Cerami, supra; PCT Publication No. WO 94/08609). TNFα also has been implicated in mediating cytotoxicity to oligodendrocytes and induction of inflammatory plaques in multiple sclerosis (see e.g., Tracey and Cerami, supra). TNFα also has been implicated in mediating cytotoxicity to oligodendrocytes and induction of inflammatory plaques in multiple sclerosis (see e.g., Tracey and Cerami, supra). Chimeric and humanized murine anti-hTNFα antibodies have undergone clinical testing for treatment of rheumatoid arthritis (see e.g., Elliott, M. J., et al. (1994) *Lancet* 344:1125-1127; Elliot, M. J., et al. (1994) *Lancet* 344:1105-1110; Rankin, E. C., et al. (1995) *Br. J. Rheumatol.* 34:334-342).

TNFα antibodies, such as adalimumab, may be used to treat autoimmune diseases, in particular those associated with inflammation. Examples of such autoimmune conditions include rheumatoid arthritis, rheumatoid spondylitis, osteoarthritis and gouty arthritis, allergy, multiple sclerosis, autoimmune diabetes, autoimmune uveitis and nephrotic syndrome. Other examples of autoimmune conditions include multisystem autoimmune diseases and autoimmune hearing loss.

In one embodiment of the invention, a TNFα inhibitor is used to treat autoimmune disorders such as lupus. Lupus is has been shown to be associated with TNF activity (Shvidel et al. (2002) *Hematol J.* 3:32; Studnicka-Benke et al. (1996) *Br J Rheumatol.* 35:1067). The term "lupus" as used herein refers to a chronic, inflammatory autoimmune disorder called lupus erythematosus that may affect many organ systems including the skin, joints and internal organs. Lupus is a general term which includes a number of specific types of lupus, including systemic lupus, lupus nephritis, and lupus cerebritis. In systemic lupus (SLE), the body's natural defenses are turned against the body and rogue immune cells attack the body's tissues. Antibodies may be produced that can react against the body's blood cells, organs, and tissues. This reaction leads to immune cells attacking the affected systems, producing a chronic disease. Lupus nephritis, also referred to as lupus glomerular disease, is kidney disorder that is usually a complication of SLE, and is characterized by damage to the glomerulus and progressive loss of kidney function. Lupus cerebritis refers to another complication of SLE, which is inflammation of the brain and/or central nervous system.

Another autoimmune disease which can be treated using a TNFα antibody is Crohn's disease, which is described in more detail below in the Intestinal Disorders Section.

B. Intestinal Disorders

Tumor necrosis factor has been implicated in the pathophysiology of inflammatory bowel disorders including Crohn's disease (see e.g., Tracy et al. (1986) *Science* 234:470; Sun et al. (1988) *J. Clin. Invest.* 81:1328; MacDonald et al. (1990) *Clin. Exp. Immunol.* 81:301). Chimeric murine anti-hTNFα antibodies have undergone clinical testing for treatment of Crohn's disease (van Dullemen et al. (1995) *Gastroenterology* 109:129). The invention includes treatment comprising administering a TNFα antibody obtained using the method of the invention to treat intestinal disorders, such as idiopathic inflammatory bowel disease, using human antibodies, or antigen-binding fragments thereof. Idiopathic inflammatory bowel disease includes two syndromes, Crohn's disease and ulcerative colitis. In one embodiment, an antibody obtained using the method of the invention is also used to treat disorders often associated with IBD and Crohn's disease. The term "inflammatory bowel disorder (IBD)-related disorder" or "Crohn's disease-related disorder," as used interchangeably herein, is used to describe conditions and complications commonly associated with IBD and Crohn's disease.

The invention also includes a multiple-variable dose regimen comprising administering a TNFα antibody to treat Crohn's disease. The treatment of Crohn's disease is based on location, extent, and severity of disease. Pharmacologic interventions include anti-inflammatory agents (aminosalicylates and corticosteroids) and immunomodulatory agents (azathioprine and 6-mercaptopurine [6-MP], cyclosporine, methotrexate [MTX], antibiotic agents, and biologic agents). C-reactive protein (CRP) and erythrocyte sedimentation rate (ESR) levels reflect non-specific acute phase reactions. Endoscopy is a primary means of diagnosing Crohn's disease. Radiologic features of Crohn's disease are shown by barium examination includes mucosal edema, aphthous and linear ulcerations, asymmetrical narrowing and strictures, and separation of adjacent loops of bowel caused by mesenteric thickening. Abnormalities are focal and asymmetric. The primary histologic lesion is an aphthous ulcer. Subjects with Crohn's disease can be evaluated using the Crohn's Disease Activity Index (CDAI), which is a standard measure of the severity of the disease with higher scores indicating more severe disease activity.

Examples of Crohn's disease-related disorders that can be treated using the methods of the invention include fistulas in the bladder, vagina, and skin; bowel obstructions; abscesses;

nutritional deficiencies; complications from corticosteroid use; inflammation of the joints; erythem nodosum; pyoderma gangrenosum; and lesions of the eye. Other disorders commonly associated with Crohn's disease include Crohn's-related arthralgias, fistulizing Crohn's, indeterminant colitis, and pouchitis.

C. Spondyloarthropathies

TNFα has been implicated in the pathophysiology of a wide variety of disorders, including inflammatory diseases such as spondyloarthopathies (see e.g., Moeller et al. (1990) *Cytokine* 2:162; U.S. Pat. No. 5,231,024; European Patent Publication No. 260 610). The invention provides multiple-variable dose methods for inhibiting TNFα activity in a patient suffering from a spondyloarthropathy, which method comprises administering to the patient an antibody, antibody portion, such that TNFα activity in the patient suffering from a spondyloarthropathy is inhibited.

As used herein, the term "spondyloarthropathy" or "spondyloarthropathies" is used to refer to any one of several diseases affecting the joints of the spine, wherein such diseases share common clinical, radiological, and histological features. A number of spondyloarthropathies share genetic characteristics, i.e. they are associated with the HLA-B27 allele. In one embodiment, the term spondyloarthropathy is used to refer to any one of several diseases affecting the joints of the spine, excluding ankylosing spondylitis, wherein such diseases share common clinical, radiological, and histological features. Examples of spondyloarthropathies include ankylosing spondylitis, psoriatic arthritis/spondylitis, enteropathic arthritis, reactive arthritis or Reiter's syndrome, and undifferentiated spondyloarthropathies. Examples of animal models used to study spondyloarthropathies include ank/ank transgenic mice, HLA-B27 transgenic rats (see Taurog et al. (1998) *The Spondylarthritides*. Oxford:Oxford University Press).

The automatic injection device of the invention can also be used to treat patients who are at risk of developing a spondyloarthropathy using multiple-variable dose methods. Examples of patients who are at risk of having spondyloarthropathies include humans suffering from arthritis. Spondyloarthropathies can be associated with other forms of arthritis, including rheumatoid arthritis. In one embodiment of the invention, antibodies are used in multiple-variable dose methods to treat a patient who suffers from a spondyloarthropathy associated with rheumatoid arthritis. Examples of spondyloarthropathies that can be treated with a TNFα antibody are described below:

1. Ankylosing Spondylitis (AS)

Tumor necrosis factor has been implicated in the pathophysiology of ankylosing spondylitis (see Verjans et al. (1991) *Arthritis Rheum.* 34:486; Verjans et al. (1994) *Clin Exp Immunol.* 97:45; Kaijtzel et al. (1999) *Hum Immunol.* 60:140). Ankylosing spondylitis (AS) is an inflammatory disorder involving inflammation of one or more vertebrae. AS is a chronic inflammatory disease that affects the axial skeleton and/or peripheral joints, including joints between the vertebrae of the spine and sacroiliac joints and the joints between the spine and the pelvis. AS can eventually cause the affected vertebrae to fuse or grow together. Spondyarthropathies, including AS, can be associated with psoriatic arthritis (PsA) and/or inflammatory bowel disease (IBD), including ulcerative colitis and Crohn's disease.

Early manifestations of AS can be determined by radiographic tests, including CT scans and MRI scans. Early manifestations of AS often include scroiliitis and changes in the sacroliac joints as evidenced by the blurring of the cortical margins of the subchrondral bone, followed by erosions and sclerosis. Fatigue has also been noted as a common symptom of AS (Duffy et al. (2002) *ACR 66th Annual Scientific Meeting* Abstract). Accordingly, multiple-variable dose methods comprising administering an antibody, or antigen-binding fragment thereof, of the invention can be used to treat AS.

In one embodiment, the multiple-variable dose method of the invention is used to treat a spondyloarthropathy associated with IBD, including AS. AS is often treated with non-steroidal anti-inflammatory medications (NSAIDs), such as aspirin or indomethacin. Accordingly, a TNFα antibody used in the multiple-variable dose method of the invention may also be administered in combination with agents commonly used to reduce inflammation and pain commonly associated with ankylosing spondylitis.

2. Psoriatic Arthritis

Tumor necrosis factor has been implicated in the pathophysiology of psoriatic arthritis (PsA) (Partsch et al. (1998) *Ann Rheum Dis.* 57:691; Ritchlin et al. (1998) *J Rheumatol.* 25:1544). As referred to herein, psoriatic arthritis or psoriasis associated with the skin, refers to chronic inflammatory arthritis which is associated with psoriasis, which is a common chronic skin condition that causes red patches on the body. About 1 in 20 individuals with psoriasis will develop arthritis along with the skin condition, and in about 75% of cases, psoriasis precedes the arthritis. PsA exhibits itself in a variety of ways, ranging from mild to severe arthritis, wherein the arthritis usually affects the fingers and the spine. When the spine is affected, the symptoms are similar to those of ankylosing spondylitis, as described above. The TNFα antibody, or antigen-binding fragment thereof, obtained using the invention can be used for treatment of PsA.

PsA is sometimes associated with arthritis mutilans. Arthritis mutilans refers to a disorder that is characterized by excessive bone erosion resulting in a gross, erosive deformity that mutilates the joint. In one embodiment, antibodies obtained using the method of the invention are used to treat arthritis mutilans.

3. Reactive Arthritis/Reiter's Syndrome

Tumor necrosis factor has been implicated in the pathophysiology of reactive arthritis, which is also referred to as Reiter's syndrome (Braun et al. (1999) *Arthritis Rheum.* 42(10):2039). Reactive arthritis (ReA) refers to arthritis that complicates an infection elsewhere in the body, often following enteric or urogenital infections. ReA is often characterized by certain clinical symptoms, including inflammation of the joints (arthritis), urethritis, conjunctivitis, and lesions of the skin and mucous membranes. In addition, ReA can occurs following infection with a sexually transmitted disease or dysenteric infection, including chlamydia, campylobacter, salmonella, or yersinia. Accordingly, antibodies obtained using the method of the invention may be used to treat ReA.

4. Undifferentiated Spondyloarthropathies

In one embodiment, antibodies obtained using methods of the invention are used to treat patients suffering from undifferentiated spondyloarthropathies (see Zeidler et al. (1992) *Rheum Dis Clin North Am.* 18:187). Other terms used to describe undifferentiated spondyloarthropathies include seronegative oligoarthritis and undifferentiated oligoarthritis. Undifferentiated spondyloarthropathies, as used herein, refers to a disorder wherein the patient demonstrates only some of the symptoms associated with a spondyloarthropathy. This condition is usually observed in young adults who do not have IBD, psoriasis, or the classic symptoms of AS or Reiter's syndrome. In some instances, undifferentiated spondyloarthropathies may be an early indication of AS. In one embodiment, the invention comprises administering a TNFα antibody, or antigen-binding fragment thereof, obtained using the claimed process to treat undifferentiated spondyloarthropathies.

D. Skin and Nail Disorders

Tumor necrosis factor has been implicated in the pathophysiology of skin and nail disorders. The term "skin disorder" or "skin disease" as used interchangeably herein, refers to abnormalities, other than injury wounds, of the skin that have induced a state of inflammation. In one embodiment, the skin disorder of the invention is an inflammatory skin disorder, wherein the skin is characterized by capillary dilatation, leukocytic infiltration, redness, heat, and/or pain. Examples of skin disorders include, but are not limited to, psoriasis, pemphigus vulgaris, scleroderma, atopic dermatitis, sarcoidosis, erythema nodosum, hidradenitis suppurative, lichen planus, Sweet's syndrome, and vitiligo. As used herein, the term "skin and nail disorder in which TNFα activity is detrimental" is intended to include skin and/or nail disorders and other disorders in which the presence of TNFα in a patient suffering from the disorder has been shown to be or is suspected of being either responsible for the pathophysiology of the disorder or a factor that contributes to a worsening of the disorder, e.g., psoriasis. Accordingly, skin and nail disorders in which TNFα activity is detrimental are disorders in which inhibition of TNFα activity is expected to alleviate the symptoms and/or progression of the disorder. The use of the antibodies, antibody portions, and other TNFα inhibitors of the invention in the treatment of specific skin and nail disorders is discussed further below. In certain embodiments, the treatment method of the invention is performed in combination with another therapeutic agent, as described below. In one embodiment, the antibodies obtained using the method of the invention comprising administering a TNFα antibody in combination with another therapeutic agent is used for the treatment of psoriasis and the treatment of psoriasis associated with arthritis.

1. Psoriasis

Tumor necrosis factor has been implicated in the pathophysiology of psoriasis (Takematsu et al. (1989) *Arch Dermatol Res.* 281:398; Victor and Gottlieb (2002) *J Drugs Dermatol.* 1:264). The term "psoriasis" as used herein, refers to skin disorders associated with epidermal hyperplasia. Examples of psoriasis include, but are not limited to, chronic plaque psoriasis, guttate psoriasis, inverse psoriasis, pustular psoriasis, psoriasis vulgaris, and erythrodermic psoriasis. Psoriasis can also be associated with other inflammatory disorders, including inflammatory bowel disease (IBD) and rheumatoid arthritis (RA).

Psoriasis is described as a skin inflammation (irritation and redness) characterized by frequent episodes of redness, itching, and thick, dry, silvery scales on the skin. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the epidermis and polymorphonuclear leukocyte and lymphocyte infiltration into the epidermis layer resulting in an increase in the basal cell cycle. Psoriasis often involves the nails, which frequently exhibit pitting, separation of the nail, thickening, and discoloration. Psoriasis is often associated with other inflammatory disorders, for example arthritis, including rheumatoid arthritis, inflammatory bowel disease (IBD), and Crohn's disease. Approximately one thrid of patients with psoriasis also have psoriatic arthritis (PsA) which, as described above, causes stiffness, swelling of the joints, pain, and reducd range of motion (Greaves et al. (1995) *N. Eng. J. Med.* 332:581).

Evidence of psoriasis is most commonly seen on the trunk, elbows, knees, scalp, skin folds, or fingernails, but it may affect any or all parts of the skin. Normally, it takes about a month for new skin cells to move up from the lower layers to the surface. In psoriasis, this process takes only a few days, resulting in a build-up of dead skin cells and formation of thick scales. Symptoms of psoriasis include: skin patches, that are dry or red, covered with silvery scales, raised patches of skin, accompanied by red borders, that may crack and become painful, and that are usually located on the elbows, knees, trunk, scalp, and hands; skin lesions, including pustules, cracking of the skin, and skin redness; joint pain or aching which may be associated with of arthritis, e.g., psoriatic arthritis.

Treatment for psoriasis often includes a topical corticosteroids, vitamin D analogs, and topical or oral retinoids, or combinations thereof In one embodiment, the TNFα antibody of the invention is administered in combination with or the presence of one of these common treatments. Additional therapeutic agents that can be combined with the TNFα antibody obtained using the methods of the invention for treatment of psoriasis are described in more detail below.

The diagnosis of psoriasis is usually based on the appearance of the skin. Additionally a skin biopsy, or scraping and culture of skin patches may be needed to rule out other skin disorders. An x-ray may be used to check for psoriatic arthritis if joint pain is present and persistent.

Improvements in psoriasis in a patient can be monitored by the patient's Psoriasis Area and Severity Index Score (PASI). The method for determining the PASI has been described in Fredriksson and Pettersson (1978) *Dermatologica* 157:238 and Marks et al. (1989) *Arch Dermatol* 125:235. Briefly, the index is based on evaluation of four anatomic sites, including the head, upper extremities, trunk, and lower extremities, for erythema, induration, and desquamation using a 5 point scale (0=no symptoms; 1=slight; 2=moderate; 3=marked; 4=very marked). Based on the extent of lesions in a given anatomic site, the area affected is assigned a numerical value (0=0; 1=<10%; 2=10-29%; 3=30-49%; 4=50-69%; 5=70=89%; 6=90-100%). The PASI score is then calculated, wherein the possible range of PASI score is 0.0 to 72.0 with the highest score representing complete erythroderma of the severest degree.

In one embodiment of the invention, a TNFα antibody is used for the treatment of psoriasis, including chronic plaque psoriasis, guttate psoriasis, inverse psoriasis, pustular psoriasis, pemphigus vulgaris, erythrodermic psoriasis, psoriasis associated with inflammatory bowel disease (IBD), and psoriasis associated with rheumatoid arthritis (RA). In another embodiment, a TNFα antibody, such as adalimumab, is used to treat patients who have psoriasis in combination with PsA. Specific types of psoriasis included in the treatment methods of the invention are described in detail below:

a. Chronic Plaque Psoriasis

Tumor necrosis factor has been implicated in the pathophysiology of chronic plaque psoriasis (Asadullah et al. (1999) *Br J Dermatol.* 141:94). Chronic plaque psoriasis (also referred to as psoriasis vulgaris) is the most common form of psoriasis. Chronic plaque psoriasis is characterized by raised reddened patches of skin, ranging from coin-sized to much larger. In chronic plaque psoriasis, the plaques may be single or multiple, they may vary in size from a few millimeters to several centimeters. The plaques are usually red with a scaly surface, and reflect light when gently scratched, creating a "silvery" effect. Lesions (which are often symmetrical) from chronic plaque psoriasis occur all over body, but with predilection for extensor surfaces, including the knees, elbows, lumbosacral regions, scalp, and nails. Occasionally chronic plaque psoriasis can occur on the penis, vulva and flexures, but scaling is usually absent. Diagnosis of patients with chronic plaque psoriasis is usually based on the clinical features described above. In particular, the distribution, color and typical silvery scaling of the lesion in chronic plaque psoriasis are characteristic of chronic plaque psoriasis.

b. Guttate Psoriasis

Guttate psoriasis refers to a form of psoriasis with characteristic water drop shaped scaly plaques. Flares of guttate psoriasis generally follow an infection, most notably a streptococcal throat infection. Diagnosis of guttate psoriasis is usually based on the appearance of the skin, and the fact that there is often a history of recent sore throat.

c. Inverse Psoriasis

Inverse psoriasis is a form of psoriasis in which the patient has smooth, usually moist areas of skin that are red and inflammed, which is unlike the scaling associated with plaque psoriasis. Inverse psoriasis is also referred to as intertiginous psoriasis or flexural psoriasis. Inverse psoriasis occurs mostly in the armpits, groin, under the breasts and in other skin folds around the genitals and buttocks, and, as a result of the locations of presentation, rubbing and sweating can irriate the affected areas.

d. Pustular Psoriasis

Pustular psoriasis, also referred to as palmar plantar psoriasis, is a form of psoriasis that causes pus-filled blisters that vary in size and location, but often occur on the hands and feet. The blisters may be localized, or spread over large areas of the body. Pustular psoriasis can be both tender and painful, can cause fevers.

e. Other Psoriasis Disorders

Other examples of psoriatic disorders that can be treated with a TNFα antibody delivered using the methods of the invention include erythrodermic psoriasis, vulgaris, psoriasis associated with IBD, and psoriasis associated with arthritis, including rheumatoid arthritis.

2. Pemphigus Vulgaris

Pemphigus vulgaris is a serious autoimmune systemic dermatologic disease that often affects the oral mucous membrane and skin. The pathogenesis of pemphigus vulgaris is thought to be an autoimmune process that is directed at skin and oral mucous membrane desmosomes. Consequentially, cells do not adhere to each other. The disorder manifests as large fluid-filled, rupture-prone bullae, and has a distinctive histologic appearance. Anti-inflammatory agents are the only effective therapy for this disease that has a high mortality rate. Complications that arise in patients suffering from pemphigus vulgaris are intractable pain, interference with nutrition and fluid loss, and infections.

3. Atopic Dermatitis/Eczema

Atopic dermatitis (also referred to as eczema) is a chronic skin disorder categorized by scaly and itching plaques. People with eczema often have a family history of allergic conditions like asthma, hay fever, or eczema. Atopic dermatitis is a hypersensitivity reaction (similar to an allergy) which occurs in the skin, causing chronic inflammation. The inflammation causes the skin to become itchy and scaly. Chronic irritation and scratching can cause the skin to thicken and become leathery-textured. Exposure to environmental irritants can worsen symptoms, as can dryness of the skin, exposure to water, temperature changes, and stress.

Subjects with atopic dermatitis can be identified by certain symptoms, which often include intense itching, blisters with oozing and crusting, skin redness or inflammation around the blisters, rash, dry, leathery skin areas, raw areas of the skin from scratching, and ear discharges/bleeding.

4. Sarcoidosis

Sarcoidosis is a disease in which granulomatous inflammation occurs in the lymph nodes, lungs, liver, eyes, skin, and/or other tissues. Sarcoidosis includes cutaneous sarcoidosis (sarcoidosis of the skin) and nodular sarcoidosis (sarcoidosis of the lymph nodes). Patients with sarcoidosis can be identified by the symptoms, which often include general discomfort, uneasiness, or an ill feeling; fever; skin lesions.

5. Erythema Nodosum

Erythema nodosum refers to an inflammatory disorder that is characterized by tender, red nodules under the skin, typically on the anterior lower legs. Lesions associated with erythema nodosum often begin as flat, but firm, hot red painful lumps (approximately an inch across). Within a few days the lesions may become purplish, and then over several weeks fade to a brownish flat patch.

In some instances, erythema nodosum may be associated with infections including, streptococcus, coccidioidomycosis, tuberculosis, hepatitis B, syphilis, cat scratch disease, tularemia, yersinia, leptospirosis psittacosis, histoplasmosis, mononucleosis (EBV). In other instances, erythema nodosum may be associated with sensitivity to certain medications including, oralcontraceptives, penicillin, sulfonamides, sulfones, barbiturates, hydantoin, phenacetin, salicylates, iodides, and progestin. Erythema nodosum is often associated with other disorders including, leukemia, sarcoidosis, rheumatic fever, and ulcerative colitis.

Symptoms of erythema nodosum usually present themselves on the shins, but lesions may also occur on other areas of the body, including the buttocks, calves, ankles, thighs and upper extremities. Other symptoms in patients with erythema nodosum can include fever and malaise.

6. Hidradenitis Suppurative

Hidradenitis suppurativa refers to a skin disorder in which swollen, painful, inflamed lesions or lumps develop in the groin and sometimes under the arms and under the breasts. Hidradenitis suppurativa occurs when apocrine gland outlets become blocked by perspiration or are unable to drain normally because of incomplete gland development. Secretions trapped in the glands force perspiration and bacteria into surrounding tissue, causing subcutaneous induration, inflammation, and infection. Hidradenitis suppurativa is confined to areas of the body that contain apocrine glands. These areas are the axillae, areola of the nipple, groin, perineum, circumanal, and periumbilical regions.

7. Lichen Planus

Tumor necrosis factor has been implicated in the pathophysiology of lichen planus (Sklavounou et al. (2000) *J Oral Pathol Med.* 29:370). Lichen planus refers to a disorder of the skin and the mucous membranes resulting in inflammation, itching, and distinctive skin lesions. Lichen planus may be associated with hepatitis C or certain medications.

8. Sweet's Syndrome

Inflammatory cytokines, including tumor necrosis factor, have been implicated in the pathophysiology of Sweet's syndrome (Reuss-Borst et al. (1993) *Br J Haematol.* 84:356). Sweet's syndrome, which was described by R. D. Sweet in 1964, is characterized by the sudden onset of fever, leukocytosis, and cutaneous eruption. The eruption consists of tender, erythematous, well-demarcated papules and plaques which show dense neutrophilic infiltrates microscopically. The lesions may appear anywhere, but favor the upper body including the face. The individual lesions are often described as pseudovesicular or pseudopustular, but may be frankly pustular, bullous, or ulcerative. Oral and eye involvement (conjunctivitis or episcleritis) have also been frequently reported in patients with Sweet's syndrome. Leukemia has also been associated with Sweet's syndrome.

9. Vitiligo

Vitiligo refers to a skin condition in which there is loss of pigment from areas of skin resulting in irregular white patches with normal skin texture. Lesions characteristic of vitiligo appear as flat depigmented areas. The edges of the lesions are sharply defined but irregular. Frequently affected areas in patients with vitiligo include the face, elbows and knees, hands and feet, and genitalia.

10. Scleroderma

Tumor necrosis factor has been implicated in the pathophysiology of scleroderma (Tutuncu et al. (2002) *Clin Exp Rheumatol.* 20(6 Suppl 28):S146; Mackiewicz et al. (2003) *Clin Exp Rheumatol.* 21:41; Murota et al. (2003) *Arthritis Rheum.* 48:1117). Scleroderma refers to a a diffuse connective tissue disease characterized by changes in the skin, blood vessels, skeletal muscles, and internal organs. Scleroderma is also referred to as CREST syndrome or progressive systemic sclerosis, and usually affects people between the ages 30-50. Women are affected more often than men.

The cause of scleroderma is unknown. The disease may produce local or systemic symptoms. The course and severity of the disease varies widely in those affected.Excess collagen deposits in the skin and other organs produce the symptoms. Damage to small blood vessels within the skin and affected organs also occurs. In the skin, ulceration, calcification, and changes in pigmentation may occur. Systemic features may include fibrosis and degeneration of the heart, lungs, kidneys and gastrointestinal tract.

Patients suffering from scleroderma exhibit certain clinical features, including, blanching, blueness, or redness of fingers and toes in response to heat and cold (Raynaud's phenomenon), pain, stiffness, and swelling of fingers and joints, skin thickening and shiny hands and forearm, esophageal reflux or heartburn, difficulty swallowing, and shortness of breath. Other clinical sypmtoms used to diagnose scleroderma include, an elevated erythrocyte sedimentaion rate (ESR), an elevated rheumatoid factor (RF), a positive antinuclear antibody test, urinalysis that shows protein and microscopic blood, a chest X-ray that may show fibrosis, and pulmonary funtion studies that show restricitive lung disease.

11. Nail Disorders

Nail disorders include any abnormality of the nail. The term "nail disorder" or "nail disease" as used herein, refers to conditions wherein the fingernails or toenails to abnormal color, shape, texture, or thickness. Specific nail disorders include, but are not limited to, pitting, koilonychia, Beau's lines, spoon nails, onycholysis, yellow nails, pterygium (seen in lichen planus), and leukonychia. Pitting is characterised by the presence of small depressions on the nail surface. Ridges or linear elevations can develop along the nail occurring in a "lengthwise" or "crosswise" direction. Beau's lines are linear depressions that occur "crosswise" (transverse) in the fingernail. Leukonychia describes white streaks or spots on the nails. Koilonychia is an abnormal shape of the fingernail where the nail has raised ridges and is thin and concave Koilonychia is often associated with iron deficiency.

Nail disorders that can be treated with the TNFα antibody of the invention alsoinclude psoriatic nails. Psoriatic nails include changes in nails that are attributable to psoriasis. In some instances psoriasis may occur only in the nails and nowhere else on the body. Psoriatic changes in nails range from mild to severe, generally reflecting the extent of psoriatic involvement of the nail plate, nail matrix, i.e., tissue from which the nail grows, nail bed, i.e., tissue under the nail, and skin at the base of the nail. Damage to the nail bed by the pustular type of psoriasis can result in loss of the nail. Nail changes in psoriasis fall into general categories that may occur singly or all together. In one category of psoriatic nails, the nail plate is deeply pitted, probably due to defects in nail growth caused by psoriasis. In another category, the nail has a yellow to yellow-pink discoloration, probably due to psoriatic involvement of the nail bed. A third subtype of psoriatic nails is characterized by white areas, which appear under the nail plate. The white areas are actually air bubbles marking spots where the nail plate is becoming detached from the nail bed. There may also be reddened skin around the nail. A fourth category is evidenced by the nail plate crumbling in yellowish patches, i.e., onychodystrophy, probably due to psoriatic involvement in the nail matrix. A fifth category is characterized by the loss of the nail in its entirety due to psoriatic involvement of the nail matrix and nail bed.

Antbodies obtained using the method of the invention can also be used to treat nail disorders often associated with lichen planus. Nails in patients with lichen planus often show thinning and surface roughness of the nail plate with longitudinal ridges or pterygium.

The antibodies obtained using the invention can be used to treat nail disorders, such as those described herein. Often nail disorders are associated with skin disorders. In one embodiment, the invention includes treatment for nail disorders using a TNFα antibody and the methods and compositions of the invention. In another embodiment, the nail disorder is associated with another disorder, including a skin disorder such as psoriasis. In another embodiment, the disorder associated with a nail disorder is arthritis, including psoriatic arthritis.

12. Other Skin and Nail Disorders

Antbodies obtained using the method of the invention can be used to treat other skin and nail disorders, such as chronic actinic dermatitis, bullous pemphigoid, and alopecia areata. Chronic actinic dermatitis (CAD) is also referred to as photosensitivity dermatitis/actinic reticuloid syndrome (PD/AR). CAD is a condition in which the skin becomes inflamed, particularly in areas that have been exposed to sunlight or artificial light. Commonly, CAD patients have allergies to certain substances that come into contact with their skin, particularly various flowers, woods, perfumes, sunscreens and rubber compounds. Bullous pemphigoid refers to a skin disorder characterized by the formation of large blisters on the trunk and extremities. Alopecia areata refers to hair loss characterized by round patches of complete baldness in the scalp or beard.

E. Other TNFα-Related Disorders

In one embodiment, the invention features a multiple-variable dose method for treating a TNFα-related disorder in which TNFα activity is detrimental, comprising administering to a patient a TNFα antibody, such that said TNFα-related disorder is treated. Examples of TNFα-related disorders in which TNFα activity is detrimental, are discussed further below.

1. Juvenile Arthritis

Tumor necrosis factor has been implicated in the pathophysiology of juvenile arthritis, including juvenile rheumatoid arthritis (Grom et al. (1996) *Arthritis Rheum.* 39:1703; Mangge et al. (1995) *Arthritis Rheum.* 8:211). In one embodiment, a TNFα antibody is used to treat juvenile rheumatoid arthritis using the methods and compositions of the invention.

The term "juvenile rheumatoid arthritis" or "JRA" as used herein refers to a chronic, inflammatory disease thatoccurs before age 16 that may cause joint or connective tissue damage. JRA is also referred to as juvenile chronic polyarthritis and Still's disease.

JRA causes joint inflammation and stiffness for more than 6 weeks in a child of 16 years of age or less. Inflammation causes redness, swelling, warmth, and soreness in the joints. Any joint can be affected and inflammation may limit the mobility of affected joints. One type of JRA can also affect the internal organs.

JRA is often classified into three types by the number of joints involved, the symptoms, and the presence or absence of certain antibodies found by a blood test. These classifications help the physician determine how the disease will progress and whether the internal organs or skin is affected. The classifications of JRA include the following:

a. Pauciarticular JRA, wherein four or fewer joints are affected. Pauciarticular is the most common form of JRA, and typically affects large joints, such as the knees.

b. Polyarticular HRA, wherein five or more joints are affected. The small joints, such as those in the hands and feet, are most commonly involved, but the disease may also affect large joints.

c. Systemic JRA is characterized by joint swelling, fever, a light skin rash, and may also affect internal organs such as the heart, liver, spleen, and lymph nodes. Systemic JRA is also referred to as it Still's disease. A small percentage of these children develop arthritis in many joints and can have severe arthritis that continues into adulthood.

2. Endometriosis

Tumor necrosis factor has been implicated in the pathophysiology of endometriosis, as women with endometriosis have elevated peritoneal levels of TNF (Eisermann et al. (1988) *Fertil Steril* 50:573; Halme (1989) *Am J Obstet Gynecol* 161:1718; Mori et al. (1991) *Am J Reprod Immunol* 26:62; Taketani et al. (1992) *Am J Obstet Gynecol* 167:265; Overton et al. (1996) *Hum Reprod* 1996; 11:380). In one embodiment, the TNFα antibody may be used to treat endometriosis. The term "endometriosis" as used herein refers to a condition in which the tissue that normally lines the uterus (endometrium) grows in other areas of the body, causing pain, irregular bleeding, and frequently infertility.

3. Prostatitis

Tumor necrosis factor has been implicated in the pathophysiology of prostatitis, as men with chronic prostatitis and chronic pelvic pain have significantly higher levels of TNF and IL-1 in semen compared to controls (Alexander et al. (1998) *Urology* 52:744; Nadler et al. (2000) *J Urol* 164:214; Orhan et al. (2001) *Int J Urol* 8:495) Furthermore, in a rat model of prostatitis TNF levels were also increased in comparison to controls (Asakawa et al. (2001) *Hinyokika Kiyo* 47:459; Harris et al. (2000) *Prostate* 44:25). In one embodiment, the TNFα antibody of the invention is used to treat prostatitis.

The term "prostatitis" as used herein refers to an inflammation of the prostate. Prostatitis is also referred to as pelvic pain syndrome. Prostatitis manifests itself in a variety of forms, including nonbacterial prostatitis, acute prostatitis, bacterial prostatitis, and acute prostatitis. Acute prostatitis refers to an inflammation of the prostate gland that develops suddenly. Acute prostatitis is usually caused by a bacterial infection of the prostate gland. Chronic prostatitis is an inflammation of the prostate gland that develops gradually, continues for a prolonged period, and typically has subtle symptoms. Chronic prostatitis is also usually caused by a bacterial infection 4. Choroidal Neovascularization Tumor necrosis factor has been implicated in the pathophysiology of choroidal neovascularization. For example, in surgically excised choroidal neovascular membranes, neovascular vessels stained positive for both TNF and IL-1 (Oh H et al. (1999) *Invest Ophthalmol Vis Sci* 40:1891). In one embodiment, the TNFα antibody is used to treat choroidal neovascularization. The term "choroidal neovascularization" as used herein refers to the growth of new blood vessels that originate from the choroid through a break in the Bruch membrane into the subretinal pigment epithelium (sub-RPE) or subretinal space. Choroidal neovascularization (CNV) is a major cause of visual loss in patients with the condition.

5. Sciatica

Tumor necrosis factor has been implicated in the pathophysiology of sciatica (Ozaktay et al. (2002) *Eur Spine J.* 11:467; Brisby et al. (2002) *Eur Spine J.* 11:62). In one embodiment, the TNFα antibody of the invention is used to treat sciatica. The term "sciatica" as used herein refers to a condition involving impaired movement and/or sensation in the leg, caused by damage to the sciatic nerve. Sciatica is also commonly referred to as neuropathy of the sciatic nerve and sciatic nerve dysfunction. Sciatica is a form of peripheral neuropathy. It occurs when there is damage to the sciatic nerve, located in the back of the leg. The sciatic nerve controls the muscles of the back of the knee and lower leg and provides sensation to the back of the thigh, part of the lower leg and the sole of the foot. Sciatica can be indicative of another disorder, including a lumbar herniated disc, spinal stenosis, degenerative disc disease, isthmic spondyloisthesis and piniformis syndrome.

6. Sjogren's Syndrome

Tumor necrosis factor has been implicated in the pathophysiology of Sjogren's syndrome (Koski et al. (2001) *Clin Exp Rheumatol.* 19:131). In one embodiment, the TNFα antibody of the invention is used to treat Sjogren's syndrome. The term "Sjogren's syndrome" as used herein refers to a systemic inflammatory disorder characterized by dry mouth, decreased tearing, and other dry mucous membranes, and is often associated with autoimmune rheumatic disorders, such as rheumatoid arthritis. Dryness of the eyes and mouth are the most common symptoms of this syndrome. The symptoms may occur alone, or with symptoms associated with rheumatoid arthritis or other connective tissue diseases. There may be an associated enlargement of the salivary glands. Other organs may become affected. The syndrome may be associated with rheumatoid arthritis, systemic lupus erythematosus, scleroderma, polymyositis, and other diseases.

7. Uveitis

Tumor necrosis factor has been implicated in the pathophysiology of uveitis (Wakefield and Lloyd (1992) *Cytokine* 4:1; Woon et al. (1998) *Curr Eye Res.* 17:955). In one embodiment, the TNFα antibody of the invention is used to treat uveitis. The term "uveitis" as used herein refers to an inflammation of the the uvea, which is the layer between the sclera and the retina, which includes the iris, ciliary body, and the choroid. Uveitis is also commonly referred to as iritis, pars planitis, chroiditis, chorioretinitis, anterior uveitis, and posterior uveitis. The most common form of uveitis is anterior uveitis, which involves inflammation in the front part of the eye, which is usually isolated to the iris. This condition is often called iritis. In one embodiment, the term uveitis refers to an inflammation of the the uvea which excludes inflammation associated with an autoimmune disease, i.e., excludes autoimmune uveitis.

8. Wet Macular Degeneration

Tumor necrosis factor has been implicated in the pathophysiology of wet macular degeneration. In one embodiment, the TNFα antibody of the invention is used to treat wet macular degeneration. The term "wet macular degeneration" as used herein refers to a disorder that affects the macula (the central part of the retina of the eye) and causes decreased visual acuity and possible loss of central vision. Patients with wet macular degeneration develop new blood vessels under the retina, which causes hemorrhage, swelling, and scar tissue.

9. Osteoporosis

Tumor necrosis factor has been implicated in the pathophysiology of osteoporosis, (Tsutsumimoto et al. (1999) *J Bone Miner Res.* 14:1751). Osteoporosis is used to refer to a disorder characterized by the progressive loss of bone density and thinning of bone tissue. Osteoporosis occurs when the body fails to form enough new bone, or when too much old bone is reabsorbed by the body, or both. The TNFα antibody, or antigen-binding fragment thereof, of the invention can be used to treat osteoporosis.

10. Osteoarthritis

Tumor necrosis factor has been implicated in the pathophysiology of osteoarthritis, (Venn et al. (1993) *Arthritis Rheum.* 36:819; Westacott et al. (1994) *J Rheumatol.* 21:1710). Osteoarthritis (OA) is also referred to as hypertrophic osteoarthritis, osteoarthrosis, and degenerative joint disease. OA is a chronic degenerative disease of skeletal joints, which affects specific joints, commonly knees, hips, hand joints and spine, in adults of all ages. OA is characterized by a number of the following manifestations including degeneration and thinning of the articular cartilage with associated development of "ulcers" or craters, osteophyte formation, hypertrophy of bone at the margins, and changes in the synovial membrane and enlargement of affected joints. Furthermore, osteoarthritis is accompanied by pain and stiffness, particularly after prolonged activity. The antibody, or antigen-binding fragment thereof, of the invention can be used to treat osteoarthritis. Characteristic radiographic features of osteoarthritis include joint space narrowing, subchondral sclerosis, osteophytosis, subchondral cyst formation, loose osseous body (or "joint mouse").

Medications used to treat osteoarthritis include a variety of nonsteroidal, anti-inflammatory drugs (NSAIDs). In addition, COX 2 inhibitors, including the CELEBREX™ anti-inflammatory drug, the VIOXX™ anti-inflammatory drug Vioxx, and the BEXTRA™ anti-inflammatory drug, and Etoricoxib, are also used to treat OA. Steroids, which are injected directly into the joint, may also be used to reduce inflammation and pain. In one embodiment of the invention, TNFα antibodies of the invention are administered in combination with a NSAIDs, a COX2 inhibitor, and/or steroids.

11. Other

The methods of the invention also can be used to treat various other disorders in which TNFα activity is detrimental. Examples of other diseases and disorders in which TNFα activity has been implicated in the pathophysiology, and thus which can be treated using an antibody, or antibody portion, of the invention, include inflammatory bone disorders, bone resorption disease, coagulation disturbances, burns, reperfusion injury, keloid formation, scar tissue formation, pyrexia, periodontal disease, obesity, radiation toxicity, age-related cachexia, Alzheimer's disease, brain edema, inflammatory brain injury, cancer, chronic fatigue syndrome, dermatomyositis, drug reactions, such as Stevens-Johnson syndrome and Jarisch-Herxheimer reaction, edema in and/or around the spinal cord, familial periodic fevers, Felty's syndrome, fibrosis, glomerulonephritides (e.g. post-streptococcal glomerulonephritis or IgA nephropathy), loosening of prostheses, microscopic polyangiitis, mixed connective tissue disorder, multiple myeloma, cancer and cachexia, multiple organ disorder, myelo dysplastic syndrome, orchitism osteolysis, pancreatitis, including acute, chronic, and pancreatic abscess, polymyositis, progressive renal failure, pseudogout, pyoderma gangrenosum, relapsing polychondritis, rheumatic heart disease, sarcoidosis, sclerosing cholangitis, stroke, thoracoabdominal aortic aneurysm repair (TAAA), TNF receptor associated periodic syndrome (TRAPS), symptoms related to Yellow Fever vaccination, inflammatory diseases associated with the ear, chronic ear inflammation, chronic otitis media with or without cholesteatoma, pediatric ear inflammation, myotosis, ovarian cancer, colorectal cancer, therapy associated with induced inflammatory syndrome (e.g., syndromes following IL-2 administration), and a disorder associated with a reperfussion injury.

The methods of the invention also can be used to treat the following diseases: Acquired Immunodeficiency Disease Syndrome, Acquired Immunodeficiency Related Diseases, acquired pernicious anaemia, acute coronary syndromes, acute and chronic pain (different forms of pain), acute Idiopathic Polyneuritis, acute immune disease associated with organ transplantation, acute or chronic immune disease associated with organ transplantation, acute Inflammatory Demyelinating Polyradiculoneuropathy, acute ischemia, acute liver disease, acute rheumatic fever, acute transverse myelitis, Addison's disease, adult (acute) respiratory distress syndrome, adult Still's Disease, alcoholic cirrhosis, alcohol-induced liver injury, allergic diseases, allergy, alopecia, Alopecia areata, Alzheimer's disease, Anaphylaxis, ankylosing spondylitis, ankylosing spondylitis associated lung disease, anti-Phospholipid Antibody Syndrome, aplastic anemia, Arteriosclerosis, arthropathy, asthma, atheromatous disease/arteriosclerosis, atherosclerosis, atopic allergy, Atopic eczema, Atopic dermatitis, atrophic autoimmune hypothyroidism, autoimmune bullous disease, Autoimmune dermatitis, autoimmune diabetes, Autoimmune disorder associated with Streptococcus infection, Autoimmune Enteropathy, autoimmune haemolytic anaemia, autoimmune hepatitis, Autoimmune hearing loss, Autoimmune Lymphoproliferative Syndrome (ALPS), autoimmune mediated hypoglycaemia, autoimmune myocarditis, autoimmune neutropenia, autoimmune premature ovarian failure, autoimmune thrombocytopenia (AITP), autoimmune thyroid disease, autoimmune uveitis, bronchiolitis obliterans, Behcet's disease, Blepharitis, Bronchiectasis, Bullous pemphigoid, cachexia, Cardiovascular Disease, Catastrophic Antiphospholipid Syndrome, Celiac Disease, Cervical Spondylosis, Chlamydia, choleosatatis, chronic active hepatitis, chronic eosinophilic pneumonia, chronic fatigue syndrome, chronic immune disease associated with organ transplantation, Chronic ischemia, chronic liver diseases, chronic mucocutaneous candidiasis, Cicatricial pemphigoid, Clinically isolated Syndrome (CIS) with Risk for Multiple Sclerosis, common varied immunodeficiency (common variable hypogammaglobulinaemia), connective tissue disease associated interstitial lung disease, Conjunctivitis, Coombs positive haemolytic anaemia, Childhood Onset Psychiatric Disorder, Chronic obstructive pulmonary disease (COPD), Crohn's disease, cryptogenic autoimmune hepatitis, cryptogenic fibrosing alveolitis, Dacryocystitis, depression , dermatitis scleroderma, dermatomyositis, dermatomyositis/polymyositis associated lung disease, Diabetic retinopathy, Diabetes mellitus, dilated cardiomyopathy, discoid lupus erythematosus, disk herniation, disk prolaps, disseminated intravascular coagulation, Drug-Induced hepatitis, drug-induced interstitial lung disease, Drug induced immune hemolytic anemia, Endocarditis, Endometriosis, endophthalmitis, enteropathic synovitis, Episcleritis, Erythema multiforme, erythema multiforme major, female infertility, fibrosis, fibrotic lung disease, Gestational pemphigoid, giant cell arteritis (GCA), glomerulonephritides, goitrous autoimmune hypothyroidism (Hashimoto's disease), Goodpasture's syndrome, gouty arthritis, graft versus host disease (GVHD), Grave's disease, group B streptococci (GBS) infection, Guillain-Barré Syndrome (GBS), haemosiderosis associated lung disease, Hay Fever, heart failure, hemolytic anemia, Henoch-Schoenlein purpurea, Hepatitis B, Hepatitis C, Hughes Syndrome, Huntington's chorea, hyperthyroidism, hypoparathyroidism, idiopathic leucopaenia, idiopathic, thrombocytopaenia, Idiopathic Parkinson's Disease, idiopathic interstitial pneumonia, idiosyncratic liver disease, IgE-mediated Allergy, Immune hemolytic anemia, Inclusion Body Myositis, infectious diseases, Infectious ocular inflammatory disease, inflammatory bowel disease, Inflammatory demyelinating disease, Inflammatory heart disease, Inflammatory kidney disease, insulin dependent diabetes mellitus, interstitial pneumonitis, IPF/UIP, Iritis, juvenile chronic arthritis, juvenile pernicious anaemia, Juvenile rheumatoid arthritis, Kawasaki's disease, Keratitis, Keratojuntivitis sicca, Kussmaul disease or Kussmaul-Meier Disease, Landry's Paralysis, Langerhan's Cell Histiocytosis, linear IgA disease, Livedo reticularis, Lyme arthritis, lymphocytic infiltrative lung disease, Macular Degeneration, male infertility idiopathic or NOS, malignancies, microscopic vasculitis of the kidneys, Microscopic Polyangiitis, mixed connective tissue disease associated lung disease, Morbus Bechterev, Motor Neuron Disorders, Mucous membrane pemphigoid, multiple sclerosis (all subtypes: primary progressive, secondary progressive, relapsing remitting etc.), Multiple Organ failure, myalgic encephalitis/Royal Free disease, Myasthenia Gravis, Myelodysplastic Syndrome, myocardial infarction, Myocarditis, nephrotic syndrome, Nerve Root Disorders, Neuropathy, Non-alcoholic Steatohepatitis, Non-A Non-B Hepatitis, optic neuritis, organ transplant rejection, osteoarthritis, Osteolysis, Ovarian cancer, ovarian failure, Pancreatitis, Parasitic diseases, Parkinson's disease, Pauciarticular JRA, pemphigoid, pemphigus foliaceus, pemphigus vulgaris, peripheral artery occlusive disease (PAOD), peripheral vascular disease (PVD), peripheral artery disease (PAD), phacogenic uveitis, Phlebitis, Polyarteritis nodosa (or periarteritis nodosa), Polychondritis, Polymyalgia Rheumatica, Poliosis, Polyarticular JRA, Polyendocrine Deficiency Syndrome, Polymyositis, polyglandular deficiency type I and polyglandular deficiency type II, polymyalgia rheumatica (PMR), postinfectious interstitial lung disease, post-inflammatory interstitial lung disease, Post-Pump Syndrome, premature ovarian failure, primary biliary cirrhosis, primary myxoedema, primary parkinsonism, primary sclerosing cholangitis, primary sclerosing hepatitis, primary vasculitis, prostate and rectal cancer and hematopoietic malignancies (leukemia and lymphoma), Prostatitis, psoriasis, psoriasis type 1, psoriasis type 2, psoriatic arthritis, psoriatic arthropathy, pulmonary hypertension secondary to connective tissue disease, pulmonary manifestation of polyarteritis nodosa, Pure red cell aplasia, Primary Adrenal Insufficiency, radiation fibrosis, reactive arthritis, Reiter's disease, Recurrent Neuromyelitis Optica, renal disease NOS, Restenosis, rheumatoid arthritis, rheumatoid arthritis associated interstitial lung disease, Rheumatic heart disease, SAPHO (synovitis, acne, pustulosis, hyperostosis, and osteitis), sarcoidosis, Schizophrenia, Schmidt's syndrome, Scleroderma, Secondary Amyloidosis, Shock lung, Scleritis, Sciatica, Secondary Adrenal Insufficiency, sepsis syndrome, septic arthritis, septic shock, seronegative arthopathy, Silicone associated connective tissue disease, Sjögren's disease associated lung disease, Sjörgren's syndrome, Sneddon-Wilkinson Dermatosis, sperm autoimmunity, spondyloarthropathy, spondilitis ankylosans, Sporadic, Stevens-Johnson Syndrome (SJS), Still's disease, stroke, sympathetic ophthalmia, Systemic inflammatory response syndrome, systemic lupus erythematosus, systemic lupus erythematosus associated lung disease, systemic sclerosis, systemic sclerosis associated interstitial lung disease, Takayasu's disease/arteritis, Temporal arteritis, Th2 Type and Th1 Type mediated diseases, thyroiditis, toxic shock syndrome, toxoplasmic retinitis, toxic epidermal necrolysis, Transverse myelitis, TRAPS (Tumor Necrosis Factor Receptor, type B insulin resistance with acanthosis nigricans, Type 1 allergic reaction, type-1 autoimmune hepatitis (classical autoimmune or lupoid hepatitis), type-2 autoimmune hepatitis (anti-LKM antibody hepatitis), Type II Diabetes, ulcerative colitic arthropathy, ulcerative colitis, Urticaria, Usual interstitial pneumonia (UIP), uveitis, vasculitic diffuse lung disease, Vasculitis, Vernal conjunctivitis, viral retinitis, vitiligo, Vogt-Koyanagi-Harada syndrome (VKH syndrome), Wegener's granulomatosis, Wet macular degeneration, Wound healing, yersinia and salmonella associated arthropathy.

Other examples of disorders that can be used in the methods and compositions of the invention are found in US Publication No. 2004-0126372.

It is understood that all of the above-mentioned TNFα-related disorders include both the adult and juvenile forms of the disease where appropriate. It is also understood that all of the above-mentioned disorders include both chronic and acute forms of the disease. In addition, the multiple-variable dose methods of the invention can be used to treat each of the above-mentioned TNFα-related disorders alone or in combination with one another, e.g., a patient who is suffering from uveitis and lupus.

The invention also includes an article of manufacture comprising a packaging material; an automatic injection device, e.g., autoinjector pen, containing a syringe filled with a TNFα inhibitor, such as adalimumab; and a label or package insert contained within the packaging material indicating that in studies of the TNFα inhibitor using the automatic injection device of the invention for the treatment of rheumatoid arthritis, the most common adverse events (AEs) were bronchitis, hypersensitivity, arthritic pain, cough and rhinitis.

Other examples of biological agents which may be administered to a user using the automatic injection device, e.g., autoinjector pen, of the invention include, but are not limited to, antibodies to or antagonists of human cytokines or growth factors, for example, TNF, LT, IL-1, IL-2, IL-3, IL-4, IL-5, IL-6, IL-7, IL-8, IL-15, IL-16, IL-18, IL-21, IL-23, interferons, EMAP-II, GM-CSF, FGF, and PDGF; antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD 154 (gp39 or CD4OL); Actemra (tocilizumab) humanized MAb against interleukin-6 (IL-6) receptor; TNFα converting enzyme (TACE) inhibitors; IL-1 inhibitors (Interleukin-1-converting enzyme inhibitors, IL-1 RA etc.); Interleukin 11; IL-18 antagonists including IL-18 antibodies or soluble IL-18 receptors, or IL-18binding proteins; non-depleting anti-CD4 inhibitors; antagonists of the co-stimulatory pathway CD80 (B7.1) or CD86 (B7.2) including antibodies, soluble receptors or antagonistic ligands; agents which interfere with signalling by proinflammatory cytokines such as TNFα or IL-1 e.g. IRAK, NIK, IKK, p38 or MAP kinase inhibitors); IL-1β converting enzyme (ICE) inhibitors; T-cell signalling inhibitors such as kinase inhibitors; metalloproteinase inhibitors; angiotensin converting enzyme inhibitors; soluble cytokine receptors and derivatives thereof (e.g. soluble p55 or p75 TNF receptors and the derivatives p75TNFRIgG (the ENBREL™ protein and p55TNFRIgG (Lenercept)), sIL-1RI, sIL-1RII, sIL-6R); antiinflammatory cytokines (e.g. IL-4, IL-10, IL-11, IL-13 and TGFb); Rituximab; IL-1 TRAP; MRA; CTLA4-Ig; IL-18 BP; anti-IL-18; anti-IL15; IDEC-CE9.1/SB 210396 (non-depleting primatized anti-CD4 antibody; IDEC/SmithKline; see e.g., *Arthritis & Rheumatism* (1995) Vol. 38, S185); DAB 486-IL-2 and/or DAB 389-IL-2 (IL-2 fusion proteins; Seragen; see e.g., *Arthritis & Rheumatism* (1993) Vol. 36, 1223); Anti-Tac (humanized anti-IL-2Ra; Protein Design Labs/Roche); IL-4 (anti-inflammatory cytokine; DNAX/Schering); IL-10 (SCH52000; recombinant IL-10, anti-inflammatory cytokine; DNAX/Schering); IL-10 and/or IL-4 agonists (e.g., agonist antibodies); IL-1RA (IL-1 receptor antagonist; Synergen/Amgen); anakinra (the KINERET™ interleukin-1 receptor antagonist/Amgen); TNF-bp/s-TNF (soluble TNF binding protein; see e.g., *Arthritis & Rheumatism* (1996) Vol. 39, No. 9 (supplement), 5284; Amer. J. Physiol. Heart and Circulatory Physiology (1995) Vol. 268, pp. 37-42); R973401 (phosphodiesterase Type IV inhibitor; see e.g., *Arthritis & Rheumatism* (1996) Vol. 39, No. 9 (supplement), S282); MK-966 (COX-2 Inhibitor; see e.g., *Arthritis & Rheumatism* (1996) Vol. 39, No. 9 (supplement), S81); Iloprost (see e.g., *Arthritis & Rheumatism* (1996) Vol. 39, No. 9 (supplement), S82); zap-70 and/or lck inhibitor (inhibitor of the tyrosine kinase zap-70 or lck); VEGF inhibitor and/or VEGF-R inhibitor (inhibitors of vascular endothelial cell growth factor or vascular endothelial cell growth factor receptor; inhibitors of angiogenesis); TNF-convertase inhibitors; anti-IL-12 antibodies; anti-IL-18 antibodies; interleukin-11 (see e.g., *Arthritis & Rheumatism* (1996) Vol. 39, No. 9 (supplement), S296); interleukin-13 (see e.g., *Arthritis & Rheumatism* (1996) Vol. 39, No. 9 (supplement), S308); interleukin-17 inhibitors (see e.g., *Arthritis & Rheumatism* (1996) Vol. 39, No. 9 (supplement), S120); anti-thymocyte globulin; anti-CD4-antibodies; CD5-toxins; ICAM-1 antisense phosphorothioate oligo-deoxynucleotides (ISIS 2302; Isis Pharmaceuticals, Inc.); soluble complement receptor 1 TP10; T Cell Sciences, Inc.), efalizumab, and anti-IL2R antibodies, including anti-IL12 antibody (ABT 874); anti-IL18 antibody (ABT 325); small molecule inhibitor of LCK; small molecule inhibitor of COT; anti-IL1 antibody; small molecule inhibitor of MK2; anti-CD 19 antibody; small molecule inhibitor of CXCR3; small molecule inhibitor of CCR5; small molecule inhibitor of CCR11anti-E/L selectin antibody; small molecule inhibitor of P2X7; small molecule inhibitor of IRAK-4; small molecule agonist of glucocorticoid receptor; anti-C5a receptor antibody; small molecule inhibitor of C5a receptor; anti-CD32antibody; and CD32 as a therapeutic protein.

Other examples of biological agents which may be administered to a user using the automatic injection device, e.g., autoinjector pen, of the application include, but are not limited to, small molecule inhibitor of KDR (ABT-123), small molecule inhibitor of Tie-2; methotrexate; prednisone; celecoxib; folic acid; hydroxychloroquine sulfate; rofecoxib; etanercept; infliximab; anakinra (the KINERET™ interleukin-1 receptor antagonist/Amgen); leflunomide; naproxen; valdecoxib; sulfasalazine; ibuprofen; methylprednisolone; meloxicam; methylprednisolone acetate; gold sodium thiomalate; aspirin; azathioprine; triamcinolone acetonide; propxyphene napsylate/apap; folate; nabumetone; diclofenac; piroxicam; etodolac; diclofenac sodium; oxaprozin; oxycodone hcl; hydrocodone bitartrate/apap; diclofenac sodium/misoprostol; fentanyl; anakinra, human recombinant; tramadol hcl; salsalate; sulindac; cyanocobalamin/fa/pyridoxine; acetaminophen; alendronate sodium; prednisolone; morphine sulfate; lidocaine hydrochloride; indomethacin; glucosamine sulfate/chondroitin; cyclosporine; sulfadiazine; amitriptyline hcl; oxycodone hcl/acetaminophen; olopatadine hcl; misoprostol; naproxen sodium; omeprazole; mycophenolate mofetil; cyclophosphamide; rituximab; IL-1 TRAP; MRA; CTLA4-IG; IL-18 BP; ABT-874; ABT-325 (anti-IL 18); anti-IL 15; BIRB-796; SCIO-469; VX-702; AMG-548; VX-740; Roflumilast; IC-485; CDC-801; and mesopram, antibiotics, including clarithromycin (the BIAXIN™ antibiotic), ciprofloxacin (the CIPRO™ antibiotic), and metronidazole (the FLAGYL™ antibiotic), mesalamine, prednisone, azathioprine, mercaptopurine, infliximab, budesonide, sulfasalazine, methylprednisolone sod succ, diphenoxylate/atrop sulf, loperamide hydrochloride, methotrexate, omeprazole, folate, ciprofloxacin/ dextrose-water, hydrocodone bitartrate/apap, tetracycline hydrochloride, fluocinonide, metronidazole, thimerosal/boric acid, hyoscyamine sulfate, cholestyramine/sucrose, ciprofloxacin hydrochloride, meperidine hydrochloride, midazolam hydrochloride, oxycodone hcl/acetaminophen, promethazine hydrochloride, sodium phosphate, sulfamethoxazole/trimethoprim, celecoxib, polycarbophil, propoxyphene napsylate, hydrocortisone, multivitamins, balsalazide disodium, codeine phosphate/apap, colesevelam hcl, cyanocobalamin, folic acid, levofloxacin, natalizumab, methylprednisolone, interferon-gamma, sargramostim (GM-CSF), nonsteroidal, anti-inflammatory drugs (NSAIDs), COX 2 inhibitors, including the CELEBREX™ anti-inflammatory drug, the VIOXX™ anti-inflammatory drug, and the BEXTRA™ anti-inflammatory drug, etoricoxib, ibuprofen, diclofenac and misoprostol, naproxen, meloxicam, indomethacin, diclofenac, celecoxib, rofecoxib, sulfasalazine, prednisone, methotrexate, azathioprine, minocyclin, prednisone, etanercept, and infliximab; rofecoxib; celecoxib; folic acid; sulfasalazine; naproxen; leflunomide; methylprednisolone acetate; indomethacin; hydroxychloroquine sulfate; sulindac; prednisone; betamethasone diprop augmented; infliximab; methotrexate; folate; triamcinolone acetonide; diclofenac; dimethylsulfoxide; piroxicam; diclofenac sodium; ketoprofen; meloxicam; prednisone; methylprednisolone; nabumetone; tolmetin sodium; calcipotriene; cyclosporine; diclofenac; sodium/misoprostol; fluocinonide; glucosamine sulfate; gold sodium thiomalate; hydrocodone; bitartrate/apap; ibuprofen; risedronate sodium; sulfadiazine; thioguanine; valdecoxib; alefacept; RAPTIVA® (efalizumab), small molecule inhibitor of KDR (ABT-123), small molecule inhibitor of Tie-2, calcipotriene, clobetasol propionate, triamcinolone acetonide, halobetasol propionate, tazarotene, methotrexate, fluocinonide, betamethasone diprop augmented, fluocinolone, acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, coal tar, diflorasone diacetate, etanercept, folate, lactic acid, methoxsalen, hc/bismuth subgal/znox/resor, methylprednisolone acetate, prednisone, sunscreen, salicylic acid, halcinonide, anthralin, clocortolone pivalate, coal extract, coal tar/salicylic acid, coal tar/salicylic acid/sulfur, desoximetasone, diazepam, emollient, pimecrolimus emollient, fluocinonide/emollient, mineral oil/castor oil/na lact, mineral oil/peanut oil, petroleum/ isopropyl myristate, psoralen, salicylic acid, soap/tribromsalan, thimerosal/boric acid, celecoxib, alefacept, RAPTIVA® (efalizumab), tacrolimus, pimecrolimus, PUVA, and sulfasalazine.

This invention is further illustrated by the following examples, which should not be construed as limiting. The contents of all references, patents and published patent applications cited throughout this application are incorporated herein by reference.

The following examples describe studies using an exemplary automatic injection device, e.g., autoinjector or autoinjection pen, of the invention. The exemplary autoinjector pen described in the following examples contains a human TNFα antibody, e.g., adalimumab (HUMIRA®) and is often referred to as the "HUMIRA® pen" below.

EXAMPLE 1

Use of Automatic Injection Device for Administering TNFα Inhibitor

Overview/Summary of Study

Adalimumab is a therapeutic monoclonal antibody for subcutaneous administration by 2 bioequivalent, single-use injection devices: a ready-to-use, prefilled syringe and an integrated, disposable delivery system, the autoinjection pen. Although pens have been shown to be preferred over syringes by patients requiring long-term subcutaneous administration of medications, there are no data on preference and pain in the use of biologics in patients with chronic inflammatory diseases. Thus, the objective of the following study (the TOUCH study) was to assess injection-site pain, safety, and patient preference of 2 delivery systems of adalimumab.

The objective of the TOUCH study (Trial Of Usability in Clinical settings of HUMIRA Autoinjector vs. Prefilled Syringe) was to assess which method of delivery rheumatoid arthritis patients preferred: the HUMIRA prefilled syringe that they were already using, or the new HUMIRA Pen.

Briefly, patients with rheumatoid arthritis (RA) were enrolled in a Phase II, multicenter, open-label, single-arm, sequential trial. Patients self-administered a standard dose of adalimumab subcutaneously every other week at each of 3 monitored clinical visits: Visit 1 (syringe), Visits 2 and 3 (pen). At each visit, patients rated their pain at 2 time points and provided their impressions of and preferences for each delivery system. Safety was evaluated throughout the study and 70 days after final study dose.

Overall, fifty-two patients were enrolled in the trial and completed all 3 visits. Forty patients (76.9%) reported that the pen was less painful than the syringe, 4 patients (7.7%) found the syringe to be less painful, and 8 patients (15.4%) had no preference. At Visits 2 and 3, patients had significant mean reductions in injection site pain immediately post-injection (−1.4 and −1.6, respectively, $p<0.01$) and 15-30 minutes post-injection (−0.6 at both time points, $p<0.01$). ~90% of patients found the pen more convenient and easier to use. Patients had statistically significant reductions in injection-pain scores from Visit 1 to Visit 2 and from Visit 1 to Visit 3. The types and cumulative frequency of AEs during the 2-wk period after the syringe injection and the 4-wk period after the 2 pen injections were comparable. Five patients (9.6%) reported AEs, including bronchitis, hypersensitivity, arthritic pain, cough and rhinitis after syringe injection and 8 (15.4%) after pen injection. There were no AEs leading to discontinuation. Thus, both delivery systems were safe, and no significant differences in adverse events were reported for either delivery system. In addition, 46 patients (88.5%) preferred the pen, 3 (5.8%) preferred the syringe, and 3 (5.8%) had no preference. Overall, patients evaluated the pen as easier to use, more convenient, requiring less time to inject, and safer.

In conclusion, patients experienced less pain self-administering adalimumab via the pen and preferred it over. the syringe. Further, patients perceived the pen to be easier to use and more convenient. No differences in safety events were reported between the 2 bioequivalent delivery systems.

Detailed Study

The following study was performed to assess which method of delivery patients (also referred to herein as users) preferred—either the HUMIRA® (also referred to as adalimumab) prefilled syringe (PFS) or the new HUMIRA® pen. The following study was also performed to compare the two modes of administration, including the level of injection-site pain of the 2 delivery systems.

The study design included a phase II, multicenter, open-label study, that included patients who had prior experience administering adalimumab using the prefilled syringe. Patients who were=18 years of age, had RA diagnosed according to the 1987 revised American College of Rheumatology criteria, and had been self-administering adalimumab 40 mg subcutaneously every other week via the prefilled syringe for at least 3 months were eligible to enroll. Major exclusion criteria included patients with a history of malignancy; patients who were immunocompromised or had a history of human immunodeficiency virus, demyelinating diseases, or poorly controlled chronic disease; patients with active infections requiring treatment; patients with active tuberculosis or a positive purified protein derivative test within the last 6 months; patients who received live investigational drugs within 30 days or 5 half-lives; patients who were regularly using any medication administered via subcutaneous injection except for adalimumab; and women who were pregnant or breastfeeding. Patients in this study were allowed to continue prestudy dosages of standard antirheumatic drug therapies.

Figure 25:
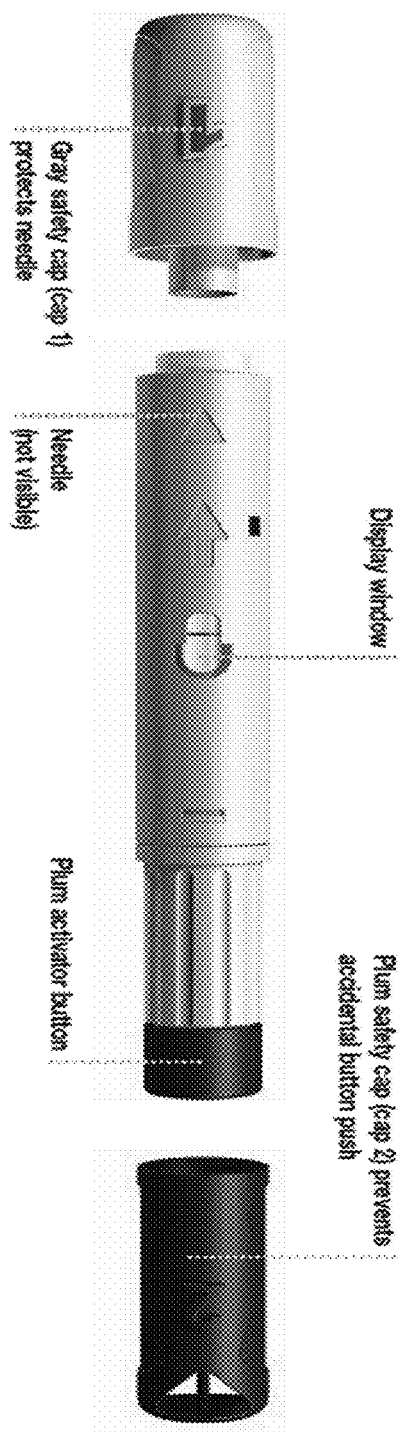
FIG. 25 illustrates a diagram of the autoinjection pen for self-administration of adalimumab.

Patients (n=52) self-injected with the HUMIRA® prefilled syringe at week 0 followed by injections of the HUMIRA® pen at weeks 2 and 4, completing questionnaires at all 3 time points. Patients rated their injection preference for several attributes, including overall preference, ease of use, convenience, time to complete injection, perceived safety, and pain. The study included 3 study visits for patient self-administration of adalimumab every other week. Each injection was administered under the supervision of a health care professional at each visit. At Visit 1, patients self-administered adalimumab 40 mg subcutaneously via a prefilled syringe held at a 45-degree angle to the skin. At Visit 2, patients were instructed by study personnel on proper administration of adalimumab via the pen and on the pen's features (FIG. 25), including the window for viewing the drug solution before injection and a yellow band to indicate complete injection; the sequential opening of safety caps to prevent accidental misfiring; and the proper positioning, grasp, and one-touch activation of the device. At Visits 2 and 3, patients self-administered adalimumab via the pen held at a 90-degree angle to the skin. Patients chose to self-inject in either the thigh or abdomen at Visit 1 and were monitored to ensure they used the same body location for injection at Visits 2 and 3, keeping each injection at least 2 inches from the previous injection site.

The pen was used by the patient according to the following protocol: patients were first familiarized with the pen by watching an instructional video and reading a 5-step brochure prior to the pen injection. Patients also used a demonstration pen to practice using the device prior to the pen injection. The steps for using the HUMIRA® pen included setting up the pen, wherein the pen was removed from the box and allowed to acclimate to room temperature by letting it sit for 15-20 minutes. The patient then swabs themselves with an alcohol swab prior to injection. The injection site was chosen and prepared. HUMIRA® was injected using the pen, such that the patient pressed the activation button. Once the "click" was heard, the injection began and lasted about 10 seconds. After 10 seconds or when the yellow stopped moving in the window, the injection was complete.

Baseline demographics for the study included patients who had been using the HUMIRA® PFS between 3-32 months, with a mean of 15.4 months. Patients reported that self-injection with PFS too <1 minute to 5 minutes, with an average of <1 minute. Baseline assessments included duration of adalimumab treatment, duration of self-administration of adalimumab, usual site of injection, length of time to inject, and overall impression of adalimumab administration via a syringe. Injection-site pain was rated on an 11-point numeric rating scale ranging from 0 (no pain) to 10 (pain as bad as it could be) at 2 time points post-injection: immediately post-injection and 15-30 minutes post-injection (Huskisson *Lancet.* 1974;304:1127-1131 and Jorgensen et al. *Annals of Pharmacotherapy.* 1996;30:729-732). Following each injection, patients also rated their overall impressions of the syringe vs. the pen as "extremely unfavorable," "unfavorable," "neutral," "favorable," or "extremely favorable."

At week 0, patients were asked the following information: the amount of time they have been on HUMIRA®, their typical injection site, their typical time of injection, and their overall impression of the syringe. The most common injection sites were the abdomen (25/52) and the thigh (22/52).

A patient preference survey was administered following the last visit or upon early termination from the study. The survey asked patients to rate their overall preferences (syringe, pen, or no preference) and the rationales for their preferences. Patient preference (syringe, pen, or no preference) was also rated for each of the following categories: ease of use, convenience, time to administer injection, safety, and less pain. Patients were also asked to rate their likelihood of switching to the pen if available at the same price ("extremely unlikely," "unlikely," "neutral," "likely," or "extremely likely"), and their likelihood of recommending the pen to another patient receiving adalimumab (same ratings as above). At the first and third injections (weeks 2 and 4), patients were asked to rate the immediate pain using the pen (scale of 0-10, wherein 0=no pain and 10=pain as bad as it could be), the amount of pain at 15-30 minutes (0-10 scale), their overall impression, their injection site, whether they experienced a wet or normal injection, their adherence to the instructions of the pen, and any additional comments.

At the end of the study, patients were given a final preference questionnaire to determine the following attributes: overall preference, as, well as reasons; specific preference, relating to ease of use, convenience, time of injection, safety, less pain; whether the patient would be likely to switch from the PFD to the pen; and whether the patient would be likely to recommend the pen to other patients using adalimumab.

Safety was assessed at baseline (for reference) and throughout the study using clinical laboratory data and physical examination findings. Patients were monitored for treatment-emergent adverse event (AE) reports, whether reported spontaneously by the patient or by the investigator. A serious AE was defined according to the Medical Dictionary for Regulatory Activities (MedDRA version 9.0) as an AE that was fatal or life-threatening; required prolonged inpatient hospitalization; resulted in persistent or significant disability, congenital anomaly, birth defect, miscarriage, or elective abortion; or required medical/surgical intervention to prevent another serious outcome. Number and percentage of study patients with AEs were reported from signed informed consent up to 70 days after last study visit (5 times the estimated half-life of adalimumab). Assessments of drug safety and tolerability also compared the 2- and 4-week periods after administration of the syringe and pen, respectively. Routine hematology, serum chemistry and serology, and urinalysis tests were conducted through a certified clinical laboratory. Laboratory reference ranges were obtained prior to the initiation of the study and reviewed by the investigator for screening purposes.

A sample size of approximately 50 patients was needed to demonstrate equivalence between the injection-site pain scores following administration of the prefilled syringe vs. the pen with 80% statistical power, assuming an equivalence limit of ±5, a standard deviation (of the differences) of 1.25, and a 1-sided, Type-I error rate of 0.025. Evaluations of preference and injection-site pain covered all participants who received 1 injection with a syringe and at least 1 injection with the pen. Baseline characteristics, preferences, and other categorical data were summarized using means and percentages. An "exact" 95% CI was computed to compare the patients who either preferred the pen or had no preference with patients who preferred the prefilled syringe. Changes from baseline in injection-site pain were analyzed using paired student t-test and calculation of 95% CIs. Safety analyses covered all patients who received at least 1 injection. AE rates using each device were compared using the McNemar's test. All statistical tests were performed at the 0.05-level of statistical significance. The statistical analysis was performed using SAS®, Release 8.2 (SAS Institute, Inc, Cary, N.C.) with a UNIX Version 11.0 operating system.

Interim Study Results

Interim Study 1

An interim study examined statistical and descriptive analysis of information obtained from 17 patients, 11 had all 3 visits and 6 had 2 visits. The study also examined baseline and visit 1 data from another 7 patients.

Overall excellent results suggested that the pen is preferred over the syringe. Injection pain was comparable with either the pen or syringe, while post injection site pain showed differences, mostly in favor of the pen:

Most patients reported either no or minimal pain during injection with both devices.

The majority reported less post-injection site pain with the pen than the syringe (Mean values in a 0-10 scale: 3.6 (syringe); 2.4 (pen 1); 1.9 (pen 2)).

Preference: Practically all patients found superior the pen for all rating attributes such as overall preference, less pain, ease of use, convenience or safety. The pen was preferred in 63 out of 66 answers (6 preference questions to 11 patients).

All 11 patients considered likely (4) or extremely likely (7) switching to and recommending the pen to others.

Additional details of interim study 1, included the following:

Pain data: (17 patients pen 1; 11 patients pen 2) is shown below in Table 1.1, where injection pain (scale 0-10; mean values)—pen 'always' either same or lower pain than syringe

TABLE 1.1

|  | Injection pain (scale 0-10; mean values) - pen 'always' either same or lower pain than syringe |
| --- | --- |
| Syringe | 0.8 |
| pen 1 | 0.2 |
| pen 2 | 0.1 |

Table 1.2 below shows details of study 1 based on a different patient population described in Table 1.1 Post-injection site pain (scale 0-10; mean values)—11 patients reported similar or less pain with the pen, in 6 patients the pen increased pain from 1 to 3-5

|  | Injection pain (scale 0-10; mean values) |
| --- | --- |
| Syringe | 3.6 |
| pen 1 | 2.4 |
| pen 2 | 1.9 |

Preference Data (EF: Extremely fav; F fav; N: Neutral; U: unfav; EU: Extremely unfav)
Pen 1: overall impression was mostly EF (7) or F (6).
Pen 2: was mostly EF (6) or F (4). Patient 904 had EU in pen 2, although had EF in pen 1, but also had an 'extremely likely' to switch and recommend.

Interim Study 2

An interim study (following interim study 1 in time) examined 19 patients with 3 injections. The interim study 1 summary included exclusively preference results based on descriptive analyses obtained from 31 patients: 19 had all 3 visits, 5 had 2 visits and 7 had just the first visit.

Overall excellent results confirming that the pen is definitely preferred over the syringe. Practically all patients found superior the pen for all rating attributes such as overall preference, less pain, ease of use, convenience or safety. The pen was preferred in 106 out of 114 answers (6 preference questions to 19 patients).

18 out of 19 patients preferred the pen and considered extremely likely or likely switching to and recommending the pen to others. One patient preferred the syringe, considered unlikely to switch and was neutral regarding recommendation.

Additional details included the following:
Subject Impression of Syringe:
n=31
Extremely favorable=2 (6.5%)
Favorable=8 (26%)
Neutral=11 (35%)
Unfavorable=8 (26%)
Extremely Unfavorable=2 (6.5%)
Subject Impression After Visit 2-1st Pen Injection
n=24
Extremely Favorable=12 (50%)
Favorable=8 (33.3%)
Neutral=2 (8.3%)
Unfavorable=1 (4.2%)
Extremely Unfavorable=1 (4.2%)
Subject Impression After Visit 3-2nd Pen Injection
n=19
Extremely Favorable=11 (57.9%)
Favorable=6 (31.6%)
Neutral=1 (5.3%)
Extremely Unfavorable=1 (5.3%)

Preference Ratings After Visit 3-2nd Pen Injection
n=19
When asked overall, based on your experience with the HUMIRA® Syringe and the pen which do you prefer? 18 of 19 subjects preferred the pen. One subject preferred the Syringe.
When asked which method of injecting HUMIRA® was preferred in terms of:
Ease of Use—All 19 subjects preferred the pen
Convenience—18 subject preferred the pen; 1 subject reported No Preference
Time it took to complete the Injection—17 of 19 subject preferred the pen; 2 subjects had No Preference
Safety—17 of 19 subject preferred the pen; 2 subjects had No Preference
Less Pain—16 of 19 subject preferred the pen; 1 subject preferred the Syringe; and 2 subjects has No Preference
When asked "How likely would you be to use the pen if it was available at the same cost as the Syringe?" 12 subjects reported "Extremely Likely"; 6 subjects reported "Likely"; and 1 subject reported "Unlikely"
When asked "How likely would you be to recommend the pen to another HUMIRA® user?" 11 users reported "Extremely Likely"; 7 users reported "Likely"; and 1 user reported "Neutral."
Some Comments Reported by Users Who Selected their Preference as the Pen:
"Easy, and less pain, quicker"
"Safer, faster & easier to administer no fear factor"
"Because I don't like needle I can actually see"
"Easier to hold/administer"
"Less painful quick and easy"
"It does it all for you"
"It takes the hassle of having to tab myself+control the injection out of the process. And id didn't seem to hurt as much."
"There is not as much pain"
"Convenience"
"Pain is less severe and lasts a shorter period"
Some Comments Reported by Users as to why they Did NOT Select the Syringe as their Preference:
"Hurts"
"More prep time, physical and mental"
"The syringe takes longer, more steps."
"Harder to use"
"Slower more pain"
"Harder to hold/administer"
"Could feel the sting when it goes in, more painful"
"With the syringe you have to push down until done vs. pen push down once and watch yellow tab till it stops"
"To me, the pen is easier, with less chance of error on my part"
"Because the pen is easier to use and not as much pain after:
"Slower injection time—more painful"
"Slow process—stings"
Info from the Subject Who Preferred the Syringe:
Ease of use—preferred the pen; Convenience—preferred pen; Time it took to complete injection—pen; Safety—pen; Less Pain—Syringe; How likely to use pen—Unlikely; How likely to recommend pen—Neutral
Comments—"I seem to be in better control of the injection needle. The second injection felt more painful than the syringe."

Interim Study 3

In interim study 3, the following answers were given in a survey of 35 patients:
Which method of injecting HUMIRA® would you prefer in terms of the time it took to complete the injection? pen (n=29); Syringe (n=2); no preference (n=4)

Which method of injecting HUMIRA® would you prefer in terms of safety? pen (n=31); syringe (n=0); no preference (n=4)

Results from Complete Study

Patient Disposition and Baseline Characteristics

A total of 52 patients were enrolled in the study and completed all 3 study visits. No patients discontinued treatment during the study. Baseline demographics and baseline survey results are included in Table 1.3. Patients enrolled in the study were treated with adalimumab for a mean treatment duration of 15.4 months and were self-administering adalimumab with a syringe for the majority of their treatment periods (mean duration of self-administration was 14.9 months). In addition, approximately 655 of patients were receiving concomitant methotrexate, and 35% were receiving concomitant steroid therapy. Patients were fairly equally divided as to whether they usually injected their adalimumab doses in the abdomen or thigh, whereas a small percentage alternated between sites. During the study, 29 patients (55.8%) selected their abdomens as their injection site, and 23 patients (44.2%) selected their thighs as their injection site.

TABLE 1.3

Baseline Demographics, Clinical Characteristics, and Survey Responses

| Characteristic | Overall Population (N = 52) |
|---|---|
| Mean age in years (SD) | 53.8 (12.1) |
| Mean disease duration of rheumatoid arthritis (SD) | 8 (7.5) |
| Gender, n (%) | |
| Female | 32 (61.5) |
| Male | 20 (38.5) |
| Race, n (%) | |
| White | 46 (88.5) |
| Black | 6 (11.5) |
| Other | 0 (0) |
| RA medications in past 12 months, n (%) | |
| Adalimumab | 52 (100) |
| Etanercept | 2 (3.8) |
| Infliximab | 2 (3.8) |
| Other | 1 (1.9) |
| Baseline Survey | N = 52 |
| Duration of adalimumab treatment (mos) | |
| Mean (SD) | 15.4 (9.8) |
| Median | 12.0 |
| Range | 3.0-40.0 |
| Duration of self-injecting adalimumab (mos) | |
| Mean (SD) | 14.9 (10.0) |
| Median | 12.0 |
| Range | 2.0-40.0 |
| Length of time to inject (min) | |
| Mean (SD) | 1.6 (4.1) |
| Median | 0.8 |
| Range | 0.2-30.1 |
| Usual injection site, n (%) | |
| Abdomen | 25 (48.1) |
| Thigh | 22 (42.3) |
| Both abdomen and thigh | 5 (9.6) |

RA = rheumatoid arthritis.

Injection-Site Pain

Injection-site pain ratings are included in Table 2. At Visit 1, immediately following the syringe injection, the mean injection-site pain rating was 3.7. Mean pain ratings decreased 37% to 2.3 at Visit 2 and 46% to 2.0 at Visit 3, immediately following the pen injection. Mean within group changes in injection-site pain immediately following the injection at Visit 2 (pen) and Visit 3 (pen) were statistically significantly reduced (P=0.002 and P<0.001, respectively) from Visit 1 (syringe) (Table 2). Mean pain rating 15-30 minutes post-injection were 0.8 at Visit 1; 0.2 at Visit 2; and 0.2 at Visit 3. Similarly, mean within group changes in injection-site pain 15-30 minutes post-injection at Visit 2 (pen) and Visit 3 (pen) were statistically significantly reduced (P=0.004 and P=0.001, respectively) from Visit 1 (syringe) (Table 2).

TABLE 2

Injection-Site Pain

| | | Full Analysis Set N = 52 | | |
|---|---|---|---|---|
| | | Within-Group Change | | |
| | Visit | from Week 1 | | P- |
| Visit | Mean | Mean ± SE | 95% CI | value |
| Immediately post-injection | | | | |
| Visit 1 (Week 1) (Syringe) | 3.7 | | | |
| Visit 2 (Week 3) (pen) | 2.3 | −1.4 ± 0.43 | −2.2, −0.5 | 0.002 |
| Visit 3 (Week 5) (pen) | 2.0 | −1.6 ± 0.44 | −2.5, −0.8 | <0.001 |
| 15-30 minutes post-injection | | | | |
| Visit 1 (Week 1) (Syringe) | 0.8 | | | |
| Visit 2 (Week 3) (pen) | 0.2 | −0.6 ± 0.19 | −1.0, −0.2 | 0.004 |
| Visit 3 (Week 5) (pen) | 0.2 | −0.6 ± 0.16 | −0.9, −0.2 | 0.001 |

Note:
The possible range for the assessment of pain is 0 (no pain) to 10 (pain as bad as it could be).

Overall Impressions

At Visit 1, patients were equally divided in rating their overall impressions of their first syringe injections. Approximately one-third of the patients rated their overall impressions of the syringe injection as "favorable" or "extremely favorable," approximately one-third were "neutral," and approximately one-third rated it as "unfavorable" or "extremely unfavorable" (Table 3). Following the use of the pen, more than 80% of the patients rated their overall impressions of the pen as "favorable" or "extremely favorable" at Visit 2 (86.5%) and Visit 3 (88.5%).

TABLE 3

Overall Impressions of Adalimumab Prefilled Syringe and Autoinjection pen

| | Syringe, n (%) | pen, n (%) | |
|---|---|---|---|
| | Visit 1 | Visit 2 | Visit 3 |
| Response | N = 52 | N = 52 | N = 52 |
| Extremely favorable | 2 (3.8) | 26 (50.0) | 33 (63.5) |
| Favorable | 15 (28.8) | 19 (36.5) | 13 (25.0) |
| Neutral | 18 (34.6) | 3 (5.8) | 3 (5.8) |
| Unfavorable | 14 (26.9) | 1 (1.9) | 2 (3.8) |
| Extremely unfavorable | 3 (5.8) | 3 (5.8) | 1 (1.9) |

Patient Preference

Figure 26:
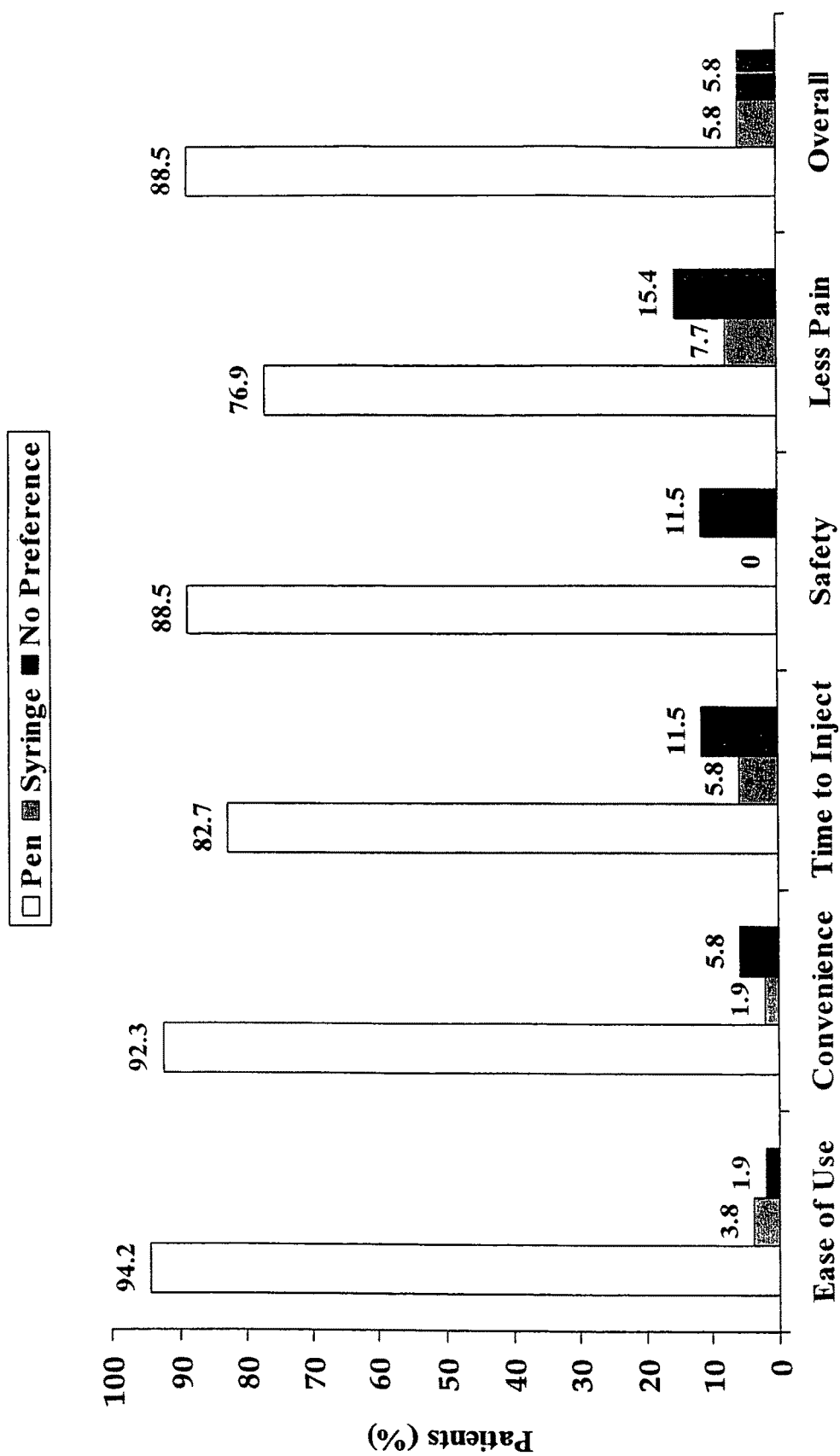
FIG. 26 shows results of final patient preference survey following Visit 3.

The final patient preference survey that was administered following Visit 3 showed that, overall, 88.5% (95% CI 84.1, 98.8) of patients preferred the pen, 5.8% (95% CI 1.2, 15.9) preferred the syringe, and 5.8% had no preference (FIG. 26). Patients were asked to list some of the reasons for their preferences. The majority of patients who chose the pen as their preferred delivery system said it was easier to use and less painful than the syringe. Other reasons why patients preferred the pen included the following: no bruising at injection site; faster administration time; less preparation time and fewer steps to follow; better control of the device; less force required; no need to push syringe to insert needle into skin; no view of the needle; fewer concerns with needle storage and disposal; and no need to draw back on syringe to check for blood. Patients who chose the syringe as their preferred delivery system gave the following reasons: familiarity with the syringe/no need for change; difficulty removing pen cap; better control of the injection needle; and less painful than the pen.

Figure 27:
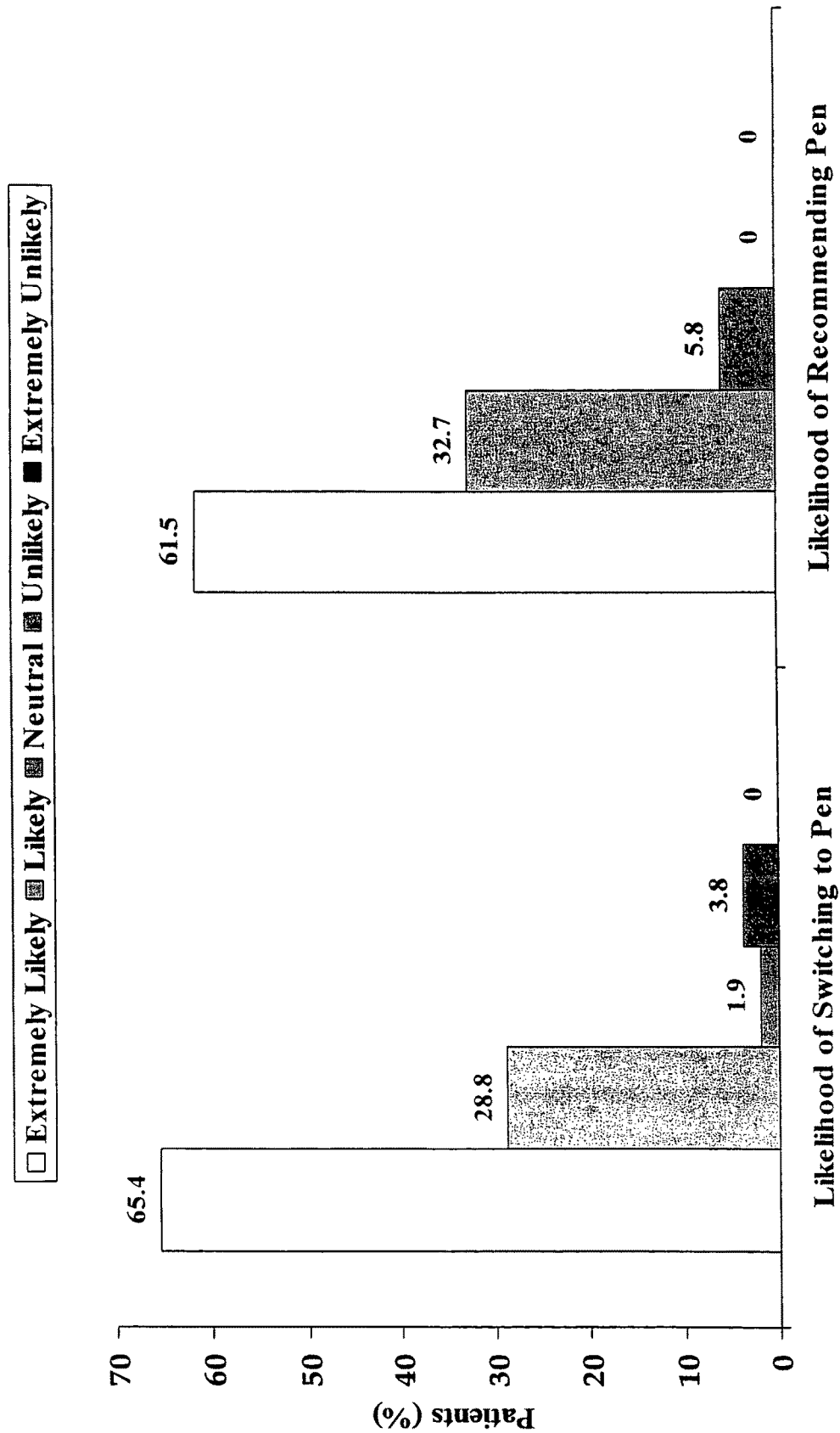
FIG. 27 shows results showing the likelihood of switching to pen and likelihood of recommending the pen to others.

When patients were asked to rate specific reasons for their preferences, more preferred the pen over the syringe for (in order from greatest to lowest percentage) the following: ease of use; convenience; overall safety and overall attributes (same percentage); less time to complete the injection, and less pain (FIG. 2). More than 94% of patients said they would be likely or extremely likely to use the pen if it was available at the same cost as the syringe (FIG. 27). Similarly, more than 94% of patients said they would recommend the pen to another patient who uses adalimumab (FIG. 27).

Therapy Compliance

At each visit, patients had their injection techniques assessed by a health care professional to help determine the effectiveness of the training procedure. Overall, patient preparation and injection techniques were rated at 98-100% compliant (per visit) for each component assessed (ie, prepared the injection site with alcohol, inspected the drug level and quality, removed the caps in order, prepared the skin plateau, kept the skin plateau during the injection, positioned the pen correctly, fired the pen correctly, kept constant pressure with no pull back, held the injection until complete, and observed the yellow stopper in the window when the injection was complete). Approximately 90% of patients noted that the instructional devices (video or brochures) used by the health care professionals provided adequate training.

Safety Assessments

No new safety signals were observed during this study. Adalimumab was demonstrated to be generally safe and well-tolerated irrespective of syringe or pen delivery. No statistically significant differences were observed between AEs reported during syringe use vs. pen use either in terms of overall AEs or by individual MedDRA preferred term. A total of 13 patients reported a treatment-emergent AE: 5 while using the prefilled syringe (9.6%) and 10 (19.2%) after 2 pen injections. Two patients reported an AE during both syringe and pen use. Most AEs were mild to moderate and included bronchitis, hypersensitivity, arthritic pain, cough, and rhinitis. Three infections and 1 drug hypersensitivity reaction were reported. Two patients had a serious AE while using the pen. Of these, a 69-year-old white male with a history of hypertension and coronary artery disease leading to triple bypass cardiac surgery required hospitalization because of exacerbation of congestive heart failure, a diagnosis first established in 1989. This patient received the second dose of adalimumab via pen once stabilized and recovered. The other patient was a 51-year-old white male who required hospitalization for the treatment of pneumonia approximately 71 days after the start of study treatment. No other TNF-antagonist events of interest, including malignancies, demyelinating events (including multiple sclerosis), or lupus-like reactions, were reported during this study. No patients discontinued from the study in response to a treatment-emergent AE, and no device failures were reported.

The final results of the study show that 46 out of 52 patients preferred the pen (88.5%), while 5.8% (n=3) had no preference and 5.8% preferred the PFS (n=3). In addition, 40 out of 52 patients thought the pen was less painful (76.9%), while 15.4% had no preference. Only 7.7% thought the PFS was less painful. Furthermore, patient responses indicated that the pen was easier to use, as 49 of 52 patients thought the pen was easier to use (94.2%). Finally, the pen was deemed more convenient, as 48 of 52 patients thought the pen was more convenient (92.3%). 61.5% (n=32) of the patients said that they would be likely to recommend the pen to another HUMIRA® user, while 32.7% (n=17) said they would be likely to recommend and 5.8% (n=3) were neutral on the issue. Additional results from the study are shown below in Tables 4-6.

TABLE 4

Results from questionnaire regarding "How painful was the HUMIRA ® injection you just administered?" (both immediately and 15-30 minutes)

| VISIT | N | WEEK 1 (SYRINGE) MEAN | VISIT MEAN |
|---|---|---|---|
| IMMEDIATELY POST INJECTION | | | |
| WEEK 3 (PEN) | 52 | 3.7 | 2.3@ |
| WEEK 5 (PEN) | 52 | 3.7 | 2.0* |
| 15-30 MIN POST INJECTION | | | |
| WEEK 3 (PEN) | 52 | 0.8 | 0.2& |
| WEEK 5 (PEN) | 52 | 0.8 | 0.2# |

*P-value <0.001
P-value 0.001
@P-value 0.002
&P-value 0.004

TABLE 5

Subject impression: overall impression

| IMPRESSION | WEEK 1 (SYRINGE) (N = 52) n (%) | WEEK 3 (PEN) (N = 52) n (%) | WEEK 5 (PEN) (N = 52) n (%) |
|---|---|---|---|
| EXTREMELY UNFAVORABLE | 3 (5.8) | 3 (5.8) | 1 (1.9) |
| UNFAVORABLE | 14 (26.9) | 1 (1.9) | 2 (3.8) |
| NEUTRAL | 18 (34.6) | 3 (5.8) | 3 (5.8) |
| FAVORABLE | 15 (28.8) | 19 (36.5) | 13 (25.0) |
| EXTREMELY FAVORABLE | 2 (3.8) | 26 (50.0) | 33 (63.5) |

TABLE 6

Method preferred in different cases

| Total n = 52 | Ease of use n (%) | Convenience n (%) | Time it took to complete the injection n (%) | Safety n (%) | Less pain n (%) |
|---|---|---|---|---|---|
| pen | 49 (94.2) | 48 (92.3) | 43 (82.7) | 46 (88.5) | 40 (76.9) |
| Syringe | 2 (3.8) | 1 (1.9) | 3 (5.8) | 0 | 4 (7.7) |
| No preference | 1 (1.9) | 3 (5.8) | 6 (11.5) | 6 (11.5) | 8 (15.4) |

The types and cumulative frequency of adverse events (AEs) during the 2-wk period after the syringe injection and the 4-wk period after the 2 pen injections were comparable. Five patients (9.6%) reported AEs, including bronchitis, hypersensitivity, arthritic pain, cough and rhinitis after syringe injection and 8 (15.4%) after pen injection. There were no AEs leading to discontinuation.

Although the pen was designed to offer patients greater convenience, it was unclear what attributes, such as less pain, would drive patients' preferences. This study showed that individual attributes—less injection pain, safety, ease of use, convenience, and time to complete the injection—all favored the pen over the syringe. In this study, the pen showed a statistically significant advantage regarding injection pain, which was reduced by 46% immediately after injection, and by 75% 15-30 minutes post-injection.

Regarding preference, patients were equally divided on their overall impressions of the syringe with respect to 5 prespecified categories (ie, "extremely favorable," "favorable," "neutral," "unfavorable," and "extremely unfavorable"). However, after switching to the pen, patients' overall impression ratings shifted significantly toward either "favorable" or "extremely favorable." Moreover, after only 2 injections with the pen, the majority of patients said they were "likely" or "extremely likely" to switch to the pen and to recommend the pen to another patient who was being treated with adalimumab, highlighting patients' quick acceptance of the pen and its features.

These results may have important treatment implications for patients who require long-term TNF inhibitor or other biologic therapies. Because of the relationship of patient preference to adherence to therapy (Schwartzman et al. *Arthritis Research & Therapy.* 2004;6(Suppl 2):S19-S23), a patient's preference for a specific route of administration may be a substantial factor in a physician's selection of a biologic therapy. Moreover, adherence to therapy is believed to be one of the most important factors in maintaining the long-term benefits of TNF-antagonist therapy, and, therefore, the lack of adherence can severely compromise the effectiveness of treatment (Schwartzman et al. (2004)).

In sum, the pen was determined by patients to be easier to use than a prefilled syringe. In addition, patients found that the pen was more convenient than the syringe and was less painful than the prefilled syringe. Patients preferred the HUMIRA® pen to the HUMIRA® PFS across all rating attributes. About 90% of the patients reported an overall preference for the pen compared to the prefilled syringe. 8 out of 10 patients also would recommend the pen to other patients using adalimumab. Finally, 80% of the patients rated the pen as less painful than the PFS.

This study indicates that patients believed that the adalimumab pen caused significantly less pain than the traditional prefilled syringe. In additions, adalimumab-experienced RA patients preferred subcutaneous injection of adalimumab with an autoinjection pen over injection with the prefilled syringe. Patients thought the pen was easier to use, more convenient, safer, and required less time to inject. With regard to the safety profile, no apparent differences were observed between the 2 delivery systems. The overall preference of patients for an autoinjection pen device may lead to increased adherence to therapy and, in turn, improved clinical outcomes during long-term therapy with self-administered biologic therapies.

EXAMPLE 2

Assessment of Relative Bioavailability, Safety, and Tolerability of Single Doses of Adalimumab Administered Via an Autoinjector Pen and a Prefilled Syringe Rheumatoid arthritis (RA) is a chronic, debilitating disease that requires long-term therapy that is safe and efficacious. Current tools of biologic drug delivery, prefilled syringes, are painful and cumbersome. Prefilled, disposable, autoinjector pens, like those described in the below example, allow for more convenient dosing.

The purpose of the following example was to compare the bioavailability, safety, and tolerability of adalimumab administered subcutaneously via an autoinjector pen vs. a prefilled syringe Study Design Adalimumab was administered via the Pen or a prefilled syringe in the abdomen or thigh to healthy adult volunteers in this Phase I, open-label, parallel group, multicenter study. Regimen A included a 40-mg subcutaneous dose of adalimumab via autoinjector pen, while Regimen B included a 40-mg subcutaneous dose of adalimumab via prefilled syringe.

Blood samples were collected by venipuncture prior to dosing (Hour 0); at Hours 4, 12, 24, 36, 48, 60, 72, 84, 96, 108, 120, 132, 144, 168, 192, 240, 288, 336, and 360; and at Weeks 3, 4, 5, 6, 7, and 8 after dosing. Serum concentrations of adalimumab were determined using a validated double antigen immunoassay. The assay had a lower limit of quantification of 3.125 ng/mL in diluted serum.

Main Inclusion Criteria included 18-55 years of age and patients were in general good health. Main Exclusion Criteria included pregnancy and a history of positive PPD skin test. Pharmacokinetic analysis included analyzing pharmacokinetic (PK) parameters that were estimated using non-compartmental methods. PK parameters included were: maximum observed serum concentration (Cmax); time to Cmax (Tmax); area under serum concentration-time curve (AUC) from Hour 0-360 (AUC0-360); and AUC from Hour 0-1344 (AUC0-1344)

Statistical analysis was performed using the following considerations. A four-way analysis of covariance (ANCOVA) was performed for Tmax and the logarithms of AUC and Cmax with regimen, injection site, study center, and sex as the factors. Body weight was the covariate. To assess bioequivalence of the regimens, a two one-sided test procedure was carried out for AUC and Cmax via 90% confidence intervals for the ratio of regimen central values. The ratio of regimen central values corresponds to the difference of the regimen main effects in the ANCOVA model.

Safety was evaluated based on assessments of adverse events (AEs), physical examinations, vital signs, and laboratory tests A total of 295 male and female healthy volunteers enrolled in the study. Of these, 146 volunteers received a 40-mg dose of adalimumab via an autoinjector pen and 149 subjects received a 40-mg dose of adalimumab via a prefilled syringe. Table 7 contains the summary statistics for demographic parameters

TABLE 7

Baseline Demographic Variables

| Characteristics | All Randomized Volunteers (N = 295) |
|---|---|
| Age (years) | 37.5 ± 10.6 |
| Weight (kg) | 72.4 ± 10.9 |
| Height (cm) | 168.9 ± 9.8 |
| BMI | 25.3 ± 2.7 |
| % Male | 49 |
| % Caucasian | 81 |

All values are Mean ± SD, except percentages.

Mean serum adalimumab concentration-time profiles were similar in the two regimens. The pharmacokinetic profiles of the pen and prefilled syringe were also comparable between the two injections sites, thigh and abdomen.

Pharmacokinetic parameters of adalimumab after administration of each of the two regimens were similar (Table 8). The Tmax, log-transformed Cmax, AUC0-360, and AUC0-1344 central values for the Pen were not statistically significantly different from those for the prefilled syringe (Table 8).

TABLE 8

Adalimumab Pharmacokinetic parameters in the Autoinjector Pen and the Prefilled Syringe

| Pharmacokinetic Parameters | Regimens | |
|---|---|---|
| | Adalimumab via Autoinjector Pen (N = 146) | Adalimumab via prefilled syringe (N = 147)* |
| Tmax (hours) | 142.3 ± 76.2 | 151.4 ± 88.5 |
| Cmax (µg/mL) | 4.8 ± 1.5 | 4.8 ± 1.5 |
| AUC0-360 (µg · hr/mL) | 1260 ± 352 | 1276 ± 373 |
| AUC0-1344 (µg · hr/mL) | 2454 ± 815 | 2544 ± 952 |

*N = 146 for AUC0-360 and AUC0-1344.
In both regimens a single 40-mg dose of adalimumab is administered subcutaneously.
All values are Mean ± SD.

The 90% confidence intervals for log-transformed AUC0-360, AUC0-1344, and Cmax were contained within the 0.80 to 1.25 range indicating that the autoinjector test Regimen A was bioequivalent to the prefilled syringe reference Regimen B at both subcutaneous locations, thigh and abdomen (Table 9)

TABLE 9

Relative Bioavailability and 90% Confidence Intervals for the Bioequivalence Assessment by Injection Site

| Regimens A vs. B | PK Parameters | Central Value* | | Relative Bioavailability | |
|---|---|---|---|---|---|
| | | Pen† (N = 146) | Prefilled Syringe† (N = 149) | Point Estimate‡ | 90% Confidence Interval |
| Abdomen | Cmax | 4.43 | 4.38 | 1.012 | 0.922-1.111 |
| | AUC0-360 | 1166 | 1138 | 1.025 | 0.931-1.129 |
| | AUC0-1344 | 2169 | 2242 | 0.968 | 0.858-1.091 |
| Thigh | Cmax | 4.62 | 4.89 | 0.944 | 0.860-1.037 |
| | AUC0-360 | 1205 | 1319 | 0.914 | 0.829-1.007 |
| | AUC0-1344 | 2332 | 2547 | 0.915 | 0.812-1.033 |

*Antilogarithm of the least squares means for logarithms.
†Regimen A: 40 mg adalimumab administered subcutaneously via an autoinjector. Regimen B: 40 mg adalimumab administered subcutaneously via a prefilled syringe.
‡Antilogarithm of the difference (Pen minus prefilled syringe) of the least squares means for logarithms.

The autoinjector was well-tolerated in this study, with a safety profile comparable to that of the prefilled syringe (Table 10)

TABLE 10

Adverse Events ≥2% in the Population

| | Autoinjector Pen N = 146 n (%) | Prefilled Syringe N = 149 n (%) |
|---|---|---|
| Any AE | 70 (48) | 60 (40) |
| Headache | 29 (20) | 28 (19) |
| Upper Respiratory Tract Infection | 9 (6) | 13 (9) |
| Nasal Congestion | 9 (6) | 7 (5) |
| Pain (Limbs) | 2 (1) | 7 (5) |
| Constipation | 7 (5) | 2 (1) |

No deaths or discontinuations due to adverse events occurred during the study. One volunteer reported a serious adverse event of appendicitis requiring surgery and hospitalization on Study Day 20. The subject requested to continue participation in the study following her release from the hospital, and was allowed to continue following a complete medical evaluation. The majority of the treatment-emergent adverse events were assessed by the investigators as not related or possibly related to the study drug and mild in severity.

In conclusion, the autoinjector pen was bioequivalent to the prefilled syringe. The two regimens were also bioequivalent at each injection site, abdomen and thigh. The safety profile of the pen was comparable to the safety profile of the prefilled syringe

EXAMPLE 3

Introduction of a HUMIRA® Automatic Injection Device as Compared to a Pre-Filled Syringe for Delivery of HUMIRA®

A HUMIRA® representative visits a physician who has previously prescribed HUMIRA® PFS to patients. The representative delivers an oral presentation to the physician in which the TOUCH study and the results thereof are described for the physician (for TOUCH study, see, for example, Example 1 above). In particular, the representative conveys to the physician that 90% of patients reported an overall preference for the HUMIRA® Pen compared to the PFS, 8 out of 10 would recommend the Pen to other HUMIRA® patients and 80% of patients rated the Pen as less painful than the PFS. Additionally, the representative provides to the physician a flipchart and a DVD, each of which describe the TOUCH study and convey that 90% of patients reported an overall preference for the HUMIRA® Pen compared to the PFS, 8 out of 10 would recommend the Pen to other HUMIRA® patients and 80% of patients rated the Pen as less painful than the PFS.

EXAMPLE 4

Methods of Training for Use of a HUMIRA® Automatic Injection Device

A HUMIRA® representative visits a physician who has previously prescribed HUMIRA® PFS to patients. The representative delivers an oral presentation to the physician describing how the HUMIRA® Pen is used to deliver a dose of HUMIRA® to a patient. This presentation includes instructions to carry out the following steps:
  (i) remove the HUMIRA® Pen from the refrigerator 15 to 20 minutes before injection;

(ii) choose an injection site on thigh or stomach (wherein the site should be at least one inch from a previous injection site and at least two inches from the navel) and wipe the injection site with an alcohol swab;
(iii) examine the HUMIRA® solution in the HUMIRA® Pen through a window in the Pen to make sure that the liquid is clear and colorless. Also, holding the Pen such that the needle end is pointing downward, check to make sure that the level of the liquid is the same as or close to a line visible through the window (to ensure the proper dosage is present);
(iv) remove caps from the needle end and activator button end of the Pen. Gently squeeze a sizeable area of cleaned skin and place the Pen at a 90-degree angle flush against the skin. Press the activator button, keeping the Pen firmly against the skin, and listen for a "click". Maintain pressure on the activator button and count to 10 seconds. Ensure that the yellow indicator in the display window appears in full view and stops; and
(v) dispose of the Pen in an appropriate container (e.g., a Sharps container).

Additionally, the representative provides to the physician a flipchart and a DVD that convey the instructions to carry out steps (i) to (v) as set forth above. Additionally, the representative provides to the physician a training kit, wherein the kit includes (1) a demonstration automatic injection device, which mimics the HUMIRA® Pen but lacks the needle and the HUMIRA® dose, (2) a brochure that conveys instructions to carry out steps (i) to (v) as set forth above and (3) an audiovisual device (VHS cassette or DVD) that conveys instructions to carry out steps (i) to (v) as set forth above.

Equivalents

Those skilled in the art will recognize, or be able to ascertain using no more than routine experimentation, many equivalents to the specific embodiments of the invention described herein. Such equivalents are encompassed by the following claims. The contents of all references, patents, patent applications, and published patent applications cited throughout this application are incorporated herein by reference.

The invention claimed is:

1. An automatic injection device for providing a subcutaneous injection of a substance into a user, comprising:
a housing having an open first end and a second end;
a syringe movably disposed in the housing, the syringe including a barrel portion for holding the substance, a hollow needle in fluid communication with the barrel portion for ejecting the substance from the syringe, and a bung for sealing the barrel portion and selectively applying pressure to the substance to force the substance through the hollow needle;
a syringe actuation component for first moving the syringe towards the first end of the housing such that the needle projects from the first end and for subsequently applying pressure to the bung, the syringe actuation component including a pressurizer, at a first end of the syringe actuation component, for selectively applying pressure to the bung, a rod comprising a compressible portion projecting from the rod along at least a portion of a length of the rod, the compressible portion having a first expanded position prior to entering the barrel portion of the syringe and a second compressed position for initiating movement of the bung and a flange between a second end of the syringe actuation component and the compressible portion; and
a first biasing mechanism for biasing the syringe actuation component towards the open first end of the housing, the first biasing mechanism disposed between the flange of the syringe actuation component and the second end of the housing.

2. The automatic injection device of claim 1, further comprising an activation button coupled to the housing for actuating the syringe actuation component.

3. The automatic injection device of claim 2, further comprising a latch for latching the syringe actuation component in a retracted position prior to actuation by the activation button.

4. The automatic injection device of claim 1, further comprising a window on the housing for viewing the interior of the housing.

5. The automatic injection device of claim 4, wherein the window has a substantially key-hole shape.

6. The automatic injection device of claim 4, wherein the window includes a fill line at a position in the window for indicating a full dose of a TNF inhibitor.

7. The automatic injection device of claim 1, further comprising an indicator for indicating when the syringe is empty.

8. The automatic injection device of claim 1, wherein the syringe contains a dose of a TNF inhibitor to be injected into a user.

9. The automatic injection device of claim 1, further comprising a removable cap for covering one of the first end of the housing or the second end of the housing.

10. The automatic injection device of claim 1, further comprising a needle sheath that advances over the needle projecting through the first end after ejection of the substance from the syringe.

11. The automatic injection device of claim 1, further comprising a dose of a TNF inhibitor loaded in the barrel portion of the syringe.

12. The automatic injection device of claim 1, wherein the compressible portion extends along a longitudinal length of the rod between a lower solid portion of the rod forming the pressurizer and an upper solid portion of the rod.

13. The automatic injection device of claim 1, wherein the compressible portion comprises:
   a central void extending at least along a portion of the syringe actuation component; and
   one or more flexible elbows provided on either side of the central void, wherein the one or more elbows project radially outwardly from the central void when the compressible portion is in the first expanded position, and wherein the one or more elbows are collapsed radially inwardly toward the central void when the compressible portion is in the second compressed position.

14. The automatic injection device of claim 1, wherein the flange is configured to hold the first biasing mechanism in a compressed position until actuation of the automatic injection device.

15. The automatic injection device of claim 1, wherein the syringe actuation component further comprises:
   a base extending distally from the flange toward the second end of the housing, the base configured to support the first biasing mechanism.

16. The automatic injection device of claim 15, wherein the base comprises:
   one or more flexible legs around which the first biasing mechanism coils.

17. An automatic injection device for providing a subcutaneous injection of a substance into a user, comprising:
   a housing having an open first end and a second end;
   a plunger including a rod configured to be connected or adjacent at a first end to a bung of a syringe, a compressible portion projecting from the rod along at least a portion of a length of the rod, the compressible portion having a first expanded inactivated position and a second compressed activated position for initiating movement of the bung, and a flange between a second end of the rod and the compressible portion; and
   a biasing mechanism for biasing the plunger towards the open first end of the housing, the biasing mechanism disposed about the second end of the rod between the flange and the second end of the housing.

18. The automatic injection device of claim 17, further comprising an activation button coupled to the housing for actuating the plunger.

19. The automatic injection device of claim 18, further comprising a latch for latching the plunger in a retracted position prior to actuation by the activation button.

20. The automatic injection device of claim 17, further comprising a window on the housing for viewing the interior of the housing.

21. An automatic injection device of any one of claims 1 or 17 comprising a dose of a TNFα inhibitor.

22. The automatic injection device of claim 21, wherein the TNFα inhibitor is selected from the group consisting of an anti-TNFα antibody, or an antigen-binding portion thereof, a TNF fusion protein, or a recombinant TNF binding protein.

23. The automatic injection device of claim 22, wherein the TNF fusion protein is etanercept.

24. The automatic injection device of claim 22, wherein the TNFα inhibitor is selected from the group consisting of infliximab, CDP 571, CDP 870, anti-TNF dAb, golimumab, adalimumab, etanercept, p55TNFRIgG and r-TBP-1.

25. The automatic injection device of claim 22, wherein the anti-TNFα antibody, or antigen-binding portion thereof, is selected from the group consisting of a chimeric antibody, a humanized antibody, a human antibody and a multivalent antibody.

26. The automatic injection device of claim 25, wherein the human anti-TNFα antibody, or antigen-binding portion thereof, is selected from the group consisting of:
   i) a human TNFα antibody, or antigen binding portion thereof, that dissociates from human TNFα with a $K_d$ of $1\times10^{-8}$ M or less and a $K_{off}$ rate constant of $1\times10^{-3}$ $s^{-1}$ or less, both determined by surface plasmon resonance, and neutralizes human TNFα cytotoxicity in a standard in vitro L929 assay with an $IC_{50}$ of $1\times10^{-7}$ M or less;
   ii) a human TNFα antibody, or antigen binding portion thereof, that:
      a) dissociates from human TNFα with a $K_{off}$ rate constant of $1\times10^{-3}$ $s^{-1}$ or less, as determined by surface plasmon resonance;
      b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;
      c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12;
   iii) a human TNFα antibody, or antigen binding portion thereof, that comprises a light chain variable region (LCVR) comprising the amino acid sequence of SEQ ID NO: 1 and a heavy chain variable region (HCVR) comprising the amino acid sequence of SEQ ID NO: 2; and
   iv) adalimumab.

27. The automatic injection device of claim 26, further comprising 40 mg of adalimumab.

28. The automatic injection device of claim 22, wherein the anti-TNFα antibody, or antigen-binding portion thereof, is selected from the group consisting of infliximab, golimumab, and adalimumab.

29. An automatic injection device of any one of claim 1 or 17, wherein the substance is a formulation comprising adalimumab, sodium chloride, monobasic sodium phosphate dihydrate, dibasic sodium phosphate dihydrate, sodium citrate, citric acid monohydrate, mannitol, polysorbate 80, and water.

30. The automatic injection device of claim 29, wherein the automatic injection device comprises a 40 mg dose of adalimumab.

31. The automatic injection device of claim 29, further comprising sodium hydroxide.

32. An article of manufacture comprising:
a) a packaging material; and
b) an automatic injection device of any one of claim 1 or 17 comprising a dose of a TNFα inhibitor.

33. An article of manufacture comprising an alcohol prep and a dose tray, wherein the dose tray comprises any one of the automatic injection devices of claim 1 or 17 comprising a dose of a TNFα inhibitor.

34. A method of using the automatic injection device of any one of claim 1 or 17 for administering a TNF inhibitor to a user.

35. An automatic injection device for providing a subcutaneous injection of a substance into a user, comprising:
a housing comprising:
an open first end,
a second end,
a window disposed in a side wall for viewing the interior of the housing, and
an indicator that aligns with the window when the substance has been injected into the user;
a syringe movably disposed in the housing, the syringe comprising:
a barrel portion for holding the substance,
a hollow needle in fluid communication with the barrel portion for ejecting the substance from the syringe, and
a bung for sealing the barrel portion and selectively applying pressure to the substance to force the substance through the hollow needle;
a syringe actuation component for first moving the syringe towards the open first end of the housing such that the needle projects from the open first end and for subsequently applying pressure to the bung, the syringe actuation component comprising:
a rod comprising:
an upper solid portion having a first end,
a lower solid portion having a second end operable to move the bung and to transmit an expulsion force thereto,
a projecting portion projecting from the rod along at least a portion of a length of the rod, the projecting portion comprising two or more flexible elbows on either side of a central void provided between the upper and lower solid portions and aligned along a central axis of the rod, the projecting portion having a first expanded position prior to entering the barrel portion of the syringe in which the flexible elbows project radially outwardly to form the central void, and the projecting portion having a second compressed position for applying the second end of the lower solid portion to the bung in which the flexible elbows are compressed radially inwardly toward the central void, and
a flange disposed between the first end of the upper solid portion of the rod and the projecting portion of the rod;
a first biasing mechanism for biasing the syringe actuation component towards the open first end of the housing, the first biasing mechanism disposed between the flange of the syringe actuation component and the second end of the housing;
a second biasing mechanism for holding the syringe retracted in the housing until the first biasing mechanism is released; and
a first removable cap for covering the open first end of the housing or the second end of the housing.

36. The automatic injection device of claim 35, wherein the central void is a longitudinally extending slit.

37. The automatic injection device of claim 35, wherein the housing is fixed relative to the syringe.

38. The automatic injection device of claim 35, further comprising:
an activation button coupled to the housing for actuating the syringe actuation component.

39. The automatic injection device of claim 38, further comprising:
a latch for latching the syringe actuation component in a retracted position prior to actuation by the activation button.

40. The automatic injection device of claim 35, wherein the syringe contains a dose of a TNF inhibitor to be injected into a user.

41. The automatic injection device of claim 35, further comprising:
a dose of a TNF inhibitor pre-loaded in the barrel portion of the syringe.

42. The automatic injection device of claim 41, wherein the TNF inhibitor comprises adalimumab.

43. The automatic injection device of claim 35, further comprising:
a needle sheath configured to advance over the needle projecting through the open first end of the housing after ejection of the substance from the syringe.

* * * * *